US006916918B2

(12) United States Patent
Yu et al.

(10) Patent No.: US 6,916,918 B2
(45) Date of Patent: *Jul. 12, 2005

(54) HUMAN GLANDULAR KALLIKREIN ENHANCER, VECTORS COMPRISING THE ENHANCER AND METHODS OF USE THEREOF

(75) Inventors: De Chao Yu, Foster City, CA (US); Daniel R. Henderson, Palo Alto, CA (US); Eric R. Schuur, Palo Alto, CA (US)

(73) Assignee: Cell Genesys, Inc., South San Francisco, CA (US)

(*) Notice: Subject to any disclaimer, the term of this patent is extended or adjusted under 35 U.S.C. 154(b) by 420 days.

This patent is subject to a terminal disclaimer.

(21) Appl. No.: 09/875,228

(22) Filed: Jun. 5, 2001

(65) Prior Publication Data

US 2002/0136707 A1 Sep. 26, 2002

Related U.S. Application Data

(63) Continuation of application No. 09/127,834, filed on Aug. 3, 1998, now abandoned.
(60) Provisional application No. 60/076,545, filed on Mar. 2, 1998, and provisional application No. 60/054,523, filed on Aug. 4, 1997.

(51) Int. Cl.[7] .......................... C07H 21/04; C12N 15/74
(52) U.S. Cl. .................................. 536/24.1; 435/320.1
(58) Field of Search ..................... 536/24.1; 435/320.1; 424/93.2, 233.1

(56) References Cited

U.S. PATENT DOCUMENTS

| | | |
|---|---|---|
| 4,353,888 A | 10/1982 | Sefton |
| 4,391,909 A | 7/1983 | Lim |
| 4,603,112 A | 7/1986 | Paoletti et al. |
| 4,683,195 A | 7/1987 | Mullis et al. |
| 4,683,202 A | 7/1987 | Mullis |
| 4,754,065 A | 6/1988 | Levenson et al. |
| 4,769,330 A | 9/1988 | Paoletti et al. |
| 4,777,127 A | 10/1988 | Suni et al. |
| 4,800,159 A | 1/1989 | Mullis et al. |
| 4,883,666 A | 11/1989 | Sabel et al. |
| 4,892,538 A | 1/1990 | Aebischer et al. |
| 5,017,487 A | 5/1991 | Stunnenberg et al. |
| 5,106,627 A | 4/1992 | Aesbischer et al. |
| 5,166,057 A | 11/1992 | Palese et al. |
| 5,219,740 A | 6/1993 | Miller et al. |
| 5,288,641 A | 2/1994 | Roizman |
| 5,328,470 A | 7/1994 | Nabel et al. |
| 5,354,674 A | 10/1994 | Hodgson |
| 5,501,662 A | 3/1996 | Hofmann |
| 5,635,383 A | 6/1997 | Wu et al. |
| 5,648,478 A | 7/1997 | Henderson |
| 5,656,465 A | 8/1997 | Panicali et al. |
| 5,658,785 A | 8/1997 | Johnson |
| 5,679,559 A | 10/1997 | Kim et al. |

(Continued)

FOREIGN PATENT DOCUMENTS

| | | |
|---|---|---|
| EP | 0 345 242 A2 | 12/1989 |
| EP | 0 345 242 A3 | 12/1989 |
| EP | 0 415 731 A2 | 3/1991 |
| EP | 0 415 731 A3 | 3/1991 |
| EP | 0 440 219 | 8/1991 |
| GB | 2200651 | 8/1988 |
| WO | WO 89/01973 A2 | 3/1989 |
| WO | WO 89/01973 A3 | 3/1989 |
| WO | WO 90/07936 | 7/1990 |
| WO | WO 91/02805 | 3/1991 |
| WO | WO 91/14696 | 10/1991 |
| WO | WO 91/16024 | 10/1991 |
| WO | WO 91/17424 | 11/1991 |
| WO | WO 91/17761 | 11/1991 |
| WO | WO 92/05250 | 4/1992 |
| WO | WO 92/05266 | 4/1992 |
| WO | WO 92/06180 | 4/1992 |

(Continued)

OTHER PUBLICATIONS

Trujillo et al (PNAS 88: 3797–3801, 1991).*
Wotton et al (J. Biol. Chem. 270(13): 7515–7522, 1995).*
Charron et al (J. Biol. Chem. 270(51): 30604–30610, 1995).*
Igrahachi et al (J. Biol. Chem. 271(16): 9666–9674, 1996).*
Schedlich et al (DNA 6(5): 429–437, (1987)).*
Adair et al., "Targeted homologous recombination at the endogenous adenine phosphoribosyltransferase locus in Chinese hamster cells" *Proc. Natl. Acad. Sci. USA* 86:4574–4578 (1989).
Aebischer et al., "Macroencapsulation of dopamine–secreting cells by coextrusion with an organic polymer solution" *Biomaterials* 12:50–56 (1991).
Aebischer et al., "Transplantation of polymer encapsulated neurotransmitter secreting cells: Effect of the encapsulation technique" *J. Biomech. Eng.* 113:178–183 (1991).
Angermann et al., "Cloning and expression of human salivary–gland kallikrein in *Escherichia coli.*" *Biochem J.* 262:787–793, abstract only (Sep. 1989).
Arnberg et al., "Fiber genes of adenoviruses with tropism for the eye and the genital tract" *Virol.* 227:239–244 (1997).

(Continued)

*Primary Examiner*—Dave T. Nguyen
*Assistant Examiner*—Richard Schnizer
(74) *Attorney, Agent, or Firm*—Steven B. Kelber; DLA Piper Rudnick Gray Cary US LLP

(57) ABSTRACT

Enhancers which preferentially increase the transcription of cis-linked coding sequences in prostate cells are provided. Methods of using DNA constructs comprising the enhancers to control transcription of heterologous polynucleotides are also provided. Delivery vehicles comprising the enhancers and methods of using the vehicles are also provided. Adenovirus vectors in which one or more genes are under transcriptional control of the enhancers of the invention are also provided. Further provided are methods of using the adenovirus vectors of the invention to confer selective cytotoxicity in mammalian cells.

14 Claims, 33 Drawing Sheets

U.S. PATENT DOCUMENTS

| | | | |
|---|---|---|---|
| 5,692,622 A | | 12/1997 | Hergeth |
| 5,705,385 A | | 1/1998 | Bally et al. |
| 6,197,293 B1 | * | 3/2001 | Henderson et al. ......... 424/93.2 |
| 6,436,394 B1 | * | 8/2002 | Henderson et al. ......... 424/93.2 |
| 6,495,130 B1 | * | 12/2002 | Henderson et al. ......... 424/93.2 |
| 6,585,968 B2 | * | 7/2003 | Little et al. ................ 424/93.2 |
| 6,676,935 B2 | * | 1/2004 | Henderson et al. ......... 424/93.2 |
| 2003/0068307 A1 | * | 4/2003 | Yu et al. .................. 424/93.21 |
| 2003/0118555 A1 | * | 6/2003 | Henderson et al. ......... 424/93.2 |
| 2003/0152553 A1 | * | 8/2003 | Little et al. ................ 424/93.2 |

FOREIGN PATENT DOCUMENTS

| | | |
|---|---|---|
| WO | WO 92/06693 | 4/1992 |
| WO | WO 92/13570 | 8/1992 |
| WO | WO 93/10218 | 5/1993 |
| WO | WO 93/11230 | 6/1993 |
| WO | WO 93/25234 | 12/1993 |
| WO | WO 93/25698 | 12/1993 |
| WO | WO 94/03622 | 2/1994 |
| WO | WO 94/20608 | 9/1994 |
| WO | WO 95/19434 | 5/1995 |
| WO | WO 95/26412 | 10/1995 |
| WO | WO 95/28494 | 10/1995 |
| WO | WO 96/00295 | 1/1996 |
| WO | WO 96/21036 A2 | 7/1996 |
| WO | WO 96/21036 A3 | 7/1996 |
| WO | WO 96/26745 | 9/1996 |
| WO | WO 96/40829 | 12/1996 |
| WO | WO 97/01358 | 1/1997 |
| WO | WO 97/20463 | 6/1997 |
| WO | WO 97/40163 | 10/1997 |
| WO | WO 97/42975 | 11/1997 |
| WO | WO 98/05797 | 2/1998 |
| WO | WO 98/35028 | 8/1998 |
| WO | WO 98/39464 | 9/1998 |

OTHER PUBLICATIONS

Ausubel, F.M., et al., eds. *Current Protocols in Molecular Biology*, Supplement 30, section 7.7.18, Table 7.7.1 (1987).

Ausubel, F.M. et al., eds. *Current Protocols in Molecular Biology*, Greene Publishing Associates (1989) Title Page and Table of Contents Only.

Bailey et al., "Cell type specific regulation of expression from the Ad40 E1B promoter in recombinant Ad5/Ad40 viruses", *Virology* 202:695–706 (1994).

Bailey et al., "Enteric adenovirus type 40: Expression of E1B proteins in vivo and in vivo" *Virology* 193:631–641 (1993).

Barba et al., "Thymidine kinase-mediated killing of rat brain tumors" *J. Neurosurg* 79:729–735 (1993).

Beato, "Gene Regulation by steriod hormones" *Cell* 56:335–344 (1989).

Behr et al., "Efficient gene transfer into mammalian primary endocrine cells with lipopolyamine-coated DNA" *Proc. Natl. Acad. Sci USA* 86:6982–6986 (1989).

Behringer et al., "Dwarf mice produced by genetic ablation of growth hormone-expressing cells" *Genes Dev.* 2:453–461 (1988).

Berkner and Sharp, "Generation of adenovirus by transfection of plasmids" *Nucl. Acids Res.* 11(17):6003–6020 (1983).

Berkner, "Development of adenovirus vectors for the expression of heterologous genes" *BioTechniques* 6(7):616–618, 620–624, 626, 628, 629 (1988).

Bett et al., "An efficient and flexible system for construction of adenovirus vectors with insertions or deletions in early regions 1 and 3" *Proc. Natl. Acad. Sci USA* 91:8802–8806 (1994).

Bett et al., "Packaging capacity and stability of human adenovirus type 5 vectors" *J. Virology* 67(10):5911–5921 (1993).

Boulikas "Gene therapy of prostate cancer:p53, suicical genes, and other targets" *Anticancer Res.* 17:1471–1505 (1997).

Braun et al., "Immunogenic duplex nucleic acids are nuclease resistant" *J. Immunol.* 141(6):2084–1089 (1988).

Bridge et al., "Redundant control of adenovirus late gene expression by early region 4" *J. Virol.* 63(2):631–638 (1989).

Broach et al. "Vectors for high-level, inducible expression of cloned genes in yeast" *Experimental Manipulation of Gene Expression*, M. Inouye , ed., Academic Press, pp. 83–117 (1983).

Capecchi, "Altering the genome by homologous recombination" *Science* 244:1288–1292 (1989).

Carson–Jurica et al., "Steroid receptor family: Structure and functions" *Endocr. Rev.* 11(2):201–220 (1990).

Chander and Schreier, "Artificial viral envelopes containing recombinant human immunodeficiency virus (HIV)gp160" *Life Sci.* 50(97):481–489 (1992).

Charlesworth et al., "Detection of a prostate–specific protein, human glandular kallikrein (hK2), in sera of patients with elevated prostate–specific antigen levels" *Urology* 49(3):487–493 (1997).

Chaturvedi et al., "Stabilization of triple–stranded oligonucleotide complexes: use of probes containing alternating phosphodiester and stereo–uniform cationic phosphoramidate linkages" *Nucleic Acids Res.* 24(12):2318–2323 (1996).

Chaudhary et al., "A recombinant single–chain immunotoxin composed of anti–tac variable regions and a truncated diphtheria toxin" *Proc. Natl. Acad. Sci. USA* 87:9491–9494 (1990).

Chen et al., "Gene therapy for brain tumors: Regression of experimental gliomas by adenovirus–mediated gene transfer in vivo" *Proc. Natl. Acad. Sci. USA* 91:3054–3057 (1994).

Clements, "The glandular kallikrein family of enzymes: Tissue–specific expression and hormal regulation" *Endocr. Rev.* 10(4):393–419 (1989).

Cleutjens et al. "An androgen response element in a far upstream enhancer region is essential for high, androgen-regulated activity of the prostate–specific antigen promoter" *Molec. Endocrinol.* 11(2)148–161 (1997).

Cold Spring Harbor Laboratory, Second Edition, *RNA Tumor Viruses* (1985) Title page and table of contents only.

Coligan et al., eds. *Current Protoocols in Immunology*, vols. 1, 2 and 3 (1991) Title page and table on contents only.

Cornetta et al., "No retroviremia or pathology in long–term follow–up of monkeys exposed to a murine amphotropic retrovirus" *Hum Gene Ther* 2:215–219 (1991).

Crooke and Lebleu, eds. *Antisense Research and Applications*, CRC Press (1993) Title page and table of contents only.

Dai et al., "Gene therapy via primary myoblasts: Long–term expression of factor IX protein following transplantation in vivo" *Proc. Natl. Acad. Sci. USA* 89:10892–10895 (1992).

Dai et al. "Androgenic up–regulation of androgen receptor cDNA expression in androgen–independent prostate cancer cells" *Steroids* 61:531–539 (1996).

Darson et al., "Human glandular kallikrein 2 (hK2) expression in prostatic intraepithelial neoplasia and adenocarcinoma: A novel prostate cancer marker" *Urology* 49(6):857–862 (1997).

De Wet et al., "Firefly luciferase gene: structure and expression in mammalian cells" *Mol. Cell. Biol.* 7(2):725–737 (1987).

Dietrich et al., "Delivery of antigen–encoding plasmid DNA into the cytosol of macrophages by attenuated suicide *Listeria monocytogenes*" *Nature Biotech* 16:181–185 (1998).

Dignam et al., "Accurate transcription initiation by RNA polymerase II in a soluble extract from isolated mammalian nuclei" *Nucleic Acids Res.* 11(5):1475–1489 (1983).

Faller et al., "Liposome encapsulation of retrovirus allows efficient superinfection of resistant cell lines" *J. Virol.* 49(1):269–272 (1984).

Felgner and Ringold, "Cationic liposome–mediated tranfection" *Nature* 337:387–388 (1989).

Fisher–Hoch et al. "Protection of rhesus monkeys from fatal Lassa fever by vaccination with a recombinant vaccinia virus containing the Lassa virus glycoprotein gene" *PNAS USA* 86:317–321 (1989).

Flexner et al., "Attenuation and immunogenicity in primates of vaccinia virus recombinants expressing human interleukin–2" *Vaccine* 8(1):17–21 (1990).

Flint "Expression of adenoviral genetic information in productively infected cells" *Biochem. Biophys. Acta* 651:175–208 (1982).

Flint "Regulation of adenovirus mRNA formation" *Advances Virus Research* 31:169–228 (1986).

Frankel et al., "Selection and characterization of ricin toxin A–chain mutations in *Saccharomyces cerevisiae*" *Mol. Cell. Biol.* 9(2):415–420 (1989).

Freshney, ed. *Animal Cell Culture* (1987) Title page and table of contents only.

Fukushima et al., "Nucleotide sequence of cloned cDNA for human pancreatic kallikrein." *Biochemistry* 24:8037–8043, Abstract Only (Dec. 1985).

Furth "Gene transfer by biolistic process" *Mol. Biotechnol.* 7:139–143 (1997).

Gacesa and Ramji, *Vectors*, John Wiley & Sons (1994) Title page and table of contents only.

Gait, ed., *Oligonucleotide Synthesis* MRC Laboratory of Molecular Biology (1984) Title page and table of contents only.

Gao and Huang, "A novel cationic liposome reagent for efficient transfection of mammalian cells" *Biochem. Biophys. Res. Commun.* 179(1):280–285 (1991).

Gennaro, ed., *Remington The Science and Practice of Pharmacy* 19th edition, vol. 1 and 2 (1995) Title page and table of contents only.

Gennaro, ed., *Remington's Pharmaceutical Sciences*, 18th edition (1990) Title page and table of contents only.

Ghosh–Choudhury and Graham, "Stable transfer of a mouse dihydrofolate reductase gene into a deficient cell line using human adenovirus vector" *Biochem. Biophys. Res. Commun.* 147(3):964–973 (1987).

Ghosh–Choudhury et al., "Protein IX, a minor component of the human adenovirus capsid, is essential for the packaging of full length genomes" *EMBO Journal.* 6(6):1733–1739 (1987).

Graham et al., "A new technique for the assay of infectivity of human adenovirus 5 DNA" *Virology* 52:456–467 (1973).

Graham et al. "Characteristics of a human cell line transformed by DNA from human adenovirus type 5" *J. Gen. Virol.* 36:59–72 (1977).

Graham, "Covalently closed circles of human adenovirus DNA are infectious" *EMBO Journal* 3(12):2917–2922 (1984).

Graham, "Growth of 293 cells in suspension culture" *J. Genetic Virology* 68:937–940 (1987).

Grand, "The structure and functions of the adenovirus early region 1 proteins" *Biochem. J.* 241–25–38 (1987).

Hallenbeck, O. et al., "Novel Tumor Specific Replication Competent Adenoviral Vectors for Gene Therapy of Cancer" *Cancer Gene Therapy*, 3(6):S19–S20 (1996).

Hara et al., "In vivo gene delivery to the liver using reconstituted chylomicron remnants as a novel nonviral vector" *Proc. Natl. Acad. Sci. USA* 94:14547–14552 (1997).

Hayashi et al., "Expression of a thyroid hormone–responsive recombinant gene introduced into adult mice livers by replication–defective adenovirus can be regulated by endogenous thyroid hormone receptor" *J. Biol. Chem.* 269(39):23872–23875 (1994).

Hillier et al., GenBank Accession No. T69719 (Mar. 1995).

Hodgson and Solaiman, "Virosomes: Cationic liposomes enhance retroviral transduction" *Nature Biotechnol.* 14:339–342 (1996).

Hoffman et al., "NGF released from a polymer matrix prevents loss of ChAT expression in basal forebrain neurons following a fimbria–fornix lesion" *Expt. Neurobiol.* 110(1):39–44 (1990).

Huber et al., "VDEPT: An enzyme/prodrug gene therapy approach for the treatment of metastic colorectal cancer" *Adv. Drug Delivery Rev.* 17:279–292 (1995).

Hwu et al., "Functional and molecular characterization of tumor–infiltrating lymphocutes transduced with tumor necrosis factor–alpha cDNA for the gene therapy of cancer in humans" *J. Immunol.* 150(9):4104–4115 (1993).

Jaeger et al., "Polymer encapsulated dopaminergic cell lines as 'alternative neural grafts'" *Prog. Brain Res.* 82:41–46 (1990).

Jaffe et al., "Adenovirus–mediated in vivo gene transfer and expression in normal rat liver" *Nat. Genet.* 1:372–378 (1992).

Jakoby, ed., *Methods in Enzymology*, Academic Press, Inc. (1979) Title page and table of contents only.

Johnson et al., "Targeting of nonexpressed genes in embryonic stem cells via homologous recombination" *Science* 245 (4923):1234–1236 (1989).

Kay et al., "Hepatic gene therapy: Persistant expression of human alpha 1–antitrypsin in mice after direct gene delivery in vivo" *Human Gene Therapy* 3:641–647 (1992).

Kit, "Recombinant–derived modified–live herpesvirus vaccines" *Adv. Exp. Med. Biol.* 251:219–236 (1989).

Kolberg, "Gene transfer virus contaminant linked to monkeys' cancer " *J. NIH Res.* 4:43–44 (1992).

Koole et al., "Sustained local drug delivery from a radiopaque implanted reservoir" *Nature Biotech.* 16(2):172–176 (1998).

Kroon et al., "The transcriptional regulatory strategy of the rat tissue kallirein gene family" *Genes and Function* 1(5–6):309–319 (1997).

Kunkel, "Rapid and efficient site–specific mutagenesis without phenotypic selection" *Proc. Natl. Acad Sci. USA* 82:488–492 (1985).

Lamb et al., "Nucleotide sequence of cloned cDNA coding for preproricin" *Eur. J. Biochem.* 148:265–270 (1985).

Latimer et al., "Specificity of monoclonal antibodies produced against phosphorothioate and ribo modified DNAs" *Mol. Immunol.* 32(14/15):1057–1064 (1995).

Le Gal Le Salle et al., "An adenovirus vector for gene transfer into neurons and glia in the brain" *Science* 259:988–990 (1993).

Lindzey et al., "Molecular mechanisms of androgen action" *Vitamins and Hormones* 49:383–432 (1994).

Litzinger and Huang, "Phosphatidylethanolamine liposomes: drug delivery, gene transfer and immunodiagnostic applications" *Biochimica et Biophysica Acta* 1113:201–227 (1992).

Lundwall et al., "Molecular cloning of human prostate specific antigen cDNA" *FEBS Lett.* 214(2):317–322 (1987).

Lundwall, "Characterization of the gene for prostate–specific antigen, a human glandular kallikrein" *Biochem. Biophys. Res. Commun.* 161(3):1151–1159 (1989).

Luytjes et al., "Amplification, expression, and packaging of a foreign gene by influenza virus" *Cell* 59:1107–1113 (1989).

Mackett et al., "Vaccinia virus: A selectable eukaryotic cloning and expression vector" *Proc. Natl. Acad. Sci. USA* 79:7415–7419 (1982).

Mahato et al., "Cationic lipid–based gene delivery systems: pharmaceutical perspectives" *Pharm. Res.* 14(7):853–859 (1997).

Mansour et al., "Disruption of the proto–oncogene int–2 in mouse embryo–derived stem cells: a general strategy for targeting mutations to non–selectable genes" *Nature* 336:348–352 (1988).

Mastrangeli et al., "Diversity of airway epithelial cell targets for in vivo recombinatn adenovirus–mediated gene transfer" *J. Clin. Invest.* 91:225–234 (1993).

Maxwell et al., "Cloning, sequence determination, and expression in transfected cells of the coding sequence for the tox 176 attenuated diphtheria toxin A chain" *Mol. Cell. Biol.* 7:1576–1579 (1987).

McGrory et al., "A simple technique for the rescue of early region I mutations into infectious human adenovirus type 5" *Virol.* 163:614–617 (1988).

McKinnon, "Tn5 mutatgenesis of the transforming genes of human adenovirus type 5" *Gene* 19:33–42 (1982).

McMichael et al., "Cytotoxic T–cell immunity to influenza" *N. Eng. J. Med.* 309(1):13–17 (1983).

Melton, D.A. ed., *Antisense RNA and DNA* Cold Spring Harbor Laboratory, Cold Spring Harbor, NY (1988) Title page and table of contents only.

Messing et al., "$P_0$ promoter directs expression of reporter and toxin genes to Schwann cells of transgenic mice" *Neuron* 8:507–520 (1992).

Miller and Calos, eds., *Gene Transfer Vectors for Mammalian Cells*, Cold Spring Harbor Laboratory (1987) Title page and table of contents only.

Miller et al., "Gene Transfer by retrovirus vectors occurs only in cells that are actively replicating at the time of infection" *Mol. Cell Biol.* 10(8):4239–4242 (1990).

Miller et al., "Progress toward human gene therapy" *Blood* 76(2):271–278 (1990).

Morris, "hGK–1: A Kallikrein gene expressed in human prostate" *Clin Exp. Pharm. Phuysiol.* 16:345–351 (1989).

Moss and Flexner, "Vaccinia virus expression vectors" *Annals of the NY Acad. Sci.* 569:86–103 (1989).

Mulligan et al., "Synthesis of rabbit beta–globin in cultured monkey kidney cells following infection with a SV40 beta-globin recombinant genome" *Nature* 277·108·114 (1979).

Mullis et al., eds. *PCR: The Polymerase Chain Reaction*, Birkauswer Press, Boston (1994) Title Page and table of contents only.

Murtha et al., "Androgen induction of a human prostate–specific kallikrein, hKLK2: Characterization of an androgen response element in the 5' promoter region of the gene" *Biochem.* 32:6459–6464 (1993).

Muzyczka et al., "Use of adeno–associated virus as a general transduction vector for mammalian cells" *Curr. Topics Microbiol. Immunol.* 158:97–129 (1992).

Naldini et al., "In vivo gene delivery and stable transduction of nondividing cells by a lentiviral vector" *Science* 272–263·267 (1996).

Nevins, "Mechanisms of viral–mediated trans–activation of transcription" *Adv. Virus Res.* 37:35–83 (1989).

Overbaugh et al, "Molecular cloning of feline leukemia virus that induces fatal immunodeficiency disease in cats" *Science* 239(4842)906·910 (1988).

Ow et al., "Transient and stable expression of the firefly luciferase gene in plant cells and transgenic plants" *Science* 234·856·859 (1986).

Palmiter et al., "Cell lineage ablation in transgenic mice by cell–specific expression of a toxin gene" *Cell* 50:435–443 (1987).

Pang et al., "Identification of a positive regulatory element responsible for tissue–specific expression of prostate–specific antigen" *Cancer Res.* 57:495·499 (1997).

Pawelek et al, "Tumor–targeted Salmonella as a novel anticancer vector" *Cancer Res.* 57:4537–4544 (1997).

Peyrottes et al., "Oligodeoxynucleoside phosphoramidates (P–NH$_2$): synthesis and thermal stability of duplexes with DNA and RNA targets" *Nucleic Acids Res.* 24(10):1841–1848 (1996).

Piatak et al., "Expression of soluble and fully functional ricin A chain in *Escherichia coli* is temperature–sensitive" *J. Biol. Chem.* 263(10):4837·4843 (1988).

Powers et al., "Anterior pituitary glandular kallikrein: a putative prolactin processing protease." *Mol. Cell Enocrinol.* 90:C15·20 (Jan. 1993).

Pozansky, "Gene transfer into human lymphocytes by a defective human immunodeficiency virus type 1 vector" *J. Virol.* 65(1):532–536 (1991).

Qiu et al., In situ hybridization or prostate–specific antigen mRNA in human prostate *J. Urol.* 144(6):1550–1556 (1990).

Quantin et al., "Adenovirus as an expression vector in muscle cells in vivo" *Proc. Natl. Acad. Sci. USA* 89:2581·3584 (1992).

Ragot et al., "Efficient adenovirus–mediated transfer of a human minidystrophin gene to skeletal muscle of mdx mice" *Nature* 361:647·650 (1993).

Ram et al., "In situ retroviral–mediated gene transfer for the treatment of brain tumors in rats" *Cancer Res.* 53:83–88 (1993).

Riegman et al., "Characterization of the human Kallikrein locus." *Genomics* 14:6–11, entire document (Feb. 1992).

Riegman et al., "The promoter of the prostate–specific antigen gene contains a functional androgen responsive element" *Molec. Endocrin.* 5(12):1921–1930 (1991).

Rodriguez et al., "Prostate attenuated replication competent adenovirus (ARCA) CN706: A selective cytotoxic for prostate-specific antigen-positive prostate cancer cells" *Cancer Res.* 57:2559–2563 (1997).

Rols et al., "In vivo electrically mediated protein and gene transfer in murine melanoma" *Nature Biotech* 16(2):168–171 (1998).

Rosenfeld et al., "Adenovirus-mediated transfer of a recombinant alpha1-antitrypsin gene to the lung epithelium in vivo" *Science* 252:431–434 (1991).

Rosenfeld et al., "In vivo transfer of the human cystic fibrosis transmembrane conductance regulator gene to the airway epithelium" *Cell* 68:143–155 (1992).

Sambrook et al., *Molecular Cloning, A Laboratory Manual*, 2nd Edition, Cold Spring Harbor Laboratory Press, Cold Spring Harbor, NY (1989) Title page and table of contents only.

Schedlich et al., "Primary structure of Human glandular kallikrein gene." *DNA* 6:429–437 (Aug. 1995).

Schedlich et al., GenEmbol Accession No. M18156 (Aug. 1995).

Schreier et al., "(Patho)physiologic pathways to drug targeting: Artificial viral envelopes" *J. Molec. Recognition* 8(1/2):59–62 (1995).

Schultz et al., "Oligo-2'-fluoro-2'-deoxynucleotide N3'-P5' Phosphoramidates: synthesis and properties" *Nucleic Acids Res.* 24(15):2966–73 (1996).

Schuur et al., "Chimeras of herpes simplex viral VP 16 and jun are oncogenic" *Cell Growth and Differ.* 4:761–768 (1993).

Schuur et al, "Prostate-specific antigen expression is regulated by an upstream enhancer" *J. Biol. Chem.* 272(12):7043–7051 (1996).

Sefton et al., "Microencapsulation of mammalian cells in a water insoluble polyacrylate by coextrusion and interfacial precipitation" *Biotechnol. Bioeng.* 29:1135–1143 (1987).

Stratford-Perricaudet et al., "Evaluation of the transfer and expression in mice of an enzyme-encoding gene using a human adenovirus vector" *Human Gene Therapy* 1:241–256 (1990).

Stratford-Perricaudet et al., "Widespread long term gene transfer to mouse skeletal muscles and heart" *J. Clin. Invest.* 90:626–630 (1992).

Sugarmori et al., "Microencapsulation of pancreatic islets in a water insoluble polyacrylate" *Trans: Am. Soc. Artif. Intern. Organs* 35:791–799 (1989).

Swaminathan et al., "Regulation of adenovirus E2 transcription unit" *Curr. Topics in Microbiol. And Immunol.* 199 part 3:177–194 (1995).

Takamiya et al., "Gene therapy of malignant brain tumors: A rat glioma line bearing the herpes simplex virus type 1-thymidine kinase gene and wild type retrovirus kills other tumor cells" *J. Neurosci. Res.* 33:493–503 (1992).

Takiff et al., "Propagation and in vitro studies of previously non-cultivable enteral adenoviruses in 293 cells" *Lancet* 11:832–834 (1981).

Tilley et al., "Characterization and expression of a cDNA encoding the human androgen receptor" *Proc. Natl. Acad. Sci. USA* 86:327–331 (1989).

Tollefson et al., "The 11,600-$M_w$ protein encoded by region E3 of adenovirus is expressed early but is greatly amplified at late stages of infection" *J. Virol.* 66(6):3633–3642 (1992).

Tollefson et al., "The adenovirus death protein (E3–11.6K) is required at very late stages of infection for efficient cell lysis and release of adenovirus from infected cells" *J. Virol.* 70(4):2296–2306 (1996).

Tremblay et al., "Immunohistochemical study suggesting a complementary role of kallikreins hK2 and hK3 (prostate-specific antigen) in the functional analysis of human prostate tumors" *Am. J. Pahtol.* 150(2):455–459 (1997).

Trubetskoy et al., "Cationic liposomes enhance targeted delivery and expression of exogenous DNA mediated by N-terminal modified poly($_L$-lysine)-antibody conjugate in mouse lung endothelial cells" *Biochem. Biophys. Acta* 1131:311–313 (1992).

Verma and Somia, "Gene therapy-promises, problems and prospects" *Nature* 389–239–242 (1997).

Vile and Hart, "In vitro and in vivo targeting of gene expression to melanoma cells" *Cancer Res.* 53:962–967 (1993).

Vile and Hart, "Use of tissue-specific expression of the herpes simplex virus thymidine kinase gene to inhibit growth of established murine melanomas following direct intratumoral injection of DNA" *Cancer Res.* 53(17):3860–3864 (1993).

Virtanen et al., "mRNAs from human adenovirus 2 early region 4" *J. Virol.* 51(3):822–831 (1984).

Voet and Voet, In Biochemistry, Second Edition, John Wiley and Sons, Publishers. p. 930, col. 1 (1995).

Wagner et al., "Transferrin-polycation conjugates as carriers for DNA uptake into cells" *Proc. Natl. Acad. Sci USA* 87:3410–3414 (1990).

Wang and Huang, "Highly efficient DNA delivery mediated by pH·sensitive immunoliposomes" *Biochemistry* 28:9508–9514 (1989).

Wang and Huang, "pH-sensitive immunoliposomes mediate target-cell specific delivery and controlled expression of foreign gene in mouse" *Proc. Natl. Acad. Sci. USA* 84:7851–7855 (1987).

Wang and Huang, :Plasmid DNA absorbed to pH-sensitive liposomes efficiently transforms the target cells *Biochem Biophys. Res. Commun.* 147(3):980–985 (1987).

Wang et al., "Expression of the APRT gene in an adenovirus vector system as a model for studying gene therapy" *Adv. Exp. Med. Biol.* 309B:61–66 (1991).

Weinberg et al., "A cell line that supports the growth of a defective early region 4 deletion mutant of human adenovirus type 2" *Proc. Natl. Acad. Sci. USA* 80:5383–5386 (1983).

Weir, D.M. et al., eds. *Handbook of Experimental Immunololgy*, vols. 1, 2, 3 and 4 (1987) Title page and table of contents only.

Williams, *Concise Encyclopedia of Medical & Dental Materials*, MIT Press: Cambridge, MA (1990) Title page and table of contents only.

Wilson et al., "Biological properties of poliovirus encapsulated in lipid vesicles: Antibody resistance and infectivity in virus-resistant cells" *Proc. Natl. Acad. Sci. USA* 74(8):3471–3475 (1977).

Wilson et al., "Hepatocyte-directed gene transfer in vivo leads to transient improvement of hypercholesterolemia in low density lipoprotein receptor-deficient rabbits" *J. Biol. Chem.* 267(2):963–967 (1992).

Wolf et al., "Transcriptional regulation of prostate kallikrein-like genes by androgen" *Molec. Endocrinol.* 6(5):753–762 (1992).

Yap et al., "Transfer of specific cytotoxic T lymphocyutes protects mice inoculated with influenza virus" *Nature* 273:238–239 (1978).

Young et al., "Tissue–specific and hormonal regulation of human prostate–specific glandular kallikrein" *Biochem* 31(3):818–824 (1992).

Zelenin et al., "Bacterial beta–galactosidase and human dystrophin genes are expressed in mouse skeletal muscle fibers after ballistic transfection" *FEBS Letters* 414:319–322 (1997).

Zenke et al., "Receptor–mediated endocytosis of transferrin–polycation conjugates: An efficient way to introduce DNA into hemotopoietic cells" *Proc. Natl. Acad. Sci. USA* 87:3655–3659 (1990).

Zhou et al., "Liophilic polylysines mediate efficient DNA transfection in mammalian cells" *Biochem. Biophys. Acta* 1065:8–14 (1991).

Zhou et al., "The androgen receptor: An overview" *Recent Prog. Horm. Res.* 49:249–274 (1994).

Zjilstra et al., "Germ–line transmission of a disrupted $beta_2$ microglobuline gene produced by homologous recombination in embryonic stem cells" *Nature* 342:435–438 (1989).

* cited by examiner

| | | |
|---|---|---|
| HKLK2.LA0 | (6998) | AA-CTGAGCCTTGATTATATTG-GAGCTTGGTTGCA-CAG-ACATGTCGA |
| | | :: :: :: : ::: :::: :: : ::: : ::: ::: :: : |
| PSE | ( 509) | AATCT-AG-C-TGA-TATAGTGTG-GCTCAAAACCTTCAGCACAAATC-A |
| | | |
| HKLK2.LA0 | (7044) | CCACCTTCATGGCTGAACTTTAGTACTTAGCCCCTCCAGACGTCTACAGC |
| | | :::: : : : :: : : ::  : : : ::: :: :: ::: |
| PSE | ( 553) | -CACCGTTA-GACT--A-TCTGGT--GT-G--GC-CCAAAC--CTTCAGG |
| | | |
| HKLK2.LA0 | (7094) | TGATAGGCTGTAACCCAACAT-TGTCACCATAAATCACATTGTTAGACTA |
| | | ::: :  : :: : :: :: :: :: : :: ::   :: : |
| PSE | ( 590) | TGA-ACAAAGGGACTCTA-ATCTGGCAGGAT-ATTC-CA----AAG-C-A |
| | | |
| HKLK2.LA0 | (7143) | TCCAGTG-TGGCC-CAAGCTCCCGTGTAAACACAGGCACTCTAAACAG-- |
| | | : :: : :: :: : :: : ::: : : : ::: :: |
| PSE | ( 630) | T-TAGAGATGACCTCTTGC-AAAG-AAAAAGAAATGGAAAAGAAAAAGAA |
| | | |
| HKLK2.LA0 | (7189) | -G-CAGGATATTTCAAAAGCTT-AGAGATGACCTCCCAGGAGCTGAATGC |
| | | : :::: :  :::: :::::::::::: :::: :::: : |
| PSE | ( 677) | AGAAAGGAAAAAAAAAAAAAAAAGAGATGACCTCTCAGGCTCTGAGGGG |
| | | |
| HKLK2.LA0 | (7236) | AAA-GACCTGGCCTCTTTGGGCAAGGAGAATCCTTTACCGCACACTCTCC |
| | | ::: : :::: :::::: :::::: : :::: : ::::: ::::: |
| PSE | ( 727) | AAACG-CCTGAGGTCTTTGAGCAAGGTCAGTCCTCTGTTGCACAGTCTCC |
| | | |
| HKLK2.LA0 | (7285) | TTCACAGGGTTATTGTGAGGATCAAATGTGGTCATGTGTGTGAGACACCA |
| | | :::::::: :::::::: ::::: ::::::::: :::: :::: ::::: |
| PSE | ( 776) | CTCACAGGGTCATTGTGACGATCAAATGTGGTCACGTGTATGAGGCACCA |
| | | : ::: |
| HKLK2.LA0 | (7335) | GCACATGTCTGGCTGTGGAGAGTGACTTCTA--TGTGTGCTAACATTGCT |
| | | :::::: :::::: :::: :: : ::: :::: :: :::: |
| PSE | ( 826) | GCACATGCCTGGCTCTGGGGAGTGCCGTGTAAGTGTATGCTTGCACTGCT |
| | | :: : : :: ::: : : : |
| HKLK2.LA0 | (7383) | GAGTGCTAAGAAAGTATTAGGCATGGCT-TTCAGCACTCACAGATGCTCA |
| | | :: :::: : :: : ::: :: : ::::::::: :::::::::::: |
| PSE | ( 876) | GAATGCTTGGGATGTGTCAGGGAT-TATCTTCAGCACTTACAGATGCTCA |
| | | :: : : : : :: |

FIG. 2A

| | | |
|---|---|---|
| HKLK2.LA0 | (7432) | TCTAATCCTCACAACATGGCTACAGGG-TGGGCACTACTAGCCTCATTTG |
| PSE | ( 925) | TCTCATCCTCACAGCATCACTA-TGGGATGGGTATTACTGGCCTCATTTG |
| HKLK2.LA0 | (7481) | ACAGAGGAAAG-GACTGTGGATAAGAAGGGGGTGACCAATAGGTCAGAGT |
| PSE | ( 974) | ATGGA-GAAAGTGGCTGTGGCTCAGAAAGGGGGGACCACTAGACCAGGGA |
| HKLK2.LA0 | (7530) | CATTCTGGATGCAAGGGG-CTCCAGAGGACCATGATTAGACATTGTCTGC |
| PSE | (1023) | CACTCTGGATGC-TGGGGACTCCAGA-GACCATGACCACTCACCAACTGC |
| HKLK2.LA0 | (7579) | AGAGAAATT----ATGG-CTGGATGTCTCTGCCCCGGAAAGGG-GGA--T |
| PSE | (1071) | AGAGAAATTAATTGTGGCCT-GATGTCCCTGTCCTGGAGAGGGTGGAGGT |
| HKLK2.LA0 | (7621) | GCACTTTCCTTGACCCCCTATCTCAGATCTTGACTTTGAG-GTTATCTCA |
| PSE | (1120) | GGACCTTCACTAACCTCCTACCT-TGACCCTCTCTTTTAGGGCTCTTTCT |
| HKLK2.LA0 | (7670) | GACTTCCTCTATGATACCAGGAGCCCATCATAATCTCTCTGTGTCCTCTC |
| PSE | (1169) | GACCTCCACCATGGTACTAGGA-CCC--CATTGTAT-TCTGT-ACC-CT- |
| HKLK2.LA0 | (7720) | CCCTTCCTCAGTCTTACTG-CCCACTCTTCCCAGCTCCATCTCCAGCTGG |
| PSE | (1212) | --C-T--TGACTC-TA-TGACCCCCACTGCCCA-CTGCA--TCCAGCT-- |
| HKLK2.LA0 | (7769) | CCAGGTGTAGCCACAGTACCTAACTCT-TTGCAGAGAACTATAAATGTGT |
| PSE | (1250) | ---GG-GT--CC-C-CT-CCTATCTCTATT-CCCAG--CTGGCCA-GTGC |
| HKLK2.LA0 | (7818) | A-TCCTACAGGGGAGAAAAAAA-AAAAG-AACTCTGAAAGAGCTGACATT |
| PSE | (1287) | AGT-CT-CAGTGCCCACCTGTTTGTCAGTAACTCTGAAGGGGCTGACATT |
| HKLK2.LA0 | (7865) | TTACCGACTTGCAAACACATAAGCTAACCTGCCAG--TTTTGT----GCT |
| PSE | (1335) | TTACTGACTTGCAAACAAATAAGCTAACTTTCCAGAGTTTTGTGAATGCT |
| HKLK2.LA0 | (7909) | GGTAGAACT-CATGAGACTCCTGGGTCAGAGGCAAAAGATTTTATTACCC |
| PSE | (1385) | GGCAG-AGTCCATGAGACTCCTGAGTCAGAGGCAAAGGCTTTTACTGCTC |

FIG. 2B

```
HKLK2.LA0   (7958)    ACAGCTAAGGAGGCAGCATGAACTTTGTGTTCACATTTGTTCACTTTGCC
                      :::::: :: ::  ::::::::   ::    ::::::::::: ::  ::: :::::
PSE         (1434)    ACAGCTTAGCAGACAGCATGAGGTTCATGTTCACATTAGTACACCTTGCC
                      :              :  ::      :  :: ::     ::                    : :

HKLK2.LA0   (8008)    CCCC--AATTCATAT-GGGATGATCAGAGCAGTTC-AGGTGGATG--G-A
                      ::::    ::  ::   : :   :::   :::::::: ::  ::::::::::  :
PSE         (1484)    CCCCCCAAATCTTGTAGGG-TGACCAGAGCAG-TCTAGGTGGATGCTGTG
                      :           : ::        : :       : :      : :      : :       :

HKLK2.LA0   (8051)    CA-CAGGGGTTTGTGGCAAAGGTGAGCAACCTAG-GCTTAGAAATCCTCA
                      ::  :::::::::::: ::   ::::::   :::::   : :   ::::   ::::::::
PSE         (1532)    CAGAAGGGGTTTGTGCCACTGGTGAGAAACCT-GAGATTAGGAATCCTCA
                      :            : : ::   ::::  :            :   ::          : :

HKLK2.LA0   (8099)    ATCTTATAAGAAGGTACT---AGCAAACTTGTC-CAGTCTTTGTATCTGA
                      :::::::  :    ::  ::      ::::::  ::  :  :::   ::::::: :::::
PSE         (1581)    ATCTTAT-ACTGGG-ACAACTTGCAAACCTG-CTCAGCCTTTGTCTCTGA
                      :  :       :   :   ::       :  ::        :   :::  : : :

HKLK2.LA0   (8145)    CGGAGATATTATCTTTATAAT-TGGG-TTGAAAGCAGACCTACTCTGGAG
                      :  ::::::::::::::   ::  ::  :: ::::::::::::::::::::::::::::
PSE         (1628)    TGAAGATATTATCTTCATGATCTTGGATTGAAAACAGACCTACTCTGGAG
                      :    : :    :: :: ::   :         :   :   : :   ::      :

HKLK2.LA0   (8193)    GAACATATTGTATTTATTGTCCT-GAACAGTAAACAAATCTGCTGTAAAA
                      ::::::::::::::   :::::::   ::::::::: ::::::::::::   ::
PSE         (1678)    GAACATATTGTATCGATTGTCCTTG-ACAGTAAACAAATCTGTTGT--AA
                      :              : ::      :     : :::         :   :::         :

HKLK2.LA0   (8242)    TAGACGTTAACTTTATTATCTAAGG-CAGTAAGCAAACCTAGATCTGAAG
                      ::::  ::: :::::::::::: :::   :::::::::: :::  ::::::  ::
PSE         (1725)    GAGACATTATCTTTATTATCT-AGGACAGTAAGCAAGCCTGGATCTG-AG
                                 :

HKLK2.LA0   (8291)    -GCGATACCATCTTGCAAGGCTATCTGCTGTACAAATATGCTTGAAAAGA
                       : ::::  ::::::::::::::  :    :::::  :::::: ::  :::::::    :
PSE         (1773)    AGAGATATCATCTTGCAAGGATGCCTGCTTTACAAACATCCTTGAAACAA

HKLK2.LA0   (8340)    TGGTCCAGAAAAGAAAACGGTATTATTGCCTTTGCTCAGAAGACACACAG
                      ::::::::: ::::  :::  ::  ::  ::::::::::::::::::::::::::
PSE         (1823)    CAATCCAGAAAA-AAAAAGGTGTTGCTGTCTTTGCTCAGAAGACACACAG

HKLK2.LA0   (8390)    AAACATAAGAGAACCATGGAAAATTGTCTCCCAACACTGTTCACCCAGAG
                      : ::  :  :  :::::::::::::  :::::     :::::::   ::::::   :::::
PSE         (1872)    ATACGTGACAGAACCATGGAGAATTGCCTCCCAACGCTGTTCAGCCAGAG

HKLK2.LA0   (8440)    CCTTCCACTCTTGTCTGCAGGACAGTCTTAACATCCCATCATTAG-T-GT
                      :::::::: :::::::::::::::::::::::::  :::  :  :::::   :  :
PSE         (1922)    CCTTCCACCCTTGTCTGCAGGACAGTCTCAACGTTCCACCATTAAATACT
                                  ::  :::                                   :  ::  ::      ::
```

FIG. 2C

```
HKLK2.LA0   (8488)   --GTCTACCACATCTGGCTTCACCGTGCCTAACCAAGATTTCTAGGTCCA
                     ::::  ::::::  :::::      ::::::::::::   :::::::::::
PSE         (1972)   TCTTCTATCACATCCTGCTTCTTTATGCCTAACCAAG-GTTCTAGGTCCC
                                :     ::    ::    :          ::   ::  :::      :

HKLK2.LA0   (8536)   GTTCCCCACCATGTTTGGCAGTGCCCCACTGCCAACCCCAGAATAAGGGA
                     :  :  :  ::    :::  ::::::   :  ::::::::::: :::::::::::: :
PSE         (2021)   GAT--CGACTGTGTCTGGCAGCACTCCACTGCCAAACCCAGAATAAGGCA
                      ::    :    ::  :      :     ::                    :   :

HKLK2.LA0   (8586)   GTGCTCAGAATTCCGA  (SEQ ID NO: 1, pos. 6998-8602)
                     :  ::::::  ::  ::::
PSE         (2069)   GCGCTCAGGATCCCGA  (SEQ ID NO: 2, pos. 509-2069)
                     :               : :
```

FIG. 2D

|         |       |       | Fold Induction |
|---------|-------|-------|----------------|
| CN379   | -5155 ——————————— -3387 | -324 — | 81 |
| CN386   | ————————— -3529 | — | 50 |
| CN387   | ———————— -3643 | — | 90 |
| CN388   | -4814 ————— -3387 | — | 35 |
| CN389   | ———— -3529 | — | 30 |
| CN390   | ———— -3643 | — | 96 |
| CN391   | -4457 ———— -3387 | — | 61 |
| CN392   | ——— -3529 | — | 53 |
| CN393   | ——— -3643 | — | 30 |
| CN394   | -3993 — -3387 | — | 55 |
| CN395   | — -3529 | — | 45 |
| CN396   | — -3643 | — | 37 |

FIGURE 8

HUMAN GLANDULAR KALLIKREIN ENHANCER, VECTORS COMPRISING THE ENHANCER AND METHODS OF USE THEREOF

CROSS-REFERENCE TO RELATED APPLICATIONS

This application is a continuation of U.S. patent application Ser. No. 09/127,834, now abandoned, filed Aug. 3, 1998, which claims benefit of U.S. Provisional Application Ser. No. 60/054,523, filed Aug. 4, 1997 and U.S. Provisional Application Ser. No. 60/076,545, filed Mar. 2, 1998, all of which are incorporated by reference herein in their entirety.

STATEMENT OF RIGHTS TO INVENTIONS MADE UNDER FEDERALLY SPONSORED RESEARCH (Not Applicable)

TECHNICAL FIELD

This invention relates to novel transcriptional regulatory elements (enhancers) which preferentially increase the transcription of cis-linked transcription units in prostate cells. The invention further relates to methods of using DNA constructs comprising the enhancers to control transcription of heterologous polynucleotides. The invention further relates to cell transfection using adenoviral vectors. More specifically, it relates to cell-specific replication of adenovirus vectors in cells expressing an androgen receptor, particularly prostate carcinoma cells.

BACKGROUND OF THE INVENTION

Prostate cancer is the fastest growing neoplasm in men with an estimated 244,000 new cases in the United States being diagnosed in 1995, of which approximately 44,000 deaths will result. Prostate cancer is now the most frequently diagnosed cancer in men. Prostate cancer is latent; many men carry prostate cancer cells without overt signs of disease. It is associated with a high morbidity. Cancer metastasis to bone (late stage) is common and is almost always fatal.

Current treatments include radical prostatectomy, radiation therapy, hormonal ablation and chemotherapy. Unfortunately, in approximately 80% of cases, diagnosis of prostate cancer is established when the disease has already metastasized to the bones, thus limiting the effectiveness of surgical treatments. A variety of agents are available which are used in androgen blockade therapy and include luteinizing hormone releasing hormone analogs, steroidal antiandrogens such as cyproterone acetate, nonsteroidal antiandrogens such as flutamide, and other agents such as aminoglutethimide and ketoconazole. However, hormonal therapy frequently fails with time with the development of hormone-resistant tumor cells. Although chemotherapeutic agents have been used in the treatment of prostate cancer, no single agent has demonstrated superiority over its counterparts, and no drug combination seems particularly effective. The generally drug-resistant, slow-growing nature of most prostate cancers makes them particularly unresponsive to standard chemotherapy.

A major, indeed the overwhelming, obstacle to cancer therapy is the problem of selectivity; that is, the ability to inhibit the multiplication of tumor cells, while leaving unaffected the function of normal cells. The therapeutic ratio, or ratio of tumor cell killing to normal cell killing of traditional tumor chemotherapy, is only 1.5:1. Thus, more effective treatment methods and pharmaceutical compositions for therapy and prophylaxis of prostatic hyperplasia and neoplasia are needed.

Of particular interest is development of more specific, targeted forms of therapy for prostate diseases. In contrast to conventional cancer therapies, which result in relatively non-specific and often serious toxicity or impotence, more specific treatment modalities attempt to inhibit or kill malignant cells selectively while leaving healthy cells intact.

One possible treatment approach for prostate diseases is gene therapy, whereby a gene of interest is introduced into the malignant cell. Boulikas (1997) Anticancer Res. 17:1471–1505. The gene of interest may encode a protein which converts into a toxic substance upon treatment with another compound, or an enzyme that converts a prodrug to an active drug. For example, introduction of the herpes simplex gene encoding thymidine kinase (HSV-tk) renders cells conditionally sensitive to ganciclovir (GCV). Zjilstra et al. (1989) Nature 342: 435; Mansour et al. (1988) Nature 336: 348; Johnson et al. (1989) Science 245: 1234; Adair et al. (1989) Proc. Natl. Acad. Sci. USA 86: 4574; Capecchi (1989) Science 244: 1288. Alternatively, the gene of interest may encode a compound that is directly toxic, such as diphtheria toxin (DT). For these treatments to be rendered specific to prostate cells, the gene of interest can be under control of a transcriptional regulatory element that specifically (i.e. preferentially) increases transcription of an operably linked polynucleotide in the prostate cells. Cell- or tissue-specific expression can be achieved by using cell-specific enhancers and/or promoters. See generally, Huber et al. (1995) Adv. Drug Delivery Rev. 17:279–292.

A variety of viral and non-viral (e.g., liposomes) vehicles, or vectors, have been developed to transfer these genes. Of the viruses, retroviruses, herpes virus, adeno-associated virus, Sindbis virus, poxvirus and adenoviruses have been proposed for use in gene transfer, with retrovirus vectors or adenovirus vectors being the focus of much current research. Verma and Somia (1997) Nature 389:239–242.

Adenoviruses are among the most easily produced and purified, and furthermore do not integrate into the host genome, reducing the possibility of dangerous mutations. Moreover, adenovirus has the advantage of effecting high efficiency of transduction and does not require cell proliferation for efficient transduction of cell. For general background references regarding adenovirus and development of adenoviral vector systems, see Graham et al. (1973) Virology 52:456–467; Takiff et al. (1981) Lancet 11:832–834; Berkner et al. (1983) Nucleic Acid Research 11: 6003–6020; Graham (1984) EMBO J 3:2917–2922; Bett et al. (1993) J. Virology 67:5911–5921; and Bett et al. (1994) Proc. Natl. Acad. Sci. USA 91:8802–8806.

When used as gene transfer vehicles, adenovirus vectors are often designed to be replication-defective and are thus deliberately engineered to fail to replicate in the target cells of interest. In these vehicles, the early adenovirus gene products E1A and/or E1B are deleted and provided in trans by the packaging cell line 293. Graham et al. (1987) J. Gen. Virol 36:59–72; Graham (1977) J. Genetic Virology 68:937–940. The gene to be transduced is commonly inserted into adenovirus in the deleted E1A and E1B region of the virus genome. Bett et al. (1994). Replication-defective adenovirus vectors as vehicles for efficient transduction of genes have been described by, inter alia, Stratford-Perricaudet (1990) Human Gene Therapy 1:241–256; Rosenfeld (1991) Science 252:431–434; Wang et al. (1991)

Adv. Exp. Med. Biol. 309:61–66; Jaffe et al. (1992) Nat. Genet. 1:372–378; Quantin et al. (1992) Proc. Natl. Acad. Sci. USA 89:2581–2584; Rosenfeld et al. (1992) Cell 68:143–155; Stratford-Perricaudet et al. (1992) J. Clin. Invest. 90:626–630; Le Gal Le Salle et al. (1993) Science 259:988–990 Mastrangeli et al. (1993) J. Clin. Invest. 91:225–234; Ragot et al. (1993) Nature 361:647–650; Hayaski et al. (1994) J. Biol. Chem. 269:23872–23875; and Bett et al. (1994).

The virtually exclusive focus in the development of adenoviral vectors for gene therapy is use of adenovirus merely as a vehicle for introducing the gene of interest, not as an effector in itself. Replication of adenovirus has been viewed as an undesirable result, largely due to the host immune response. In the treatment of cancer by replication-defective adenoviruses, the host immune response limits the duration of repeat doses at two levels. First, the capsid proteins of the adenovirus delivery vehicle itself are immunogenic. Second, viral late genes are frequently expressed in transduced cells, eliciting cellular immunity. Thus, the ability to administer repeatedly cytokines, tumor suppressor genes, ribozymes, suicide genes, or genes which convert a prodrug to an active drug has been limited by the immunogenicity of both the gene transfer vehicle and the viral gene products of the transfer vehicle as well as the transient nature of gene expression. There is a need for vector constructs that are capable of eliminating cancerous cells in a minimum number of administrations before specific immunological response against the vector prevents further treatment.

Human Glandular Kallikrein

Prostate-specific antigen (PSA or hKLK3) and human pancreatic/renal kallikrein are two members of a subgroup of serine proteases that are potentially involved in the activation of specific polypeptides throughout post-translational processing. Clements (1989) Endocr. Rev. 10:393–419. PSA is synthesized exclusively by normal, hyperplastic, and malignant prostatic epithelia; hence, its tissue-specific expression has made it an excellent biomarker for benign prostatic hyperplasia (BPH) and prostatic carcinoma (CaP). Normal serum levels of PSA are typically below 5 ng/ml, with elevated levels indicative of BPH or CaP.

A third member of the kallikrein gene family, human glandular kallikrein-1 (hGK-1 or hKLK2, encoding the hK2 protein), shares a number of characteristics with PSA. First, both are expressed exclusively in the prostate and are up-regulated by androgens primarily by transcriptional activation. Wolf et al. (1992) Molec. Endocrinol. 6:753–762. Morris (1989) Clin. Exp. Pharm. Physiol. 16:345–351; Qui et al. (1990) J. Urol. 144:1550–1556; Young et al. (1992) Biochem. 31:818–824. Second, hKLK2 and PSA mRNAs are synthesized and co-localize only in prostatic epithelia. Third, hK2 and PSA exhibit a high degree of amino acid sequence identity. Schedlich et al. (1987) DNA 6:429–437. Fourth, they have similar regulatory elements. There is approximately 80% nucleotide sequence identity between PSA and hKLK2 in the 5'-flanking region from −300 to −1 relative to the transcription initiation site. Young et al. (1992) Biochem. 31:818–824. Each promoter contains an androgen responsive element (ARE); their respective ARE's differ from one another by only 1 nucleotide. Schedlich et al. (1987) DNA 6:429–437; Murtha et al. (1993) Biochem. 32:6459–6464.

The levels of hK2 found in various tumors and in the serum of patients with prostate cancer differ substantially from those of PSA. Circulating hK2 in different relative proportions to PSA has been detected in the serum of patients with prostate cancer. Charlesworth et al. (1997) Urology 49:487–493. Expression of hK2 has been detected in each of 257 radical prostatectomy specimens analyzed. Darson et al. (1997) Urology 49:857–862. The intensity and extent of hK2 expression, detected using specific antibodies, increased from benign epithelium to high-grade prostatic intraepithelial neoplasia (PIN) and adenocarcinoma, whereas PSA and prostate acid phosphatase (PAP) displayed an inverse pattern of immunoreactivity. Darson et al. (1997) Urology 49:857–862. Indeed, it has been reported that a certain percentage of PSA-negative tumors have detectable hK2. Tremblay et al. (1997) Am. J. Pathol. 150:455–459.

The hKLK2 promoter is inducible by androgen, consistent with the presence in the promoter of an ARE. Murtha et al. (1993). However, the promoter region of approximately 627 base pairs of the 5' flanking region of the hKLK2 gene, which was linked to a reporter gene in a plasmid construct and introduced into cells, responded with only an approximately 10-fold increase in reporter gene activity when androgen was added to the culture medium. Murtha et al. (1993).

Androgen induction of gene expression requires the presence of an androgen receptor (AR). Typically, an androgen diffuses passively into the cell where it binds AR. The androgen-activated AR binds to specific DNA sequences called androgen-responsive elements (AREs or ARE sites). Once anchored to an ARE, the AR is able to regulate transcriptional activity in either a positive or negative fashion. Lindzey et al. (1994) Vitamins and Hormones 49: 383–432.

The AR belongs to a nuclear receptor superfamily whose members are believed to function primarily as transcription factors that regulate gene activity through binding to specific DNA sequences, hormone-responsive elements. Carson-Jurica et al. (1990) Endocr. Rev. 11: 201–220. This family includes the other steroid hormone receptors as well as the thyroid hormone, the retinoic acid and the vitamin $D_3$ receptors. The progesterone and glucocorticoid receptor are structurally most closely related to the AR. Tilley et al. (1989) Proc. Natl. Acad. Sci. USA 86: 327–331; Zhou et al. (1994) Recent Prog. Horm. Res. 49: 249–274; and Lindzey et al. (1994) Vitamins and Hormones 49: 383–432.

The AR gene itself is a target of androgenic regulation. In the prostate cancer cells lines PC3 and DU145, which do not express an endogenous AR, androgenic up-regulation of AR cDNA expression occurred in the transfected cells. Dai et al. (1996) Steroids 61:531–539. Androgenic up-regulation of AR mRNA and protein was observed in PC3 cells that were stably transfected with the AR cDNA, suggesting that AR mRNA regulation also occurs when the cDNA is organized into chromatin. Dai et al. (1996).

Identification of prostate-specific genes and the transcription regulatory elements that control their expression would facilitate the development of strategies to combat prostate cancer by providing targets for therapy. The development of novel therapeutic approaches to the treatment of prostate cancer is critical, since these diseases are generally recalcitrant to conventional therapies.

SUMMARY OF THE INVENTION

The present invention provides a prostate-specific gene enhancer which regulates expression of the human glandular kallikrein (hKLK2) gene. An hKLK2 enhancer can form part of an hKLK2 transcriptional regulatory element (hKLK2-TRE). An hKLK2-TRE in turn can be operably linked a heterologous polynucleotide to effect transcriptional control of the linked gene.

Accordingly, the invention provides an isolated polynucleotide comprising 150 contiguous nucleotides of nucleotides 1 to 11,407 of SEQ ID NO:1 (but not depicted in SEQ ID NO:2 or SEQ ID NO:3), and having enhancer activity. In another aspect, the invention provides an isolated polynucleotide comprising 150 contiguous nucleotides having at least about 70% sequence identity to a sequence within nucleotides 1 to 11,407 of SEQ ID NO:1 (but not depicted in SEQ ID NO:2 or SEQ ID NO:3), with the polynucleotide having enhancer activity.

In another aspect, the invention provides an isolated polynucleotide comprising at least about 15 nucleotides which hybridize under stringent conditions to a polynucleotide comprising nucleotides 1 to 11,407 of SEQ ID NO:1 or a complement thereof, wherein the at least about 15 nucleotides are not depicted in SEQ ID NO:2 or SEQ ID NO:3). In various embodiments, the portions are nucleotides about 8021 to about 8371, about 7200 to about 8371, about 6859 to about 8627, about 5986 to about 9620, about 1 to about 9765, about 1 to about 11,407 of SEQ ID NO:1.

In another aspect, the invention provides isolated polynucleotides comprising portions of nucleotides 1 to 11,407 of SEQ ID NO:1, wherein the portions have enhancer activity.

In another aspect, the invention provides an isolated polynucleotide comprising a transcriptional regulatory element which comprises an hKLK2 enhancer and a promoter.

The invention also provides vectors and/or delivery vehicles containing these enhancer polynucleotide(s). Such vectors and/or delivery vehicles can be introduced into cells both in vivo and in vitro.

An hKLK2-TRE can be incorporated into an adenoviral vector, which can be so constructed that an hKLK2-TRE controls expression of at least one adenoviral gene and/or at least one transgene. Preferably, the adenoviral gene is one that contributes to cytotoxicity, such as a gene that is required for adenoviral replication, or that encodes an adenoviral death protein. Accordingly, the present invention further provides adenoviral vectors in which an adenovirus gene is under transcriptional control of a human glandular kallikrein (hKLK2) transcription regulatory element, wherein the hKLK2 transcription regulatory element comprises an hKLK2 enhancer and a promoter. Alternatively an adenoviral vector can be constructed such that an hKLK2-TRE controls expression of an adenoviral gene or genes, and, in addition, a heterologous polynucleotide is under transcriptional control of an hKLK2-TRE. Accordingly, the present invention further provides adenoviral vectors containing heterologous polynucleotides which are transcribed preferentially in cells which allow an hKLK2 enhancer and/or an hKLK2-TRE to function.

In another aspect, the invention provides an adenovirus vector comprising a first gene, such as an adenoviral gene or a transgene, under transcriptional control of a human glandular kallikrein (hKLK2) transcription regulatory element (hKLK2-TRE) and at least one other gene, such as an adenoviral gene or a transgene, under transcriptional control of a prostate specific antigen (PSA) transcription regulatory element (PSA-TRE), wherein said hKLK2-TRE comprises an hKLK2 enhancer and a promoter and wherein said PSA-TRE comprises a prostate specific enhancer (PSE) and a promoter.

The invention also provides methods for introducing into a cell a vector and/or a delivery vehicle containing an hKLK2 enhancer. The invention further provides host cells containing an hKLK2 enhancer polynucleotide.

In other aspects, the invention provides methods of creating constructs comprising an hKLK2-TRE operably linked to a heterologous polynucleotide and further provides methods for increasing the transcription and/or expression of the linked heterologous polynucleotide generally involving introducing the constructs into suitable cells.

Accordingly, the invention provides methods for increasing transcription of an operably linked polynucleotide sequence in a cell comprising introducing a construct comprising a human glandular kallikrein (hKLK2) enhancer and a promoter operably linked to said polynucleotide into a cell in which said hKLK2 enhancer and/or an hKLK2-TRE is functional.

Further provided are methods of using the adenoviral vectors of the invention. In one aspect, methods are provided for using the adenovirus vectors described herein which entail introducing these vector(s) into a cell. In another aspect, methods are provided for conferring selective cytoxicity on a cell which allows an hKLK2 enhancer and/or an hKLK2-TRE to function that entail contacting the cells with an adenovirus vector described herein, wherein the adenovirus vector enters the cell. In another aspect, methods are provided for modifying the genotype of a target cell, comprising contacting the cell with an adenovirus vector described herein, wherein the adenovirus vector enters the cell. In yet another aspect, methods are provided for propagating the adenovirus vectors of the invention, comprising combining the adenovirus vectors with cells which allow an hKLK2 enhancer and/or an hKLK2-TRE to function, such that the adenovirus vector enters the cell and is propagated.

In another aspect, the invention provides a method for screening compounds for the treatment of prostate cancer employing cells comprising an expression construct, said expression construct comprising an hKLK2-TRE and a reporter gene whose expression product provides a detectable signal, wherein said reporter gene is under the transcriptional control of said hKLK2-TRE, said method comprising the steps of combining said cells with a candidate compound and an appropriate inducing agent for a sufficient time for detectable expression of said reporter gene, and detecting the level of expression of said reporter gene as compared to the level of expression in the absence of said candidate compound.

BRIEF DESCRIPTION OF THE DRAWINGS

FIGS. 2A to 2D show a nucleotide sequence alignment of a 2227 nucleotide portion of an hKLK2 enhancer (nucleotides 7272 to 9498 of SEQ ID NO:1) and a 2187 nucleotide portion of a PSE (nucleotides 775 to 2961 of the sequence given in GenBank Accession No. U37672). The upper line is nucleotides 7272 to 9498 of SEQ ID NO:1. The lower line is nucleotides 775 to 2961 of GenBank Accession No. U37672. Dots between the lines indicate identity. Gaps introduced to maximize identity are indicated by dashes. Parameters for alignment were: mismatch=2; open gap=0; and extend gap=2.

FIG. 3A shows induction, expressed in relative light units (RLU) per μg total protein, of luciferase expression by the hKLK2 promoter-containing construct CN299 (stippled bars) or by the hKLK2 promoter/enhancer-containing construct CN322 (solid bars) in the presence of 0 nM or 0.5 nM R1881. FIG. 3B shows the fold induction calculated by comparing CN322 RLU/μg protein with CN299 RLU/μg protein in the presence of 0.5 nM R1881.

FIG. 4A shows luciferase activity, expressed as RLU/μg protein, from cultures incubated in the presence of 0, 0.01, 0.1, 1, or 10 nM R1881. FIG. 4B shows fold induction calculated by comparing RLU/μg protein at a given concentration to RLU/μg protein at 0 nM R1881.

FIG. 8 is a schematic representation of hKLK2 enhancer/promoter constructs. Expression plasmids were constructed in which luciferase gene expression is driven by hKLK2 enhancer fragments of various lengths, linked to the hKLK2 minimal promoter (−324 to +33 relative to the transcription start site). Numbers above the lines depicting the constructs give 5' and 3' ends, relative to the transcription start site, of the enhancer fragments. In the right-hand column, values are given for fold induction over control samples to which no inducer was added.

FIG. 25A: Lane 1, probe alone; Lane 2, probe with LNCaP extract; Lane 3, probe with LNCaP extract and specific DNA competitor; Lane 4, probe with LNCaP extract and mock competitor; Lane 5, mock competitor probe with LNCaP extract; Lane 6, mock competitor probe alone. FIG. 25B. Lane 1, probe alone; Lane 2, probe with LNCaP extract; Lane 3, probe with LNCaP extract and specific DNA competitor; Lane 4, probe with HeLa extract; Lane 5, probe with HeLa extract and specific DNA competitor. Arrows indicate the DNA-protein complex observed with LNCaP extracts but not with HeLa extracts.

MODES FOR CARRYING OUT THE INVENTION

We have isolated and characterized a transcriptional enhancer which regulates, in a tissue-specific manner, the expression of human glandular kallikrein (hKLK2). The activity of the hKLK2 5' promoter has been previously described and a region up to −2256 relative to the transcription start site was previously disclosed. Schedlich et al. (1987). The hKLK2 promoter is androgen responsive and, in plasmid constructs wherein the promoter alone controls the expression of a reporter gene, expression of the reporter gene is increased approximately 10-fold in the presence of androgen. Murtha et al. (1993). An hKLK2 enhancer of the present invention, when operably linked to an hKLK2 promoter and a reporter gene, increases transcription of cis-linked sequences in prostate cells in the presence of androgen at levels approximately 30- to approximately 100-fold over the level of transcription in the absence of androgen. This induction is generally orientation independent and position independent.

Figure 10:
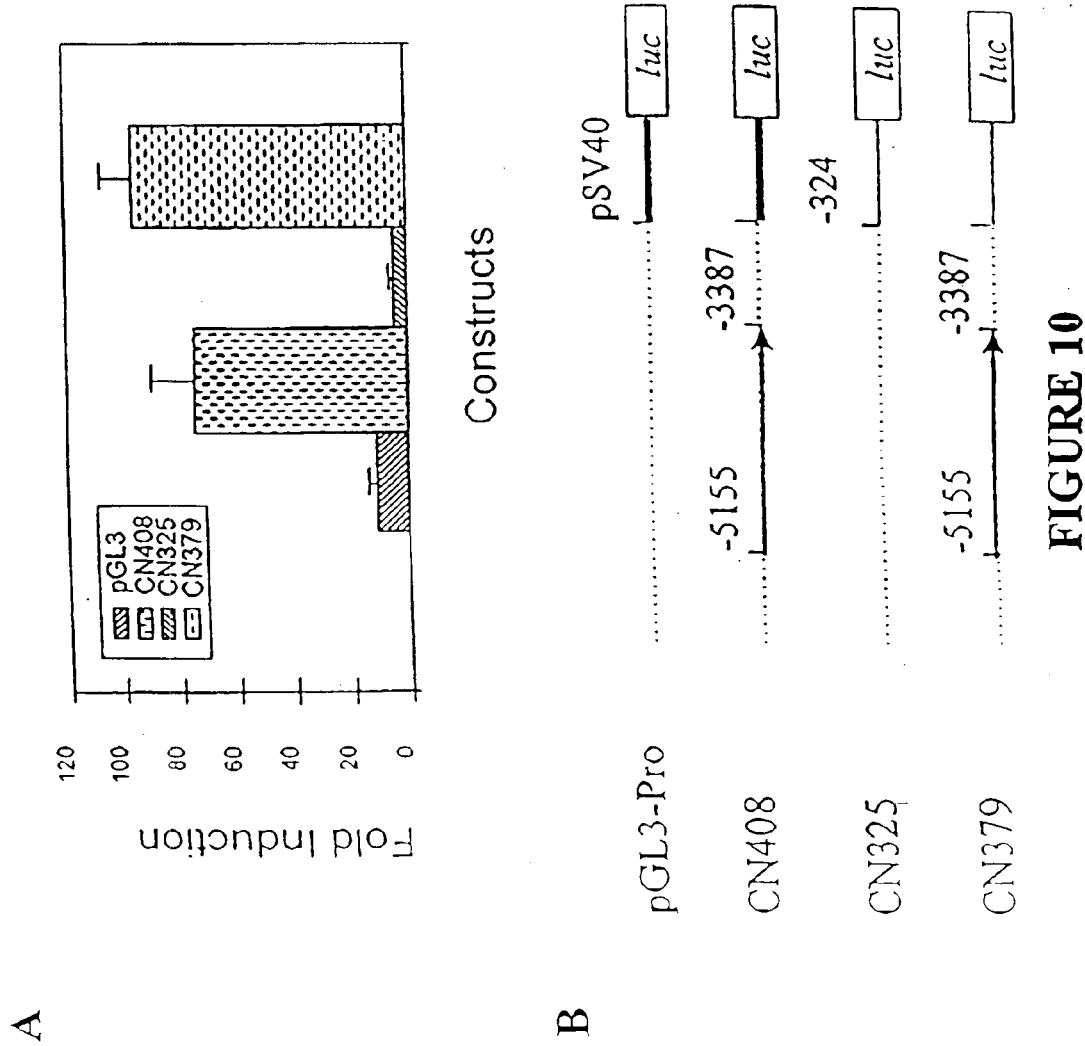
FIG. 10A is a bar graph depicting the activity of an hKLK2 enhancer operably linked to an hKLK2 promoter (CN379), or to an SV40 promoter (CN408), to drive expression of luciferase gene. The constructs are shown schematically in FIG. 10B. LNCaP cells were transfected with the constructs and enhancer activity was measured as described in Example 3.

As shown in FIG. 10 and Table 1, when an hKLK2-TRE, comprising an hKLK2 enhancer comprising nucleotides 6859 to 8627 of SEQ ID NO:1 and an SV40 promoter, operably linked to a reporter gene is introduced into LNCaP cells, upon induction with R1881, reporter gene expression is induced about 80-fold.

Thus, an hKLK2 enhancer can be operably linked to an hKLK2 promoter or a heterologous promoter to form an hKLK2 transcriptional regulatory element (hKLK2-TRE). An hKLK2-TRE can then be operably linked to a heterologous polynucleotide to confer hKLK2-TRE-specific transcriptional regulation on the linked gene, thus increasing its expression. Such constructs can then be introduced into cells. An hKLK2 enhancer polynucleotide, which may be part of an hKLK2-TRE, can be inserted into a viral or a non-viral vector, and delivered to a cell by a variety of delivery vehicles, including non-viral and viral delivery vehicles. In those cells which allow an hKLK2-TRE to function in increasing expression, the heterologous polynucleotide will be expressed at a level higher than in those cells which do not allow an hKLK2-TRE to function.

An hKLK2-TRE is useful for effecting cell-specific expression, for example, in cells of the prostate, thus enabling the directed expression of a desired gene in these cells. For example, vector constructs comprising a heterologous polynucleotide under the transcriptional control of an hKLK2-TRE can be introduced into prostate cancer cells wherein the heterologous polynucleotide encodes a product which is inhibitory to cell growth, thus controlling the growth of the cancerous cells.

We have also discovered and constructed replication-competent adenovirus vectors containing an hKLK2-TRE which can preferentially replicate in cells, such as prostate cells, that allow function of an hKLK2 enhancer and/or an hKLK2-TRE, and developed methods using these adenovirus vectors. The adenovirus vectors of this invention comprise at least one adenovirus gene, preferably at least one adenoviral gene which contributes to cytotoxicity, under the transcriptional control of an hKLK2-TRE. By providing for cell-specific transcription of at least one adenovirus gene required for replication, the invention provides adenovirus vectors that can be used for specific cytotoxic effects due to selective replication. This is especially useful in the cancer context, in which targeted cell killing is desirable. The adenovirus vectors are useful for treatment of cancers such as prostate. The vectors can also be useful for detecting the presence of androgen receptor-producing cells in, for example, an appropriate biological (such as clinical) sample. Further, the adenovirus vector(s) can optionally selectively produce one or more proteins of interest in a target cell by using an hKLK2-TRE.

The adenovirus vectors of the invention replicate preferentially in cells in which an hKLK2 enhancer and/or an hKLK2-TRE is functional, for example, prostate cells. This replication preference is indicated by comparing the level of replication (i.e., titer) in cells in which an hKLK2 enhancer and/or an hKLK2-TRE is functional to the level of replication in cells in which an hKLK2 enhancer and/or an hKLK2-TRE is not functional. The replication preference is even more significant, as the adenovirus vectors of the invention actually replicate at a significantly lower rate in cells in which an hKLK2 enhancer and/or an hKLK2-TRE is not functional than wild type virus. Comparison of the titer in cells in which an hKLK2 enhancer and/or an hKLK2-TRE is functional to the titer in cells in which an hKLK2 enhancer and/or an hKLK2-TRE is not functional provides a key indication that the overall replication preference is enhanced due to depressed replication in cells in which an hKLK2 enhancer and/or an hKLK2-TRE is not functional as well as the replication in cells in which an hKLK2 enhancer and/or an hKLK2-TRE is functional when compared to wild type adenovirus. Thus, the invention uses and takes advantage of what has been considered an undesirable aspect of adenoviral vectors, namely, their replication and possible concomitant immunogenicity. Runaway infection is prevented due to the cell-specific requirements for viral replication. Without wishing to be bound by any particular theory, the inventors note that production of adenovirus proteins can serve to activate and/or stimulate the immune system, either generally or specifically toward target cells producing adenoviral proteins which can be an important consideration in the cancer context, where patients are often moderately to severely immunocompromised.

Cells in which an hKLK2 enhancer and/or an hKLK2-TRE function to increase expression of a heterologous polynucleotide can be used to screen compounds for possible therapeutic effect against prostate cancer. Accordingly, methods are provided for screening compounds which comprise adding the compound to cells in which an hKLK2-TRE functions to increase expression of a heterologous polynucleotide, which provides for a detectable, quantifiable signal. By measuring the effect of the candidate compound on the level of signal observed as compared to a basal level (i.e., no candidate compound added), one can evaluate the potential of the compound as a therapeutic agent for the treatment of prostate cancer. Suitable candidate compounds are discussed below. Particularly, anti-androgenic activity can be evaluated as indicative of therapeutic effects for prostate cancer, although any compound which modifies the expression of a prostate-specific gene, whatever its mode of action, may be considered a candidate compound.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

For techniques related to adenovirus, see, inter alia, Felgner and Ringold (1989) Nature 337:387–388; Berkner and Sharp (1983) Nucl. Acids Res. 11:6003–6020; Graham (1984) EMBO J. 3:2917–2922; Bett et al. (1993) J. Virology 67:5911–5921; Bett et al. (1994) Proc. Natl. Acad. Sci. USA 91:8802–8806.

Definitions

As used herein, an "hKLK2 enhancer" is a polynucleotide sequence derived from the hKLK2 gene which has enhancer activity. Having "enhancer activity" is a term well understood in the art and means what has been stated, i.e., it increases transcription of a gene which is operably linked to a promoter to an extent which is greater than the increase in transcription effected by the promoter itself when operably linked to the gene, i.e., it increases transcription from the promoter.

One of ordinary skill in the art would readily appreciate that changes may be made to the nucleotide sequence of the hKLK2 enhancer without affecting its function. Such changes are encompassed in the term "hKLK2 enhancer". Preferably an hKLK2 enhancer sequence bears at least about at least about 70%, more preferably at least about 75%, more preferably at least about 80%, more preferably at least about 85%, more preferably at least about 90%, more preferably at least about 95%, more preferably at least about 98%, more preferably at least about 99% and even more preferably 100% nucleotide sequence identity to a nucleotide sequence within nucleotides 1 to 11,407 of SEQ ID NO:1, preferably nucleotides about 1 to about 9765 of SEQ ID NO:1, more preferably nucleotides about 5976 to about 9620 of SEQ ID NO:1, more preferably nucleotides about 6859 to about 8627 of SEQ ID NO:1, more preferably nucleotides about 7200 to about 8371 to SEQ ID NO:1, even more preferably nucleotides about 8021 to about 8371 of SEQ ID NO:1. Changes to the nucleotide sequence of the hKLK2 enhancer or active fragments thereof are acceptable as long as enhancer function is maintained. As discussed herein, it is understood that hKLK2 sequences described herein are not found in (i.e., depicted in) SEQ ID NO:2 or SEQ ID NO:3.

As used herein, a "human glandular kallikrein gene transcription response element or transcriptional regulatory element", or "hKLK2-TRE" is a polynucleotide sequence, preferably a DNA sequence, which increases transcription of an operably linked polynucleotide sequence in a host cell that allows an hKLK2-TRE to function. An hKLK2-TRE comprises an hKLK2 enhancer and a promoter. As discussed below, the promoter may or may not be heterologous. Methods are described herein for measuring the activity of an hKLK2-TRE and thus for determining whether a given cell allows an hKLK2-TRE to function.

A "functionally-preserved" variant of an hKLK2-TRE is an hKLK2-TRE which differs from another hKLK2-TRE, but which still retains ability to increase transcription of an operably linked polynucleotide. The difference in an hKLK2-TRE can be due to differences in linear sequence, arising from, for example, single or multiple base mutation(s), addition(s), deletion(s), insertion(s), and/or modification(s) of the bases. The difference can also arise from changes in the sugar(s), and/or linkage(s) between the bases of an hKLK2-TRE.

A "heterologous" promoter or enhancer is one which is not normally associated in a cell with or derived from an hKLK2 gene. Examples of a heterologous promoter or enhancer are the albumin promoter or enhancer and other viral promoters and enhancers, such as SV40.

In the context of an hKLK2-TRE, a "heterologous polynucleotide" is defined in relation to a reference gene sequence. For example, a heterologous polynucleotide with respect to an hKLK2 promoter or an hKLK2 enhancer is a gene that is not naturally operably linked to an hKLK2 promoter or an hKLK2 enhancer. As used herein, "heterologous polynucleotide" refers to a heterologous coding sequence. A heterologous coding sequence may encode a protein. Alternatively, a "heterologous polynucleotide" may be transcribed into an RNA, for example, an antisense RNA or a ribozyme.

The term "operably linked" relates to the orientation of polynucleotide elements in a functional relationship. A TRE is operably linked to a coding segment if the TRE promotes transcription of the coding sequence. Operably linked means that the DNA sequences being linked are generally contiguous and, where necessary to join two protein coding regions, contiguous and in the same reading frame. However, since enhancers generally function when separated from the promoter by several kilobases and intronic sequences may be of variable length, some polynucleotide elements may be operably linked but not contiguous.

A sequence, whether polynucleotide or polypeptide, "depicted in" a SEQ ID NO, means that the sequence is present as an identical contiguous sequence in the sequence of the SEQ ID NO. Conversely, a contiguous sequence that is "not depicted in" a SEQ ID NO means that the contiguous sequence is not present as an identical contiguous sequence in the sequence of the SEQ ID NO.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH2) or a mixed phosphoramidate-phosphodiester oligomer. Peyrottes et al. (1996) *Nucleic Acids Res.* 24: 1841–8; Chaturvedi et al. (1996) *Nucleic Acids Res.* 24: 2318–23; Schultz et al. (1996) *Nucleic Acids Res.* 24: 2966–73. A phosphorothiate linkage can be used in place of a phosphodiester linkage. Braun et al. (1988) *J. Immunol.* 141: 2084–9; Latimer et al. (1995) *Mol. Immunol.* 32: 1057–1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

A polynucleotide or polynucleotide region has a certain percentage (for example, 80%, 85%, 90%, or 95%) of "sequence identity" to another sequence means that, when aligned, that percentage of bases are the same in comparing the two sequences. This alignment and the percent homology or sequence identity can be determined using software programs known in the art, for example those described in *Current Protocols in Molecular Biology* (F. M. Ausubel et al., eds., 1987) Supplement 30, section 7.7.18, Table 7.7.1. A preferred alignment program is ALIGN Plus (Scientific and Educational Software, Pennsylvania).

An "isolated" or "purified" polynucleotide is one that is substantially free of the materials with which it is associated in nature. By substantially free is meant at least 50%, preferably at least 70%, more preferably at least 80%, and even more preferably at least 90% free of the materials with which it is associated in nature. As used herein, an "isolated" polynucleotide also refers to recombinant polynucleotides or polypeptides, which, by virtue of origin or manipulation: (1) are not associated with all or a portion of a polynucleotide or polypeptide with which it is associated in nature, (2) are linked to a polynucleotide or polypeptide other than that to which it is linked in nature, or (3) does not occur in nature.

As used herein, "a cell which allows an hKLK2 enhancer and/or an hKLK2-TRE to function" or a cell in which the function of an hKLK2 enhancer and/or an hKLK2-TRE is "sufficiently preserved", or "a cell in which an hKLK2 enhancer and/or an hKLK2-TRE is functional" is a cell in which an hKLK2 enhancer and/or an hKLK2-TRE, when operably linked to a promoter and a reporter gene, increases expression of the reporter gene at least about 2-fold, preferably at least about 5-fold, preferably at least about 10-fold, more preferably at least about 20-fold, more preferably at least about 50-fold, more preferably at least about 100-fold, more preferably at least about 200-fold, even more preferably at least about 400- to about 500-fold, even more preferably at least about 1000-fold, when compared to the expression of the same promoter and reporter gene when not operably linked to an hKLK2 enhancer. Methods for measuring levels (whether relative or absolute) of expression are known in the art and are described herein.

A "host cell" includes an individual cell or cell culture which can be or has been a recipient of any polynucleotide (s) and/or vector(s) of this invention. Host cells include progeny of a single host cell, and the progeny may not necessarily be completely identical (in morphology or of total DNA complement) to the original parent cell due to natural, accidental, or deliberate mutation and/or change. A host cell includes cells transfected or infected in vivo with a polynucleotide and/or a vector of this invention.

As used herein, a "target cell" is one which allows an hKLK2 enhancer and/or an hKLK2-TRE to function. Preferably, a target cell is a mammalian cell, preferably a mammalian cell expressing androgen receptor, more preferably, a mammalian cell expressing endogenous androgen receptor, more preferably a human cell, and more preferably a human cell expressing an androgen receptor.

As used herein, the terms "neoplastic cells", "neoplasia", "tumor", "tumor cells", "cancer" and "cancer cells", (used interchangeably) refer to cells which exhibit relatively autonomous growth, so that they exhibit an aberrant growth phenotype characterized by a significant loss of control of cell proliferation. Neoplastic cells can be malignant or benign.

The terms "vector", "polynucleotide vector", "construct" and "polynucleotide construct" are used interchangeably herein. A polynucleotide vector of this invention may be in any of several forms, including, but not limited to, RNA, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, complexed with compounds such as PEG to immunologically "mask" the molecule and/or increase half-life, or conjugated to a non-viral protein. A polynucleotide vector of this invention may be in the form of any of the delivery vehicles described herein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

An "adenovirus vector" or "adenoviral vector" (used interchangeably) is a term well understood in the art and generally comprises a polynucleotide (defined herein) comprising all or a portion of an adenovirus genome. For the purposes of the present invention, an adenovirus vector contains an hKLK2-TRE operably linked to a polynucleotide. The operably linked polynucleotide can be adenoviral or heterologous. An adenoviral vector of the present invention can be in any of several forms, including, but not limited to, naked DNA; an adenoviral vector encapsulated in an adenovirus coat; packaged in another viral or viral-like form (such as herpes simplex virus and AAV); encapsulated in a liposome; complexed with polylysine or other biocompatible polymer; complexed with synthetic polycationic molecules; conjugated with transferrin; complexed with compounds such as PEG to immunologically "mask" the molecule and/or increase half-life, or conjugated to a non-viral protein. An adenoviral vector of this invention may be in the form, of any of the delivery vehicles described herein. Such vectors are one embodiment of the invention. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. For purposes of this invention, adenovirus vectors are replication-competent in a target cell.

In the context of adenovirus vector(s), a "heterologous polynucleotide" or "transgene" is any gene that is not present in wild-type adenovirus. Preferably, the transgene will also not be expressed or present in the target cell prior to introduction by the adenovirus vector. Examples of preferred transgenes are provided below.

In the context of a viral vector, e.g., adenovirus vector(s), of the invention, a "heterologous" promoter or enhancer is one which is not present in wild-type virus. Examples of a heterologous promoter or enhancer are the albumin promoter or enhancer and other viral promoters and enhancers, such as SV40.

In the context of adenovirus vector(s), an "endogenous" promoter, enhancer, or TRE is native to or derived from adenovirus.

As used herein, the terms "agent", "test compound", and "candidate compound" are used interchangeably and mean a biological or chemical compound such as a simple or complex organic or inorganic molecule, a peptide, a protein or an oligonucleotide. A vast array of compounds can be synthesized, for example oligomers, such as oligopeptides and oligonucleotides, and synthetic inorganic and organic compounds based on various core structures, and these are also included in the term "agent". In addition, various natural sources can provide compounds for screening, such as plant or animal extracts, and the like. "Under transcriptional control" is a term well-understood in the art and indicates that transcription of a polynucleotide sequence, usually a DNA sequence, depends on its being operably (operatively) linked to an element which contributes to the unification of, or promotes transcription. "Androgen receptor" as used herein refers to a protein whose function is to specifically bind to androgen and, as a consequence of the specific binding, recognize and bind to an androgen response element (ARE), following which the AR is capable of regulating transcriptional activity. The AR is a nuclear receptor that, when activated, binds to cellular androgen-responsive element(s). In normal cells the AR is activated by androgen, but in non-normal cells (including malignant cells) the AR may be activated by non-androgenic agents, including hormones other than androgens. Encompassed in the term "androgen receptor" are mutant forms of an androgen receptor, as long as the function is sufficiently preserved. Mutants include androgen receptors with amino acid additions, insertions, truncations and deletions, as long as the function is sufficiently preserved. In this context, a functional androgen receptor is one that binds both androgen and, upon androgen binding, an ARE.

As used herein, "cytotoxicity" is a term well understood in the art and refers to a state in which one or more of a cell's usual biochemical or biological functions are aberrantly compromised (i.e., inhibited or elevated). These activities include, but are not limited to, metabolism; cellular replication; DNA replication; transcription; translation; uptake of molecules. "Cytotoxicity" includes cell death and/or cytolysis. Assays are known in the art which indicate cytotoxicity, such as dye exclusion, $^3$H-thymidine uptake, and plaque assays. The term "selective cytotoxicity", as used herein, refers to the cytotoxicity conferred by a polynucleotide vector of the present invention on a cell which allows an hKLK2 enhancer to function when compared to the cytotoxicity conferred by a polynucleotide vector of the present invention on a cell which does not allow an hKLK2 enhancer to function. Such cytotoxicity may be measured, for example, by plaque assays, by reduction or stablization in size of a tumor comprising target cells, or the reduction or stabilization of serum levels of a marker characteristic of the tumor cells, or a tissue-specific marker, e.g., a cancer marker, such as prostate specific antigen.

"Replication" and "propagation" are used interchangeably and refer to the ability of a adenovirus vector of the invention to reproduce or proliferate. These terms are well understood in the art. For purposes of this invention, replication involves production of adenovirus proteins and is generally directed to reproduction of adenovirus. Replication can be measured using assays standard in the art and described herein, such as a burst assay or plaque assay. "Replication" and "propagation" include any activity directly or indirectly involved in the process of virus manufacture, including, but not limited to, viral gene expression; production of viral proteins, nucleic acids or other components; packaging of viral components into complete viruses; and cell lysis.

A "host cell" includes an individual cell or cell culture which can be or has been a recipient of any vector of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo with a vector of this invention.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, farm animals, sport animals, and pets.

An "effective amount" is an amount sufficient to effect beneficial or desired clinical results. An effective amount can be administered in one or more administrations. For purposes of this invention, an effective amount of a polynucleotide vector is an amount that is sufficient to palliate, ameliorate, stabilize, reverse, slow or delay the progression of the disease state.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread (i.e., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease means that the extent and/or undesirable clinical manifestations of a disease state are lessened and/or time course of the progression is slowed or lengthened, as compared to not administering adenoviral vectors of the present invention.

Human Glandular Kallikrein Enhancer Sequences

The present invention provides isolated polynucleotide sequences, derived from the hKLK2 gene, that act to increase the transcription of operably linked polynucleotides in a cell-specific manner. These sequences are of use in controlling the transcription of polynucleotide sequences to which they are operably linked, and thus they may also lend a level of control to the expression of heterologous polynucleotides. These sequences, or a transcriptional regulatory element which they form, can be characterized, in part, by being linked to a polynucleotide sequence, the expression of which they regulate.

Accordingly, the present invention encompasses hKLK2 enhancer polynucleotides, vectors containing these polynucleotides, host cells containing these polynucleotides, and compositions comprising these polynucleotides. These polynucleotides are isolated and/or produced by chemical and/or recombinant methods, or a combination of these methods. Unless specifically stated otherwise, "polynucleotides" shall include all embodiments of the polynucleotide of this invention. These polynucleotides are useful as probes, primers, in expression systems, and in screening methods as described herein. hKLK2 enhancer activity is found within nucleotides 1 through 9765 of SEQ ID NO:1 (corresponding to −12,014 to −2257 relative to the transcription start site). As described herein, portions of this region have been identified which retain enhancer function. Enhancer activity has been demonstrated in the region from nucleotides 8021 to 8371 of SEQ ID NO:1 (corresponding to −3993 to −3643 relative to the transcription start site), as demonstrated in Example 7. Accordingly, the invention includes an isolated polynucleotide sequence comprising nucleotides about 8021 to about 8371 of SEQ ID NO:1. Enhancer activity has also been demonstrated in the region from nucleotides 7200 to 8371 of SEQ ID NO:1 (corresponding to −4814 to −3643 relative to the transcription start site), as demonstrated in Example 7. Accordingly, the invention includes an isolated polynucleotide sequence comprising about 7200 to about 8371 of SEQ ID NO:1. Enhancer activity has further been demonstrated in the region from 6859 to 8627 of SEQ ID NO:1 (−5155 to −3387 relative to the transcription start site), as shown in Example 6. Accordingly, the invention includes an isolated polynucleotide sequence comprising about about 6859 to about 8627 of SEQ ID NO:1. Enhancer activity has been demonstrated in the region from 5976 to 9620 of SEQ ID NO:1 (−6038 to −2394 relative to the transcription start site). Accordingly, the invention includes an isolated polynucleotide sequence comprising about 5976 to about 9620 of SEQ ID NO:1. An active enhancer lies within an XhoI-ApaI fragment spanning a region from about 2 to about 6 kb upstream of the hKLK2 structural gene. Accordingly, the invention further includes an isolated polynucleotide comprising nucleotides about 1 through about 9765 of SEQ ID NO:1. For each of these embodiments, the polynucleotide has enhancer activity.

An hKLK2 enhancer sequence spanning from 5976 to 9620 of SEQ ID NO:1 shares approximately 75% overall nucleotide sequence identity with a prostate specific antigen enhancer (PSE). As shown in FIG. 2, an hKLK2 enhancer sequence spanning nucleotides 7272 to 9498 of SEQ ID NO:1 shares 79% sequence identity with a 2187 nucleotide portion of a PSE (nucleotides 775 to 2961 of the sequence given in SEQ ID NO:2; GenBank Accession No. U37672). Furthermore, an hKLK2 enhancer from 8021 to 8458 of SEQ ID NO:1 shares 84% sequence identity with nucleotides 1500 to 1940 of the PSA-TRE given as SEQ ID NO:2, as shown in FIG. 2.

As noted above, the PSE and PSA promoter depicted in SEQ ID NO:2 is the same as that given in GenBank Accession No. U37672, and published. Schuur et al. (1996) *J. Biol. Chem.* 271:7043–7051. A variant PSA-TRE nucleotide sequence is depicted in SEQ ID NO:3. This is the PSA-TRE contained within CN706 clone 35.190.13. CN706 is an adenoviral vector in which the E1A gene in Ad5 is under transcriptional control of a PSA-TRE. CN706 demonstrates selective cytotoxicity toward PSA-expressing cells in vitro and in vivo. Rodriguez et al. (1997) Cancer Res. 57:2559–2563. CN706 was passaged through 293 and LNCaP cells. A clone, designated 35.190.13 was isolated. The structure of this clone was confirmed by PCR, restriction endonuclease digestion and Southern blotting. Both DNA strands of the CN706 clone 35.190.13 were sequenced between positions 1 and 3537. Seven single base pair changes were found in the PSE, compared to the sequence reported by Schuur et al. (1996). These point mutations are not in the ARE and are thus not likely to affect the function of the enhancer. One mutation was found in the PSA promoter region, but is not likely to affect gene expression from this promoter. In addition to these mutations, a missense mutation was found in the first exon of E1A. This C to G transition at position 3032 results in a Glu to Arg change in the E1A protein sequence. This mutation does not appear to diminish E1A function.

Figure 11:
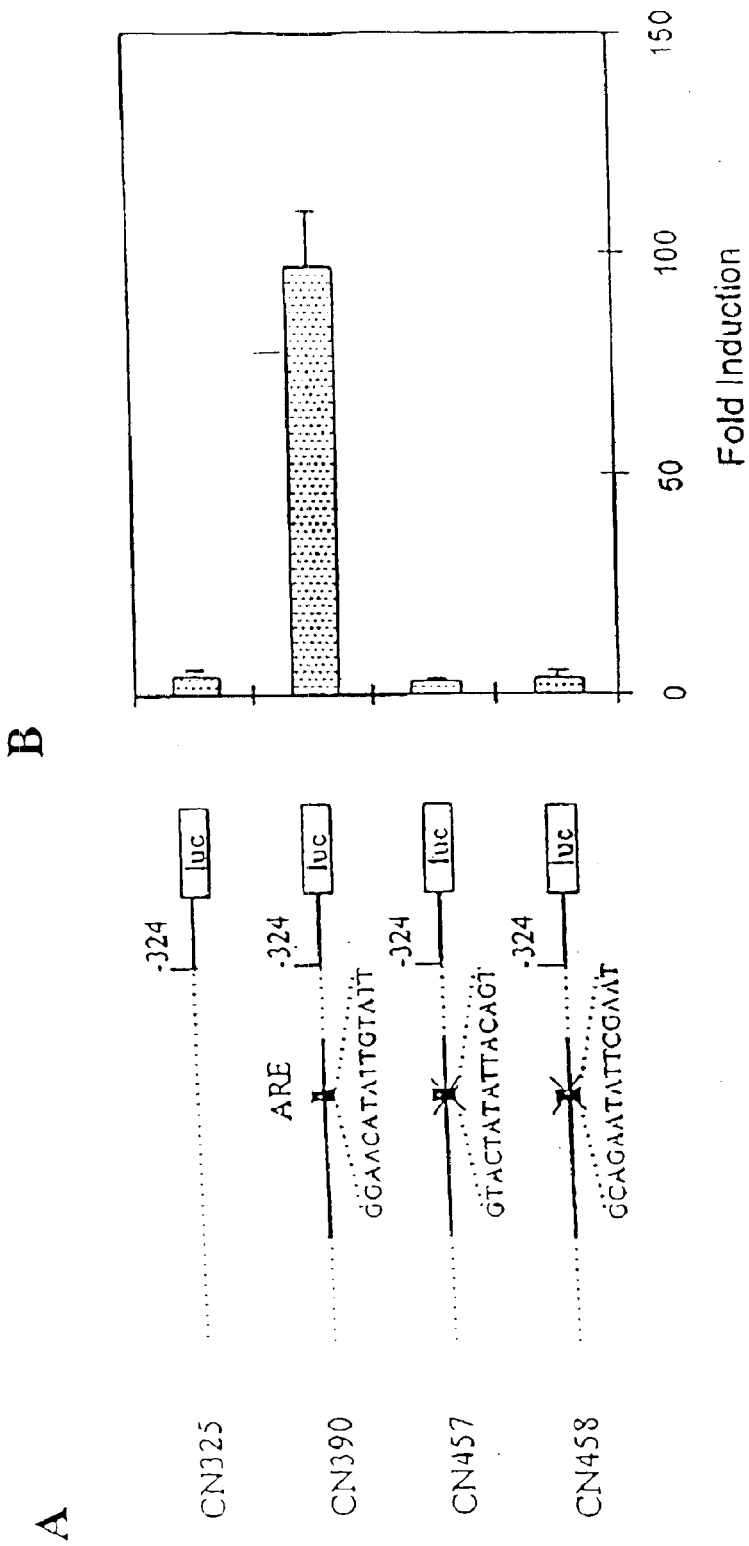
FIG. 11 is a bar graph depicting the activity of an hKLK2 enhancer having a putative ARE with wild-type (CN390) or mutated (CN457, CN458) sequence (FIG. 11B). The sequences of the putative ARE, and its mutated forms, are given below the appropriate constructs (FIG. 11A). LNCaP cells were transfected with the constructs and enhancer activity was measured as described in Example 3.

As shown in Example 7, an hKLK2 enhancer comprising nucleotides 6859 to 8627 of SEQ ID NO:1 is androgen inducible. The construct CN408 comprises this portion of an hKLK2 enhancer operably linked to an SV40 promoter and a reporter gene encoding luciferase activity. Upon androgen induction, an 80-fold increase in luciferase activity was observed. As shown in FIG. 11, a putative ARE is located at nucleotides 8192 to 8206 of SEQ ID NO:1.

Accordingly, an hKLK2 enhancer of the invention may be about 100 contiguous nucleotides, about 150, 200, 250, 300, 350, 400, 450, 500, 550, 600, 700, 800, 900, 1000, 1200, 1500, 1700, 2000 contiguous nucleotides or larger of the sequence depicted in nucleotides 1 to 11,407 of SEQ ID NO:1. Examples 6 and 7 provide methods that demonstrate that various hKLK2 enhancer sequences, together with a promoter, increase transcription of an operably linked heterologous polynucleotide in response to androgen. Similar methods can be used for identifying other hKLK2 enhancer sequences. Other methods for identifying an hKLK2 enhancer sequence are routine and well known in the art. For example, overlapping sequences of an hKLK2 enhancer can be synthesized and cloned into the vector described in Example 2 to determine hKLK2 enhancer activity. Similarly, point mutations can be introduced into the disclosed hKLK2 enhancer sequences using, for example, site-directed mutagenesis or by synthesizing sequences having random nucleotides at one or more predetermined positions and hKLK2 enhancer activity determined.

As an example of how hKLK2 enhancer activity can be determined, a polynucleotide sequence or set of such sequences can be generated using methods known in the art, such as chemical synthesis, site-directed mutagenesis, PCR, and/or recombinant methods. The sequence(s) to be tested can be inserted into a vector containing a promoter and an appropriate reporter gene encoding a reporter protein, including, but not limited to, chloramphenicol acetyl transferase (CAT), β-galactosidase (encoded by the lacZ gene), luciferase, (encoded by the luc gene), alkaline phosphatase, green fluorescent protein, and horse radish peroxidase. Such vectors and assays are readily available, from, inter alia, commercial sources. Plasmids thus constructed are transfected into a suitable host cell to test for expression of the reporter gene as controlled by the putative hKLK2 enhancer using transfection methods known in the art, such as calcium phosphate precipitation, electroporation, liposomes (lipofection), and DEAE dextran.

In one embodiment, the invention provides an isolated polynucleotide comprising 150 contiguous nucleotides of nucleotides about 1 to about 11,407 of SEQ ID NO:1, but not depicted in SEQ ID NO:2 or SEQ ID NO:3, and having enhancer activity. In another embodiment, the 150 contiguous nucleotides comprise nucleotides found within nucleotides about 5976 to about 9620 of SEQ ID NO:1. In another embodiment, the 150 contiguous nucleotides comprise nucleotides found within nucleotides about 6859 to about 8627 of SEQ ID NO:1. In yet another embodiment, the 150 contiguous nucleotides comprise nucleotides found within nucleotides about 7200 to about 8371 of SEQ ID NO:1. In yet another embodiment, the 150 contiguous nucleotides comprise nucleotides found within nucleotides about 8021 to about 8371 of SEQ ID NO:1. As noted above, enhancer activity may be found in various lengths of SEQ ID NO:1 (as well as in various regions of SEQ ID NO:1), and may thus also have a longer contiguous nucleotide sequence. In any and all of these embodiments, it is understood that the contiguous nucleotides are not depicted in SEQ ID NO:2 or SEQ ID NO:3.

In another embodiment, the invention provides an isolated polynucleotide comprising 150 contiguous nucleotides having at least about 70%, more preferably at least about 75%, more preferably at least about 80%, more preferably at least about 85%, even more preferably at least about 90%, even more preferably greater than 90% sequence identity to a sequence within SEQ ID NO:1, said polynucleotide having enhancer activity. As noted above, enhancer activity may be found in various lengths of SEQ ID NO:1 (as well as in various regions of SEQ ID NO:1), and may thus also have a longer contiguous nucleotide sequence. For these embodiments, the contiguous nucleotides may have at least about 75%, at least about 85%, at least about 90%, or at least about 95% sequence identity to a sequence of (i.e., within) SEQ. ID NO:1. In any and all of these embodiments, it is understood that the contiguous nucleotides are not depicted in SEQ ID NO:2 or SEQ ID NO:3.

In terms of hybridization conditions, the higher the sequence identity required, the more stringent are the hybridization conditions if such sequences are determined by their ability to hybridize to a sequence of SEQ ID NO:1. Accordingly, the invention also includes polynucleotides that are able to hybridize to a sequence comprising at least about 15 contiguous nucleotides (or more, such as about 25, 35, 50, 75 or 100 contiguous nucleotides) of SEQ ID NO:1. The hybridization conditions would be stringent, i.e., 80° C. (or higher temperature) and 6M SSC (or less concentrated SSC). For discussion regarding hybridization reactions, see below.

Hybridization reactions can be performed under conditions of different "stringency". Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water.

"$T_m$" is the temperature in degrees Celcius at which 50% of a polynucleotide duplex made of complementary strands hydrogen bonded in anti-parallel direction by Watson-Crick base pairing dissociates into single strands under conditions of the experiment. $T_m$ may be predicted according to a standard formula, such as:

$$T_m = 81.5 + 16.6\log[X^+] + 0.41\ (\%G/C) - 0.61\ (\%F) - 600/L$$

where [X$^+$] is the cation concentration (usually sodium ion, Na$^+$) in mol/L; (%G/C) is the number of G and C residues as a percentage of total residues in the duplex; (%F) is the percent formamide in solution (wt/vol); and L is the number of nucleotides in each strand of the duplex.

Also within the invention is an isolated polynucleotide at least about 15 nucleotides in length (preferably at least about 30, more preferably at least 100, more preferably at least about 150, even more preferably at least about 200, even more preferably at least about 250, even more preferably at least about 300, even more preferably at least about 400, and most preferably at least 450), including (a) a strand which hybridizes under stringent conditions to a DNA having the sequence of SEQ ID NO:1, (b) the complement thereof, or (c) a double-stranded DNA including both (a) and (b). Multiple copies of this isolated DNA (useful, for example, as a hybridization probe or PCR primer) can be produced by recombinant means, by transfecting a cell with a vector containing this DNA. In any and all of these embodiments, it is understood that the contiguous nucleotides are not depicted in SEQ ID NO:2 or SEQ ID NO:3.

Stringent conditions for both DNA/DNA and DNA/RNA hybridization are as described by Sambrook et al. *Molecular Cloning, A Laboratory Manual*, 2nd Ed., Cold Spring Harbor Laboratory Press, Cold Spring Harbor, N.Y., 1989, herein incorporated by reference. For example, see page 7.52 of Sambrook et al.

An hKLK2 enhancer sequence comprises an ARE. As shown in FIG. 11, an intact ARE is required for hKLK2 enhancer activity. An hKLK2 enhancer sequence carries sufficient information, when operably linked to a promoter, to increase transcription of a heterologous (non-hKLK2) polynucleotide to an extent which is greater than the transcription level effected by a promoter itself. Accordingly, an hKLK2 enhancer sequence may be of various lengths, as long as requisite function is sufficiently preserved.

Preferably, an hKLK2 enhancer contains nucleotides about −3822 to about −3808 relative to the transcription start site (nucleotides about 8192 to about 8206 of SEQ ID NO:1). This nucleotide sequence shares significant nucleotide sequence identity with a consensus ARE. Beato (1989) *Cell* 56:335–344; and Cleutjens et al. (1997) *Molec. Endocrinol.* 11:148–161. We have shown (FIG. 11 and Example 7) that mutations in this region abolish enhancer activity.

An hKLK2 enhancer may form part of an hKLK2 transcriptional regulatory element, or hKLK2-TRE, in which an hKLK2 enhancer is operably linked to a promoter, which may in turn be operably linked to a heterologous polynucleotide, i.e., a gene not naturally operably linked to an hKLK2 promoter or an hLKL2 enhancer. An hKLK2-TRE would increase expression of an operably linked gene preferentially in those cells which allow an hKLK2 enhancer to function. Accordingly, the invention also provides an isolated polynucleotide comprising a transcriptional regulatory element, wherein said transcriptional regulatory element comprises an hKLK2 enhancer and a promoter. The promoter may be heterologous or may be an hKLK2 promoter (for example, nucleotides about 11,290 to about 12,047 of SEQ ID NO:1).

Examples of heterologous polynucleotides which may be operably linked to an hKLK2 enhancer and a promoter include, but are not limited to, reporter genes, genes encoding compounds toxic to mammalian cells, genes encoding biological response modifiers, lymphokines, cytokines, cell surface antigens, synthetic genes which direct the synthesis of ribozymes or anti-sense ribonucleotides and genes encoding transcription factors.

Marker genes, or reporter genes, which may be employed are known to those skilled in the art and include, but are not limited to, luciferase; aequorian (i.e., green fluorescent protein from *Aequorea victoria*); β-galactosidase, chloramphenicol acetyl transferase; immunologically detectable protein "tags" such as human growth hormone; and the like. See, for example, Current Protocols in Molecular Biology (F. M. Ausubel et al., eds., 1987) and periodic updates. Any assay which detects a product of the reporter gene, either by directly detecting the protein encoded by the reporter gene or by detecting an enzymatic product of a reporter gene-encoded enzyme, is suitable for use in the present invention. Assays include calorimetric, fluorimetric, or luminescent assays or even, in the case of protein tags, radioimmunoassays or other immunological assays.

Toxin genes may include the diphtheria toxin A-chain gene, ricin A-chain gene, *Pseudomonas* exotoxin gene, etc. Maxwell et al. (1987) *Mol. Cell. Biol.* 7:1576; Frankel et al. (1989) *Mol Cell. Biol.* 9:415; Chaudhary et al. (1990) *Proc. Natl. Acad. Sci. U.S.A.* 87:4574. Such toxins are known to those skilled in the art. Other toxin genes may include mutated or truncated forms of naturally-occurring proteins which competitively or non-competitively inhibit the correct functioning of the naturally-occurring forms and which thereby may kill the cell. Alternatively, a toxin gene may comprise a gene that, when expressed, causes apoptosis.

Lymphokines and cytokines are known in the art and include, but are not. limited to, interleukins, interferons, colony-stimulating factors, etc.

Cell surface antigens include those which are not normally expressed on the surface of a given cell, and result in enhance immunocytotoxicity or immune reactivity toward the cell.

Synthetic genes which direct the synthesis of ribozymes or anti-sense ribonucleotides may also be operably linked to an hKLK2 enhancer and a promoter. Antisense RNA and DNA molecules and ribozymes may function to inhibit translation of a protein. S. T. Crooke and B. Lebleu, eds. *Antisense Research and Applications* (1993) CRC Press; and *Antisense RNA and DNA* (1988) D. A. Melton, Ed. Cold Spring Harbor Laboratory Cold Spring Harbor, N.Y. Antisense RNA and DNA molecules act to directly block the translation of mRNA by binding to targeted mRNA and preventing protein translation. Ribozymes are enzymatic RNA molecules capable of catalyzing the specific cleavage of RNA. The mechanism of ribozyme action involves sequence specific interaction of the ribozyme molecule to complementary target RNA, followed by an endonucleolytic cleavage. Within the scope of the invention are engineered hammerhead or other motif ribozyme molecules that specifically and efficiently catalyze endonucleolytic cleavage of RNA sequences.

Compositions comprising an hKLK2 enhancer polynucleotide as well as compositions comprising an hKLK2-TRE operably linked to a heterologous polynucleotide are encompassed by this invention. When these compositions are to be used pharmaceutically, they are combined with a pharmaceutically acceptable excipient. Accordingly, the invention also provides compositions of these polynucleotides, including compositions comprising these polynucleotides and a pharmaceutical excipient, as well pharmaceutical compositions comprising these vectors. Pharmaceutical excipients are well known in the art and need not be described in detail herein. See, for example, *Remington: The Science and Practice of Pharmacy* (19$^{th}$ edition, 1995), Gennaro, ed.

Preparation of hKLK2 Enhancer Polynucleotides of the Invention

The hKLK2 enhancer polynucleotides of this invention can be obtained using chemical synthesis, recombinant methods, or PCR.

Methods of chemical polynucleotide synthesis are well known in the art and need not be described in detail herein. One of skill in the art can use the sequences provided herein and a commercial DNA synthesizer to produce a desired DNA sequence.

For preparing hKLK2 enhancer polynucleotides using recombinant methods, a polynucleotide comprising a desired sequence can be inserted into a suitable vector, and the vector in turn can be introduced into a suitable host cell for replication and amplification. Polynucleotides may be inserted into host cells by any means known in the art. Cells are transformed by introducing an exogenous polynucleotide by direct uptake, endocytosis, transfection, f-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art and is described in U.S. Pat. Nos. 4,683,195, 4,800,159, 4,754,065 and 4,683,202, as well as PCR: *The Polymerase Chain Reaction*, Mullis et al. eds., Birkauswer Press, Boston (1994).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., (1989), for example. RNA can also be obtained through in vitro reactions. An hKLK2 enhancer polynucleotide can be inserted into a vector that contains appropriate transcription promoter sequences. Commercially available RNA polymerases will specifically initiate transcription at their promoter sites and continue the transcription process through the adjoining DNA polynucleotides. Placing hKLK2 enhancer polynucleotides between two such promoters allows the generation of sense or antisense strands of hKLK2 enhancer RNA.

Cloning and Expression Vectors Comprising an hKLK2 Enhancer Polynucleotide

The present invention further includes a variety of vectors (i.e., cloning and expression vectors) having cloned therein hKLK2 enhancer polynucleotide(s). These vectors can be used for expression of recombinant polypeptides as well as a source of hKLK2 enhancer polynucleotides. Cloning vectors can be used to obtain replicate copies of the hKLK2 enhancer polynucleotides they contain, or as a means of storing the polynucleotides in a depository for future recovery. Expression vectors (and host cells containing these expression vectors) can be used to obtain polypeptides produced from the polynucleotides they contain. They may also be used where it is desirable to express polypeptides, encoded by an operably linked polynucleotide, in an individual, such as for eliciting an immune response via the polypeptide(s) encoded in the expression vector(s). Suitable cloning and expression vectors include any known in the art, e.g., those for use in bacterial, mammalian, yeast and insect expression systems. Specific vectors and suitable host cells are known in the art and need not be described in detail herein. For example, see Gacesa and Ramji, Vectors, John Wiley & Sons (1994).

Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selection genes encode protein(s) that (a) confer resistance to antibiotics or other toxins substances, e.g., ampicillin, neomycyin, methotrexate, etc.; (b) complement auxotrophic deficiencies; or (c) supply critical nutrients not available from complex media. The choice of the proper marker gene will depend on the host cell, and appropriate genes for different hosts are known in the art. Cloning and expression vectors also typically contain a replication system recognized by the host.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen. The Examples provided herein also provide examples of cloning vectors.

Expression vectors generally are replicable polynucleotide constructs that contain a polynucleotide encoding a polypeptide of interest. The polynucleotide encoding the polypeptide of interest is operably linked to suitable transcriptional controlling elements, such as promoters, enhancers and terminators. For expression (i.e., translation), one or more translational controlling elements are also usually required, such as ribosome binding sites, translation initiation sites, and stop codons. These controlling elements (transcriptional and translational) may be derived from hKLK2 polynucleotides (e.g., the hKLK2 gene), or they may be heterologous (i.e., derived from other genes and/or other organisms). A polynucleotide sequence encoding a signal peptide can also be included to allow a polypeptide, encoded by an operably linked polynucleotide, to cross and/or lodge in cell membranes or be secreted from the cell. A number of expression vectors suitable for expression in eukaryotic cells including yeast, avian, and mammalian cells are known in the art. Examples of mammalian expression vectors contain both prokaryotic sequence to facilitate the propagation of the vector in bacteria, and one or more eukaryotic transcription units that are expressed in eukaryotic cells. Examples of mammalian expression vectors suitable for transfection of eukaryotic cells include the pcDNAI/amp, pcDNAI/neo, pRc/CMV, pSV2gpt, pSV2neo, pRSVneo, and pHyg derived vectors. Alternatively, derivatives of viruses such as the bovine papilloma virus (BPV-1), or Epstein-Barr virus (pHEB, pREP derived vectors) can be used for expression in mammalian cells. Examples of expression vectors for yeast systems, include YEP24, YIP5, YEP51, YEP52, YES2 and YRP17, which are cloning and expression vehicles useful for introduction of constructs into S. cerevisiae. Broach et al. (1983) Experimental Manipulation of Gene Expression, ed. M. Inouye, Academic Press. p. 83. Other common vectors, such as YEP13 and the Sikorski series pRS303–306, 313–316, 423–426 can also be used. Vectors pDBV52 and pDBV53 are suitable for expression in C. albicans. Baculovirus expression vectors for expression in insect cells include pVL-derived vectors (such as pVL1392, pVL1393 and pVL941), pAcUW-derived vectors and pBlueBac-derived vectors.

A vector comprising an hKLK2 enhancer polynucleotide can be introduced into a host cell and/or a target cell by any of a number of appropriate means, including electroporation, transfection employing calcium chloride, rubidium chloride, calcium phosphate, DEAE-dextran, or other substances; microprojectile bombardment; lipofection; and infection (where the vector is an infectious agent, such as vaccinia virus). The choice of means of introducing vectors or hKLK2 enhancer polynucleotides will often depend on the host cell or target cell. A vector comprising an hKLK2 enhancer polynucleotide can also be delivered to a host cell and/or a target cell in the form of a delivery vehicle, described below.

Delivery Vehicles Containing an hKLK2 Enhancer Polynucleotide

The present invention also provides delivery vehicles suitable for delivery of an hKLK2 enhancer polynucleotide into cells (whether in vivo, ex vivo, or in vitro). Generally, an hKLK2 enhancer will be operably linked to a promoter and a heterologous polynucleotide. An hKLK2 enhancer polynucleotide can be contained within a cloning or expression vector, as described above, or within a viral vector. These vectors (especially expression vectors) can in turn be manipulated to assume any of a number of forms which may, for example, facilitate delivery to and/or entry into a target cell. Delivery of the polynucleotide constructs of the invention to eukaryotic cells, particularly to mammalian cells, more particularly to prostate cells, can be accomplished by any suitable art-known method. Delivery can be accomplished in vivo, ex vivo, or in vitro.

The invention provides methods and compositions for transferring such expression constructs into cells, especially in vivo for treatment of prostate disease. It is also an object of the invention to provide compositions for the therapy of BPH and prostatic neoplastic diseases.

Delivery vehicles suitable for incorporation of an hKLK2 enhancer of the present invention for introduction into a host cell include non-viral vehicles and viral vectors. Verma and Somia (1997) Nature 389:239–242.

Non-Viral Vehicles

A wide variety of non-viral vehicles for delivery of hKLK2 enhancer polynucleotides of the present invention are known in the art and are encompassed in the present invention. An hKLK2 enhancer polynucleotide can be delivered to a cell as naked DNA (U.S. Pat. No. 5,692,622; WO 97/40163). Alternatively, an hKLK2 enhancer polynucleotide can be delivered to a cell associated in a variety of ways with a variety of substances (forms of delivery) including, but not limited to cationic lipids; biocompatible polymers, including natural polymers and synthetic polymers; lipoproteins; polypeptides; polysaccharides; lipopolysaccharides; artificial viral envelopes; metal particles; and bacteria. A delivery vehicle may take the form of a microparticle. Mixtures or conjugates of these various substances can also be used as delivery vehicles. An hKLK2 enhancer polynucleotide can be associated with these various forms of delivery non-covalently or covalently.

One non-viral gene transfer vehicle suitable for use in the present invention is physical transfer of a polynucleotide in cationic lipids, which can take the form of liposomes. Reviewed in Mahato et al. (1997) Pharm. Res. 14:853–859. Liposomal preparations include, but are not limited to, cytofectins, multilamellar vesicles and unilamellar vesicles. Several commercial liposomal preparations are available for the delivery of DNA and RNA to cells, including but not limited to, Lipofectin™, Lipofectamine™, and DOTAP™.

Derivatized liposomes can be used as carriers of hKLK2 enhancer polynucleotides. Immunoliposomes are derivatized liposomes which contain on their surface specific antibodies which bind to surface antigens on specific cell types, thus targeting these liposomes to particular cell types. Wang and Huang (1987) Proc. Natl. Acad. Sci. (U.S.A.) 84:7851; and Trubetskoy et al. (1992) Biochem. Biophys. Acta 1131:311. Other types of derivatization include modification of the liposomes to include ligands which bind to receptors on particular cell types, or receptors which bind specifically to cell surface molecules.

Lipopolyamine can be used as a reagent to mediate transfection itself, without the necessity of any additional phospholipid to form liposomes. Behr et al. (1989) Proc. Natl. Acad. Sci. (U.S.A.) 86:6982.

Other lipid-based delivery vehicles are known and have been described, and can be used in the present invention. For example, U.S. Pat. No. 5,705,385 discloses lipid-nucleic acid particles for gene delivery via formation of hydrophobic lipid-nucleic acid complexes. The complexes are charge-neutralized. Formation of these complexes in either detergent-based or organic solvent-based systems, followed by removal of the detergent or organic solvent, leads to particle formation.

Polypeptide gene delivery vehicles include polyamino acids such as polylysine, and various naturally occurring polypeptides such as gelatin, and conjugates of these with other macromolecules.

Low molecular weight polylysine (PL) and other polycations can be used as carriers to promote DNA-mediated transfection into cultured mammalian cells. Zhou et al. (1991) Biochem. Biophys. Acta 1065:1068 reports synthesis of a polylysine-phospholipid conjugate, a lipopolylysine comprising PL linked to N-glutarylphosphatidylethanolamine, which reportedly increases the transfection efficiency of DNA.

Polylysine molecules conjugated to asialoorosomucoid ("ASOR") or transferrin can be used for target-specific delivery of associated polynucleotides to cells which express the appropriate receptor (i.e., asialoglycoprotein receptor or transferrin receptor, respectively). Such conjugates have been described. Wilson et al. (1992) J. Biol. Chem. 267:963; WO92/06180; WO92/05250; WO91/17761; Wagner et al. (1990) Proc. Natl. Acad. Sci. U.S.A. 87:3410; Zenke et al. (1990) Proc. Natl. Acad. Sci. U.S.A. 87:3655; and WO92/13570.

Polypeptide delivery vehicles include those which form microspheres, as described. WO 96/00295. Polypeptide microspheres can comprise polypeptide alone or mixtures of polypeptides with other macromolecules, for example chondroitin sulfate. The polypeptides may be crosslinked, as described. WO 96/40829. In addition, a targeting moiety can be incorporated into such polypeptide delivery vehicles.

Microparticles for delivery of polynucleotides into cells are known and can be used to deliver hKLK2 enhancer polynucleotides to a cell. Microparticles generally comprise a polynucleotide and a substance which facilitates entry into a cell. These include, for example, polymeric cations, complexes of hydrophobized, positively charged biocompatible polymer and a lipoprotein (U.S. Pat. No. 5,679,559); complexes of a receptor ligand and a polycation (U.S. Pat. No. 5,635,383); polycation conjugated with polyalkylene glycol or a polysaccharide (WO 96/21036); a complex between a fusion protein comprising a domain which specifically binds an hKLK2 enhancer polynucleotide and a domain which targets a particular cell type (EP 753,069); chylomicrons (Hara et al. (1997) *Proc. Natl. Acad. Sci. USA* 94:14547–14552); metal particles such as tungsten and gold (Zelenin et al. (1997) *FEBS Letters* 414:319–322; and chitosan-based compounds (WO 97/42975).

Other types of carriers include covalently bound conjugates consisting of oligonucleotides in disulfide linkage to a targeting agent that promotes transport across cell membranes (WO 91/14696); artificial viral envelopes (Schreier et al. (1995) *J. Molec. Recognition* 8:59–62; and Chander and Schreier (1992) *Life Sci.* 50:481–489; and bacteria, for example *Salmonella* (Pawelek et al. (1997) *Cancer Res.* 57:4537–4544); and *Listeria monocytogenes* (Dietrich et al. (1998) *Nature Biotech.* 16:181–185.

The delivery vehicles of the present invention can include one or more targeting molecules incorporated into or attached to the vehicle. Targeting molecules include any molecule that binds specifically to a target cell type. This can be any type of molecule for which a specific binding partner exists. The term "specific binding partner" as used herein intends a member of a pair of molecules that interact by means of specific non-covalent interactions that depend on the three-dimensional structures of the molecules involved. Preferably, the specific binding partner is expressed only on the target cell type. Examples of targeting molecules which may be used are hormones, antibodies, cell adhesion molecules, saccharides, drugs, and neurotransmitters.

Compositions comprising an hKLK2 enhancer polynucleotide in a delivery vehicle are encompassed by this invention. When these compositions are to be used pharmaceutically, they are combined with a pharmaceutically acceptable excipient. Accordingly, the invention also provides compositions of these vectors, including compositions comprising these vectors and a pharmaceutical excipient, as well pharmaceutical compositions comprising these vectors. Pharmaceutical excipients are well known in the art and need not be described in detail herein. See, for example, *Remington: The Science and Practice of Pharmacy* (19$^{th}$ edition, 1995), Gennaro, ed.

An hKLK2 enhancer polynucleotide can be inserted into a non-viral vector for delivery into a cell, as described above. Included in the non-viral vector category are prokaryotic plasmids and eukaryotic plasmids, as described above. One skilled in the art will appreciate that a wide variety of such vectors are known, are readily available, and can be used in the present invention. An hKLK2 enhancer polynucleotide inserted into a non-viral vector can be delivered to a cell with the help of any of the above-described vehicles, as well as direct injection of the polynucleotide, or other types of delivery methods. The above-described delivery vehicles can also be used to delivery an hKLK2 enhancer polynucleotide inserted into a viral vector.

Viral Vectors

An hLKL2 enhancer polynucleotide can be inserted into a viral vector. Viral vectors include, but are not limited to, DNA viral vectors such as those based on adenoviruses, herpes simplex virus, poxviruses such as vaccinia virus, and parvoviruses, including adeno-associated virus; and RNA viral vectors, including, but not limited to, the retroviral vectors. Retroviral vectors include murine leukemia virus, and lentiviruses such as human immunodeficiency virus. Naldini et al. (1996) *Science* 272:263–267.

Replication-defective retroviral vectors harboring an hKLK2 polynucleotide sequence as part of the retroviral genome can be used. Such vectors have been described in detail. (Miller et al. (1990) *Mol. Cell Biol.* 10:4239; Kolberg, R. (1992) *J. NIH Res.* 4:43; Cornetta et al. (1991) *Hum. Gene Ther* 2:215). The major advantages of retroviral vectors for gene therapy are: the high efficiency of gene transfer into replicating cells, the precise integration of the transferred genes into cellular DNA, and the lack of further spread of the sequences after gene transduction.

Representative examples of retroviral gene delivery vehicles that may be utilized within the context of the present invention include, for example, those described in EP 415,731; WO 90/07936; WO 94/03622; WO 93/25698; WO 93/25234; U.S. Pat. No. 5,219,740; WO 93/11230; WO 93/10218; Vile and Hart, *Cancer Res.* 53:83–88, 1993; Vile and Hart, *Cancer Res.* 53:962–967, 1993; Ram et al., *Cancer Res.* 53:83–88, 1993; Takamiya et al., *J. Neurosci. Res.* 33: 493–503, 1992; Baba et al., *J. Neurosurg* 79:729–735, 1993 (U.S. Pat. No. 4,777,127, GB 2,200,651, EP 0,345,242 and WO 91/02805).

Examples of suitable retroviruses include pLJ, pZIP, pWE and pEM which are well known to those skilled in the art. Examples of suitable packaging virus lines for preparing both ecotropic and amphotropic retroviral systems include psi Crip, psi cre, psi 2 and psi Am. Retroviruses have been used to delivery a variety of polynucleotides into many different cell types. See, for example, Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115.

Adenoviral vectors can also be used for delivery of hKLK2 enhancer polynucleotides. Rosenfeld et al. (1992) *Cell* 68:143. Adenoviral vector embodiments of the invention are discussed in a separate section. Major advantages of adenovirus vectors are their potential to carry large insert polynucleotide sequences, very high viral titres, ability to infect non-replicating cells, and suitability for infecting tissues in situ.

For the purposes of this invention, the adenoviral vectors can be replication competent or replication defective, depending on the desired outcome of infection with virus.

In general, replication-defective adenovirus gene transfer systems are based upon recombinant, engineered adenovirus which is rendered replication-incompetent by deletion of a portion of its genome, such as E1 or E3, and yet still retains its competency for infection. Berkner et al. (1988) *BioTechniques* 6:616; Rosenfeld et al. (1991) *Science* 252:431–434; Rosenfeld et al. (1992) *Cell* 68:143–155. Relatively large foreign proteins can be expressed when additional deletions are made in the adenovirus genome. For example, adenoviruses deleted in both E1 and E3 regions are capable of carrying up to 10 kb of foreign DNA and can be grown to high titers in 293 cells. Suitable adenoviral vectors derived from the adenovirus strain Ad type 5 or other strains of adenovirus (e.g., Ad2, Ad3, Ad7, etc.) are well known to those skilled in the art.

A replication-competent adenoviral vector comprising an hKLK2 enhancer polynucleotide is one embodiment of a delivery vehicle comprising an hKLK2 enhancer. Replication-competent adenoviral vectors comprising an hKLK2 enhancer will be discussed in more detail below.

Another viral vector system useful for delivery of an hKLK2 enhancer polynucleotide is the adeno-associated virus (AAV). Adeno-associated virus is a naturally occurring defective virus that requires another virus, such as an adenovirus or a herpes virus, as a helper virus for efficient replication and a productive life cycle. Muzyczka et al. (1992) *Curr. Topics Microbiol. Immunol.* 158:97–129. AAV as a delivery vehicle for an hKLK2 enhancer polynucleotide can be constructed and introduced into cells by any means known in the art, including the methods described in U.S. Pat. No. 5,658,785.

In addition to the viral vectors describe above, numerous other viral vectors systems may also be utilized as a gene delivery vehicle. Representative examples of such gene delivery vehicles include viruses such as pox viruses, such as canary virus or vaccinia virus (Fisher-Hoch et al., *PNAS* 86:317–321, 1989; Flexner et al., *Ann N.Y. Acad. Sci.* 569:86–103, 1989; Flexner et al., *Vaccine* 8:17–21, 1990; U.S. Pat. Nos. 4,603,112, 4,769,330, 5,017,487 and 5,656,465; WO 89/01973); SV40 (Mulligan et al., *Nature* 277:108–114, 1979; influenza virus (Luytjes et al., *Cell* 59:1107–1113, 1989; McMicheal et al., *N. Eng. J. Med.* 309:13–17, 1983; and Yap et al., *Nature* 273:238–239, 1978; herpes (Kit, *Adv. Exp. Med. Biol.* 215:219–236 1989; U.S. Pat. No. 5,288,641); HIV (Poznansky, *J. Virol.* 65:532–536, 1991); measles (EP 0 440,219); Semliki Forest Virus, and coronavirus, as well as other viral systems (e.g., EP 0,440, 219; WO 92/06693; U.S. Pat. No. 5,166,057). In addition, viral carriers may be homologous, non-pathogenic (defective), replication competent virus (e.g., Overbaugh et al., *Science* 239:906–910, 1988), and nevertheless induce cellular immune responses, including CTL.

Viral vectors comprising an hKLK2 enhancer polynucleotide can be targeted to a particular cell type for more efficient delivery of an hKLK2 enhancer polynucleotide, for example, to a neoplastic prostate cell. For example, a viral vector can comprise, in addition to an hKLK2 enhancer polynucleotide, a polynucleotide encoding one member of a specific binding pair which inserts into the viral envelope or capsid and which targets the viral particle to a cell having the complementary member of the specific binding pair on its surface. WO 95/26412. Alternatively, the surface of a viral particle can be covalently modified to target it to a particular cell. WO 92/06180; WO 92/05266.

Viral vectors can be so constructed that they contain regulatable control elements which are controlled, for example, by tetracycline. WO 97/20463.

Virus-based vectors can also be used to deliver an hKLK2 enhancer polynucleotide. These include retrotransposon vectors (U.S. Pat. No. 5,354,674) and synthetic vectors (WO 94/20608; WO 96/26745).

Preparation of Non-viral Vehicles Comprising an hKLK2 Enhancer

Preparation of liposomes for transfer of polynucleotides can be carried out as described by various investigators (Wang and Huang (1987) *Biochem. Biophys. Res. Commun.* 147:980; Wang and Huang (1989) *Biochemistry* 28:9508; Litzinger and Huang (1992) *Biochem. Biophys. Acta* 1113 201; Gao and Huang (1991) *Biochem. Biophys. Res. Commun.* 179:280; Felgner WO91117424; WO91116024).

The preparation of other types of non-viral vehicles is known in the art and has been described. For example, preparation of polylysine delivery vehicles has been described by Zhou et al. (1991) *Biochem. Biophys. Acta* 1065:1068. Methods for preparation of microparticles of various compositions have also been described (see publications cited above) and are known in the art.

Introduction of targeting molecules into the non-viral vehicles of the present invention can be carried out by any known means, including incorporation into a cationic lipid vehicle or a microsphere or a microparticle; by direct chemical conjugation with a macromolecule of which the delivery vehicle is comprised, or any other known methods. Introduction Into Host Cells and/or Target Cells of Non-viral Vehicles Comprising an hKLK2 Enhancer Non-viral vehicles comprising an hKLK2 enhancer polynucleotide may be introduced into host cells and/or target cells by any method known in the art, such as transfection by the calcium phosphate coprecipitation technique; electroporation; electropermeabilization; liposome-mediated transfection; ballistic transfection; biolistic processes including microparticle bombardment, jet injection, and needle and syringe injection; or by microinjection. Numerous methods of transfection are known to the skilled worker in the field. A number of these methods can be carried out both ex vivo and in vivo. Biolistic gene transfer, including jet injection, microparticle bombardment and needle and syringe injection, can be carried out by art-known methods. For a review, see Furth (1997) *Mol. Biotechnol.* 7:139–143. In vivo electropermeabilization can be performed as described. Rols et al. (1998) *Nature Biotech.* 16:168–1171. Successful transfection is generally recognized when any indication of the operation of this vector occurs in the host cell. Transformation is achieved using standard techniques appropriate to the particular host cells used. Naked DNA can be introduced by direct injection. Polynucleotides can also be introduced using various implantable devices such as those described in U.S. Pat. No. 5,501,662; and Koole et al. (1998) *Nature Biotech.* 16:172–176.

Preparation of Viral Vectors Comprising an hKLK2 Enhancer

The basic technique of inserting genes into viruses are known to the skilled artisan and involve, for example, recombination between the viral polynucleotide sequences flanking a polynucleotide in a donor plasmid and homologous sequences present in the parental virus. Mackett et al. (1982) *Proc. Natl. Acad. Sci. USA* 79:7415–7419. For example, a unique restriction site that is naturally present or artificially inserted in the parental viral vector can be used to insert a polynucleotide flanked by the same restriction site as in the viral vector.

A DNA virus can be constructed as follows. First, the polynucleotide sequence to be inserted into the virus can be placed into a plasmid, e.g., an *E. coli* plasmid construct, into which a polynucleotide homologous to a section of the polynucleotide such as that of the virus has been inserted. Separately the polynucleotide sequence to be inserted is ligated to a promoter. The promoter-gene linkage is positioned in the plasmid construct so that the promoter-gene linkage is flanked on both ends by polynucleotide sequences homologous to a polynucleotide sequence flanking a region of viral DNA which is the desired insertion region. The resulting plasmid construct is then amplified by growth within *E. coli* bacteria and isolated. Preferably, the plasmid also contains an origin of replication such as the *E. coli* origin of replication, and a marker such as an antibiotic resistance gene for selection and propagation in *E. coli*.

Second, the isolated plasmid containing the polynucleotide sequence to be inserted is transfected into a cell culture, e.g., chick embryo fibroblasts, along with the virus. Recombination between homologous DNA in the plasmid and the viral genome respectively results in a virus modified by the presence of the polynucleotide construct in its genome, at a site which does not affect virus viability.

As noted above, the gene is inserted into a region (insertion region), in the virus which does not affect virus viability of the resultant recombinant virus. The skilled artisan can readily identify such regions in a virus by, for example, randomly testing segments of virus DNA for regions that allow recombinant formation without seriously affecting virus viability of the recombinant. One region that can readily be used and is present in many viruses is the thymidine kinase gene.

Techniques for preparing replication-defective adenoviruses are well known in the art, as exemplified by Ghosh-Choudhury and Graham (1987) *Biochem. Biophys. Res. Comm.* 147:964–973; Ghosh-Choudhury et al. (1987) *EMBO J.* 6:1733–1739; McGrory et al. (1988) Virol. 163:614–617. It is also well known that various cell lines may be used to propagate recombinant adenoviruses, so long as they complement any replication defect which may be present. One example is the human 293 cell line, but any other cell line that is permissive for replication. For example, for viral constructs which, by virtue of insertion of an hKLK2 enhancer polynucleotide, E1A and E1B are not expressed, a cell line which expresses E1A and E1B is employed. Further, the cells can be propagated either on plastic dishes or in suspension culture, in order to obtain virus stocks.

Preparation of replication-competent adenoviral vectors is discussed in a separate section.

Recombinant retroviruses which are constructed to carry or express an hKLK2 enhancer polynucleotide can be readily constructed from a wide variety of retroviruses, including for example, B, C, and D type retroviruses as well as spumaviruses and lentiviruses (see *RNA Tumor Viruses*, Second Edition, Cold Spring Harbor Laboratory, 1985). Such retroviruses may be readily utilized in order to assemble or construct retroviral gene delivery vehicles given the disclosure provided herein, and standard recombinant techniques (e.g., Sambrook et al, *Molecular Cloning: A Laboratory Manual*, 2d ed., Cold Spring Harbor Laboratory Press, 1989; Kunkle, *PNAS* 82:488, 1985). In addition, portions of the retroviral gene delivery vehicles may be derived from different retroviruses. For example, retroviral LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

A major prerequisite for the use of retroviruses is to ensure the safety of their use, particularly regarding the possibility of the spread of wild-type virus in the cell population. The development of specialized cell lines ("packaging cells") which produce only replication-defective retroviruses has increased the utility of retroviruses for gene delivery, and defective retroviruses are well characterized for gene delivery puroposes. Miller et al. (1990) *Blood* 76:271. Recombinant retroviruses can be constructed in which part of the retroviral coding sequence (gag, pol, env) has been replaced by an hKLK2 enhancer polynucleotide, rendering the retrovirus replication defective. The replication-defective virus is then packaged into virions which can be used to infect a target cell through the use of a helper virus by standard techniques. Protocols for producing recombinant retroviruses and for infecting cells in vitro or in vivo can be found in Current Protocols in Molecular Biology, Ausubel, F. M. et al. (eds) Greene Publishing Associates (1989) and periodic updates, and other standard laboratory manuals.

Packaging cell lines suitable for use with the above-described vector constructs may be readily prepared (see WO 92/05266), and utilized to create producer cell lines (also termed vector cell lines or "VCLs") for the production of recombinant vector particles, given the disclosure provided herein.

Introduction into Host Cells and/or Target Cells of Viral Vehicles Comprising an hKLK2 Enhancer Viral delivery vehicles can be introduced into cells by infection. Alternatively, viral vehicles can be incorporated into any of the non-viral delivery vehicles described above for delivery into cells. For example, viral vectors can be mixed with cationic lipids (Hodgson and Solaiman (1996) *Nature Biotechnol.* 14:339–342); or lamellar liposomes (Wilson et al. (1977) *Proc. Natl. Acad. Sci. USA* 74:3471; Faller et al. (1984) *J. Virol.* 49:269).

For in vivo delivery, the delivery vehicle(s) can be introduced into a patient by any of a number of methods, each of which is familiar in the art. For instance, a pharmaceutical preparation of the gene delivery system can be introduced systematically, e.g. by intravenous injection, and specific transduction of the target cells occurs predominantly from specificity of transfection provided by the gene delivery vehicle, cell-type or tissue-type expression due to the transcriptional regulatory sequences controlling expression of the gene, or a combination thereof. In other embodiments initial delivery of the recombinant gene is more limited with introduction into the animal being quite localized. For example, the gene delivery vehicle can be introduced by catheter (see U.S. Pat. No. 5,328,470) or by sterotactic injection (e.g. Chen et al. (1994) *Proc. Natl. Acad. Sci. USA*. 91:3054–3057). Moreover, the pharmaceutical preparation can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral packages, the pharmaceutical preparation can comprise one or more cells which produce the gene delivery system. In the case of the latter, methods of introducing the viral packaging cells may be provided by, for example, rechargeable or biodegradable devices. Various slow release polymeric devices have been developed and tested in vivo in recent years for the controlled delivery of drugs, including proteinacious biopharmaceuticals, and can be adapted for release of viral particles through the manipulation of the polymer composition and form. A variety of biocompatible polymers (including hydrogels), including both biodegradable and non-degradable polymers, can be used to form an implant or the sustained release of an the viral particles by cells implanted at a particular target site. Such embodiments of the present invention can be used for the delivery of an exogenously purified virus, which has been incorporated in the polymeric device, or for the delivery of viral particles produced by a cell encapsulated in the polymeric device.

By choice of monomer composition or polymerization technique, the amount of water, porosity and consequent permeability characteristics can be controlled. The selection of the shape, size, polymer, and method for implantation can be determined on an individual basis according to the disorder to be treated and the individual patient response. The generation of such implants is generally known in the art. See, for example, *Concise Encyclopedia of Medical & Dental Materials*, ed. by David Williams (MIT Press: Cambridge, Mass., 1990); and the Sabel et al. U.S. Pat. No. 4,883,666. In another type of implant, a source of cells producing the recombinant virus is encapsulated in implantable hollow fibers. Such fibers can be pre-spun and subsequently loaded with the viral source (Aebischer et al. U.S. Pat. No. 4,892,538; Aebischer et al. U.S. Pat. No. 5,106,627; Hoffman et al. (1990) Expt. Neurobiol. 110:39–44; Jaeger et al. (1990) Prog. Brain Res. 82:41–46; and Aebischer eta. (1991) J. Biomech. Eng 113: 178–183), or can be co-extruded with a polymer which acts to form a polymeric coat about the viral packaging cells (Lim U.S. Pat. No. 4,391,909; Sefton U.S. Pat. No. 4,353,888; Sugarmori et al. (1989) Trans. Am. Artif. Intern. Organs 35:791–799; Sefton et al. (1987) Biotechnol. Bioeng. 29:1135–1143; and Aebischer eta. (1991) Biomaterals 12:50–55. Again, manipulation of the polymer can be carried out to provide for optimal release of viral particles.

Host Cells and Target Cells Comprising an hkLK2 Enhancer Polynucleotide

The invention further provides host cells and target cells transfected or transformed with (i.e., comprising) the above-described hKLK2 enhancer(s) and/or hKLK2-TRE(s), above-described expression or cloning vectors of this invention, or above-described delivery vehicles comprising hKLK2 enhancer(s) and/or hKLK2-TRE(s). These cells are cultured in conventional nutrient media modified as appropriate for inducing promoters, selecting transformants, or amplifying the genes encoding the desired sequences.

The cells which are suitable for use in the methods of the present invention with respect to expression, transcriptional control, or for purposes of cloning and propagating an hKLK2 enhancer polynucleotide can be prokaryotic or eukaryotic.

Host systems are known in the art and need not be described in detail herein. Prokaryotic hosts include bacterial cells, for example *E. coli, B. subtilis*, and mycobacteria. Among eukaryotic hosts are yeast, insect, avian, plant, *C. elegans* (or nematode) and mammalian cells. Examples of fungi (including yeast) host cells are *S. cerevisiae, Kluyveromyces lactis* (*K. lactis*), species of *Candida* including *C. albicans* and *C. glabrata, Aspergillus nidulans, Schizosaccharomyces pombe* (*S. pombe*), *Pichia pastoris*, and *Yarowia lipolytica*. Examples of mammalian cells are COS cells, mouse L cells, LNCaP cells, Chinese hamster ovary (CHO) cells, human embroyonic kidney (HEK) cells, and African green monkey cells. *Xenopus laevis* oocytes, or other cells of amphibian origin, may also be used.

For the delivery vehicles described above, any eukaryotic cells, preferably mammalian cells can be used. Even more preferably, the cells are prostate cells, more preferably expressing androgen receptor, even more preferably prostate epithelial cells expressing endogenous androgen receptor. The cells employed may be those derived from the prostate. Such cells include, but are not limited to, the LNCaP cell line (available from the American Type Culture Collection under ATCC CRL 1740). Alternatively, the cells need not be derived from the prostate as long as the hKLK2-TRE function is sufficiently preserved. This may be achieved, for example, by co-transfecting the cell with a gene encoding a product necessary for the function of the TRE of the prostate-specific gene. For example, if an hKLK2-TRE is inducible by androgen, it may be necessary to co-transfect into the cells a construct which encodes and allows expression of a gene encoding an androgen receptor.

The host cells of this invention can be used, inter alia, as repositories of hKLK2 polynucleotides and/or vehicles for production of hKLK2 polynucleotides and/or polypeptides which are encoded by an operably linked polynucleotide.

Compositions containing cells into which have been introduced vectors comprising an hKLK2-TRE operably linked to a heterologous polynucleotide are encompassed by this invention. When these compositions are to be used pharmaceutically, they are combined with a pharmaceutically acceptable excipient. Accordingly, the invention also provides compositions of these cells, including compositions comprising these cells and a pharmaceutical excipient, as well pharmaceutical compositions comprising these cells. Pharmaceutical excipients are well known in the art and need not be described in detail herein. See, for example, *Remington: The Science and Practice of Pharmacy* (19$^{th}$ edition, 1995), Gennaro, ed.

Methods Using the hKLK2 Enhancer Polynucleotides of the Invention

The above-described hKLK2 enhancer sequences can be used for a wide variety of purposes, which will vary with the desired or intended result. Accordingly, the present invention includes methods using the hKLK2 enhancer sequences described above.

As described above, an hKLK2 enhancer can be operably linked to a promoter to form an hKLK2-TRE, which can in turn be operably linked to a heterologous polynucleotide. Such an hKLK2-TRE is useful for selectively increasing transcription and/or expression of an operably linked heterologous polynucleotide in cells which allow an hKLK2 enhancer to function. Accordingly, the invention includes methods for increasing transcription of a polynucleotide sequence in a cell, generally involving introducing a construct comprising an hKLK2 enhancer and a promoter operably linked to the polynucleotide into a cell in which the hKLK2 enhancer is functional.

In one embodiment, methods are provided for introducing a construct comprising an hKLK2-TRE operably linked to a reporter gene into cells which allow an hKLK2 enhancer to function, i.e., a cell in which an hKLK2 enhancer, when operably linked to a promoter and a reporter gene, increases expression of the reporter gene. Examples include LNCaP cells, as shown in Examples 6 and 7. Such cells are useful for screening compounds for therapeutic effect against prostate cancer. Methods for screening candidate compounds for therapeutic effect against prostate cancer are given in Example 15.

In another embodiment, methods are provided for conferring selective cytotoxicity in cells in which an hKLK2-TRE is functional, comprising contacting the cells with a delivery vehicle described herein, wherein the vehicle enters the cell. Preferably, the vehicle is a viral vector. Preferably, the viral vector is adenovirus. Cytotoxicity can be measured using standard assays in the art, such as dye exclusion, $^3$H-thymidine incorporation, and/or lysis.

In another embodiment, methods are provided for the selective transcription and/or expression of a heterologous polynucleotide in cells which the function of an hKLK2 enhancer is sufficiently preserved. By "sufficiently preserved", it is intended that transcription due to the presence of the enhancer is increased above basal levels (i.e., promoter alone; lacking enhancer) in the target cell by at least about 2-fold, preferably at least about 5-fold, preferably at least about 10-fold, more preferably at least about 20-fold, more preferably at least about 50-fold, more preferably at least about 100-fold, more preferably at least about 200-fold, even more preferably at least about 400- to about 500-fold, even more preferably at least about 1000-fold.

In particular, methods are provided for selective transcription and/or expression of a heterologous polynucleotide in cells which do not normally express the heterologous polynucleotide, or express the heterologous polynucleotide at undetectable levels. Expression of the heterologous polynucleotide by such cells can be detected in a variety of ways, including but not limited to, fluorescence-activated cell sorting (FACS) using one or more antibodies specific for a protein expressed on a cell surface (in situations in which the heterologous polynucleotide expresses a product which is expressed on the cell surface), enzyme-linked immunoassay (ELISA) of cell supernatants (for a secreted product of a heterologous polynucleotide), using an antibody specific for the secreted product.

Accordingly, the invention provides methods for increasing transcription of an operably linked polynucleotide sequence in a cell comprising introducing a construct comprising an hKLK2 enhancer and a promoter operably linked to said polynucleotide into a cell in which the hKLK2 enhancer is functional. Such cells have been described above, as have hKLK2 enhancers (i.e., polynucleotide sequences having enhancer activity).

Adenoviral Vectors Comprising an hKLK2-TRE

The present invention also provides adenoviral vector constructs which comprise an adenoviral gene under transcriptional control of an hKLK2-TRE. Preferably, the adenoviral gene is one that contributes to cytotoxicity (whether directly and/or indirectly), more preferably one that enhances cell death, and even more preferably the adenoviral gene under transcriptional control of an hKLK2-TRE is a gene essential for adenoviral replication. Examples of an adenoviral gene that contributes to cytotoxicity include, but are not limited to, an adenoviral death protein. When the adenovirus vector(s) is selectively (i.e. preferentially) replication-competent for propagation in target cells which allow the function of an hKLK2-TRE, these cells will be preferentially killed upon adenoviral proliferation. Preferably, target cells are prostate cells. By combining the adenovirus vector(s) with the mixture of prostate and non-prostate cells, in vitro or in vivo, the adenovirus vector(s) preferentially replicate in the target prostate cells. Once the target cells are destroyed due to selective cytotoxic and/or cytolytic replication, the adenovirus vector(s) replication is significantly reduced, lessening the probability of runaway infection and undesirable bystander effects. In vitro cultures may be retained to continually monitor the mixture (such as, for example, a biopsy or other appropriate biological sample) for occurrence (i.e. presence) and/or recurrence of the target cell, e.g., an androgen receptor-producing cancer cell. To ensure cytotoxicity further, one or more transgenes having a cytotoxic effect may also be present and under selective transcriptional control. In this embodiment, one may provide higher confidence that the target cells will be destroyed.

Accordingly, the invention provides an adenovirus vector comprising an adenovirus gene, preferably one that contributes to cytotoxicity (whether indirectly and/or directly), preferably one that contributes to and/or causes cell death, preferably one that is essential for adenoviral replication, under transcriptional control of an hKLK2-TRE.

In the context of adenovirus constructs, an hKLK2-TRE comprises an hKLK2 promoter, or an hKLK2 enhancer and a promoter, which may be an hKLK2 promoter, a heterologous promoter, for example, a promoter derived from the prostate-specific antigen gene, or a homologous promoter, i.e., an adenoviral promoter. EP 755,443 and U.S. Pat. No. 5,648,478 disclose the sequence of a prostate-specific enhancer and a promoter derived from the prostate-specific antigen (PSA) gene. hKLK-TRE have been described in a previous section. In one embodiment, an hKLK2-TRE comprises a region from about −323 to about +33 relative to the transcription start site of the hKLK2 gene (nucleotides about 11,290 to about 12,047 of SEQ ID NO:1). In another embodiment, an hKLK2-TRE is the sequence upstream of the hKLK2 coding region and comprises, for example, the polynucleotide sequence from about −607 to about +33 relative to the transcription start site of the hKLK2 gene (nucleotides about 11,407 to about 12,047 of SEQ ID NO:1).

In another embodiment, an hKLK2-TRE comprises nucleotides about −2247 to about +33 relative to the transcription start site (nucleotides about 9767 to about 12,047 of SEQ ID NO:1). An hKLK2 promoter has been previously described. Murtha et al. (1993); Schedlich et al. (1987). The hKLK2 promoter contains an androgen response element (ARE) located approximately −160 relative to the transcription start site. Removal of this ARE results in loss of androgen inducibility. The approximately 600 bp promoter region was demonstrated to be androgen responsive but was not inducible by estrogen, glucocorticoids or progestin. Murtha et al. (1993). Although 2.2 kb of 5' flanking sequence has been published (Schedlich et al. (1987)), no enhancer or promoter function associated with the sequences from about −600 to about −2256 has been described. As discussed above, and as shown in Example 7 and FIG. 11, a sequence having significant sequence identity to a consensus ARE is found at nucleotides −3822 to −3808 (nucleotides 8192 to 8206 of SEQ ID NO:1). Mutation of this sequence resulted in abolished enhancer activity.

An hKLK2-TRE can comprise any number of configurations, including, but not limited to, an hKLK2 promoter (comprising an ARE site) and an hKLK2 enhancer (preferably comprising an ARE, as described above); a non-hKLK2 promoter and an hKLK2 enhancer, and multimers of the foregoing as long as the desired hKLK2 cell-specific transcriptional activity is obtained. The promoter and enhancer components of an hKLK2-TRE may be in any orientation and/or distance from the coding sequence of interest, and comprise multimers of the foregoing, as long as the desired hKLK2 cell-specific transcriptional activity is obtained. Transcriptional enhancement can be measured in a number of ways known in the art (and described in more detail below), but is generally measured by detection and/or quantitation of mRNA or the protein product of the coding sequence under control of (i.e., operably linked to) an hKLK2-TRE. As discussed herein, an hKLK2-TRE can be of varying lengths, and of varying sequence composition. By transcriptional enhancement, it is intended that transcription due to the presence of the enhancer is increased above basal levels (i.e., promoter alone; lacking enhancer) in the target cell (i.e., a cell which allows an hKLK2 enhancer and/or an hKLK2-TRE to function) by at least about 2-fold, preferably at least about 5-fold, preferably at least about 10-fold, more preferably at least about 20-fold, more preferably at least about 50-fold, more preferably at least about 100-fold, more preferably at least about 200-fold, even more preferably at least about 400- to about 500-fold, even more preferably at least about 1000-fold. Basal levels are generally the level of activity, if any, in a a cell which does not allow an hKLK2 enhancer and/or an hKLK2-TRE to function, or the level of activity (if any) of a reporter construct lacking an hKLK2-TRE as tested in a cell which allows an hKLK2 enhancer and/or an hKLK2-TRE to function.

Maximal enhancer activity may not always be necessary to achieve a desired result. For example, as shown in Example 7, the 350-bp hKLK2 "core regulator" fragment (8021 to 8371 of SEQ ID NO:1; −3993 to −3643 relative to the transcription start site), when linked to the hKLK2 minimal promoter (−234 to +33 relative to the transcription start site) enhances activity of a luciferase-encoding gene in LNCaP cells in the presence of R1881 about 37-fold. The level of induction afforded by the 350-bp "core regulator" fragment may be sufficient in certain applications to achieve a desired result. For example, if an adenoviral vector of the invention is used to monitor cells for androgen receptor-producing activity, it is possible that less than maximal degree of responsiveness by an hKLK2-TRE will suffice to qualitatively indicate the presence of such cells. Similarly, if used for treatment or palliation of a disease state, less-than-maximal responsiveness may be sufficient for the desired result, if, for example, the androgen receptor-producing cells are not especially virulent and/or the extent of disease is relatively confined.

Various replication-competent adenovirus vectors can be made according to the present invention in which a single or multiple adenovirus gene(s) are under control of one or more hKLK2-TRE. Methods for generating such vectors are provided in Examples 8 to 10.

For example, an hKLK2-TRE may be introduced into an adenovirus vector immediately upstream of and operably linked to (i.e. oriented in such a way as to be able to drive expression of) an early gene such as E1A or E1B.

Various other replication-competent adenovirus vectors can be made according to the present invention in which, in addition to having an adenovirus gene(s) are under control of an hKLK2-TRE, other adenovirus gene(s) are under control of another heterologous (non-adenovirus) transcriptional control element. This TRE may be a tissue-specific promoter and/or enhancer, for instance the PSE (prostate-specific antigen enhancer) of the prostate specific antigen (PSA) gene, which is preferentially expressed in prostate cells. Lundwall et al. (1987) *FEBS Lett.* 214: 317; Lundwall (1989) *Biochem. Biophys. Res. Comm.* 161: 1151; and Riegmann et al. (1991) *Molec. Endocrin.* 5: 1921. A PSE is located between nt −5322 and nt −3739 relative to the transcriptional start site of the prostate specific antigen gene. Schuur et al. (1996) *J. Biol. Chem.* 271: 7043–7051. A PSA promoter comprises the sequence from about nt −540 to about nt +8 relative to the transcription start of the PSA gene. Juxtapositioning of these two genetic elements yields a fully functional minimal PSA-TRE. See European Patent Application No. EP 755,443 for the PSA promoter/enhancer region. Alternatively, a PSA-TRE can comprise a PSE and a heterologous promoter.

Accordingly, one embodiment provided by the invention is an adenovirus vector comprising a first gene under transcriptional control of a human glandular kallikrein (hKLK2) transcription regulatory element (hKLK2-TRE) and a second gene under transcriptional control of a PSA-TRE, wherein said hKLK2-TRE comprises an hKLK2 enhancer a promoter, or an hKLK2 promoter, and wherein said PSA-TRE comprises a prostate specific enhancer (PSE) and a promoter. The first gene could be a gene essential for viral replication, an adenoviral gene which contributes to cytotoxicity, or a heterologous polynucleotide. The second gene could be a heterologous polynucleotide, a gene essential for viral replication, or an adenoviral gene which contributes to cytotoxicity. Thus, various permutations are possible and self-evident.

For example, an hKLK2-TRE may be introduced into an adenovirus vector immediately upstream of and operably linked to an early gene such as E1A, and the PSE may be introduced immediately upstream of and operably linked to another early gene such as E1B. Alternatively, an hKLK2-TRE may be introduced upstream of and operably linked to E1B, while the PSE is introduced immediately upstream of and operably linked to E1A.

In some embodiments, the invention provides adenoviral vectors which comprise an additional adenovirus gene under transcriptional control of a second hKLK2-TRE. Examples of an additional adenovirus gene under transcriptional control is ADP (discussed herein) and genes necessary for replication, such as early genes. For example, an adenoviral vector can be constructed such that a first hKLK2-TRE regulates transcription of one early gene, such as E1A or E1B, and a second hKLK2-TRE regulates transcription of another early gene. These multiple constructs may be more desirable in that they provide more than one source of cell specificity with respect to replication.

In one embodiment, E1A and E1B are under control of one or more hKLK2-TREs by making the following construct. A fragment containing the coding region of E1A through the E1B promoter is excised from the Ad genome and reinserted in opposite orientation. In this configuration, the E1A and E1B promoters are next to each other, followed by E1A in opposite orientation (so that neither the E1A or E1B promoters are operatively linked to E1A), followed by E1B in opposite orientation with respect to E1A. An hKLK2-TRE(s) can be inserted between E1A and E1B coding regions, (which are in opposite orientation), so that these regions are under control of the TRE(s). Appropriate promoter sequences are inserted proximal to the E1A and E1B region. Thus, an hKLK2-TRE may drive both E1A and E1B. Such a configuration may prevent, for example, possible loop-out events that may occur if two hKLK2-TREs were inserted in intact (native) Ad genome, one each 5' of the coding regions of E1A and E1B. By introducing a polycloning site between E1A and E1B, other types of TREs can be inserted, such as a carcinogen embryonic antigen TRE (CEA-TRE); a mucin TRE (MU-TRE); or other cell-specific regulatory elements, preferably those associated with a disease state, such as neoplasm. Thus, this construct may find general use for cell-specific, temporal, or other means of control of adenovirus genes E1A and E1B, thereby providing a convenient and powerful way to render adenoviral replication dependent upon a chosen transcriptional parameter.

Various other replication-competent adenovirus vectors can be made according to the present invention in which, in addition to having a single or multiple adenovirus gene(s) are under control of an hKLK2-TRE, reporter gene(s) are under control of an hKLK2-TRE.

For example, an hKLK2-TRE may be introduced into an adenovirus vector immediately upstream of and operably linked to an early gene such as E1A or E1B, and this construct may also contain a second hKLK2-TRE driving expression of a reporter gene encoding a reporter protein, including, but not limited to, chloramphenicol acetyl transferase (CAT), β-galactosidase (encoded by the lacZ gene), luciferase, alkaline phosphatase, green fluorescent protein, and horse radish peroxidase.

The size of an hKLK2-TRE will be determined in part by the capacity of the adenoviral vector, which in turn depends upon the contemplated form of the vector (see below). Generally a minimal size is preferred, as this provides potential room for insertion of other sequences which may be desirable, such as transgenes (discussed below) or other additional regulatory sequences. However, if no additional sequences are contemplated, or if, for example, an adenoviral vector will be maintained and delivered free of any viral packaging constraints, a larger DNA sequence may be used as long as the resultant adenoviral vector is rendered replication-competent.

If no adenovirus sequences have been deleted, an adenoviral vector can be packaged with extra sequences totaling up to about 5% of the genome size, or approximately 1.8 kb. If non-essential sequences are removed from the adenovirus genome, an additional 4.6 kb of insert can be tolerated (i.e., a total of about 1.8 kb plus 4.6 kb, which is about 6.4 kb). Examples of non-essential adenoviral sequences that can be deleted are E3 and E4 (as long as the E4 ORF6 is maintained).

In order to minimize non-specific replication, endogenous (i.e., adenovirus) TREs should preferably be removed. This would also provide more room for inserts in an adenoviral vector, which may be of special concern if an adenoviral vector will be packaged as a virus (see below). Even more importantly, deletion of endogenous TREs would prevent a possibility of a recombination event whereby an hKLK2-TRE is deleted and the endogenous TRE assumes transcriptional control of its respective adenovirus coding sequences (thus allowing non-specific replication). In one embodiment, an adenoviral vector of the invention is constructed such that the endogenous transcription control sequences of an adenoviral gene(s) are deleted and replaced by an hKLK2-TRE. However, endogenous TREs may be maintained in the adenovirus vector(s), provided that sufficient cell-specific replication preference is preserved. These embodiments can be constructed by providing an hKLK2-TRE intervening between the endogenous TRE and the replication gene coding segment. Requisite cell-specific replication preference is indicated by conducting assays that compare replication of the adenovirus vector in a cell which allows function of an hKLK2-TRE with replication in a cell which does not. Generally, it is intended that replication is increased above basal levels in the target cell (i.e., AR-producing cell) by at least about 2-fold, preferably at least about 5-fold, preferably at least about 10-fold more preferably at least about 20-fold, more preferably at least about 50-fold, more preferably at least about 100-fold, more preferably at least about 200-fold, even more preferably at least about 400- to about 500-fold, even more preferably at least about 1000-fold. The acceptable differential can be determined empirically (using, for example, Northern assays or other known in the art) and will depend upon the anticipated use of the adenoviral vector and/or the desired result.

Any of the various serotypes of adenovirus can be used, such as Ad2, Ad5, Ad12, and Ad40. For purposes of illustration, the serotype Adenovirus 5 (Ad5) is exemplified herein.

When an hKLK2-TRE is used with an adenovirus gene that is essential for propagation, replication competence is preferentially achievable in the target cells which allow for function of an hKLK2-TRE. Preferably, the gene is an early gene, such as E1A, E1B, E2, or E4. (E3 is not essential for viral replication.) More preferably, the early gene under hKLK2-TRE control is E1A and/or E1B. More than one early gene can be placed under control of an hKLK2-TRE. Examples 8 to 10 provides a more detailed description of such constructs.

The E1A gene is expressed immediately after viral infection (0–2 hours) and before any other viral genes. E1A protein acts as a trans-acting positive-acting transcriptional regulatory factor, and is required for the expression of the other early viral genes E1B, E2, E3, E4, and the promoter-proximal major late genes. Despite the nomenclature, the promoter proximal genes driven by the major late promoter are expressed during early times after Ad5 infection. Flint (1982) *Biochem. Biophys. Acta* 651:175–208; Flint (1986) *Advances Virus Research* 31:169–228; Grand (1987) *Biochem. J.* 241:25–38. In the absence of a functional E1A gene, viral infection does not proceed, because the gene products necessary for viral DNA replication are not produced. Nevins (1989) *Adv. Virus Res.* 31:35–81. The transcription start site of Ad5 E1A is at nt 498 and the ATG start site of the E1A protein is at nt 560 in the virus genome.

The E1B protein functions in trans and is necessary for transport of late mRNA from the nucleus to the cytoplasm. Defects in E1B expression result in poor expression of late viral proteins and an inability to shut off host cell protein synthesis. The promoter of E1B has been implicated as the defining element of difference in the host range of Ad40 and Ad5: clinically Ad40 is an enterovirus, whereas Ad5 causes acute conjunctivitis. Bailey et al. (1993) *Virology* 193:631; Bailey et al. (1994) *Virology* 202:695–706. The E1B promoter of Ad5 consists of a single high-affinity recognition site for Sp1 and a TATA box.

The E2 region of adenovirus codes for proteins related to replication of the adenoviral genome, including the 72 kDa DNA-binding protein, the 80 kDa precursor terminal protein and the viral DNA polymerase. The E2 region of Ad5 is transcribed in a rightward orientation from two promoters, termed E2 early and E2 late, mapping at 76.0 and 72.0 map units, respectively. While the E2 late promoter is transiently active during late stages of infection and is independent of the E1A transactivator protein, the E2 early promoter is crucial during the early phases of viral replication.

The E2 early promoter, mapping in Ad5 from 27050–27150, consists of a major and a minor transcription initiation site, the latter accounting for about 5% of the E2 transcripts, two non-canonical TATA boxes, two E2F transcription factor binding sites and an ATF transcription factor binding site.

For a detailed review of the E2 promoter architecture see Swaminathan et al., *Curr. Topics in Micro. and Imm.* (1995) 199 part 3:177–194.

The E2 late promoter overlaps with the coding sequences of a gene encoded by the counterstrand and is therefore not amenable for genetic manipulation. However, the E2 early promoter overlaps only for a few base pairs with sequences coding for a 33 kDa protein on the counterstrand. Notably, the SpeI restriction site (Ad5 position 27082) is part of the stop codon for the above mentioned 33 kDa protein and conveniently separates the major E2 early transcription initiation site and TATA-binding protein site from the upstream transcription factor binding sites E2F and ATF. Therefore, insertion of an hKLK2-TRE having SpeI ends into the SpeI site in the plus strand would disrupt the endogenous E2 early promoter of Ad5 and should allow AR-restricted expression of E2 transcripts.

The E4 gene has a number of transcription products. The E4 region codes for two polypeptides which are responsible for stimulating the replication of viral genomic DNA and for stimulating late gene expression. The protein products of open reading frames (ORFs) 3 and 6 can both perform these functions by binding the 55-kDa protein from E1B and heterodimers of E2F-1 and DP-1. The ORF 6 protein requires interaction with the E1B 55-kDa protein for activity while the ORF 3 protein does not. In the absence of functional protein from ORF 3 and ORF 6, plaques are produced with an efficiency less than $10^{-6}$ that of wild type virus. To restrict further the viral replication to AR-producing cells, E4 ORFs 1–3 can be deleted, making viral DNA replication and late gene synthesis dependent on E4 ORF 6 protein. By combining such a mutant with sequences in which the E1B region is regulated by an hKLK2-TRE, a virus can be obtained in which both the E1B function and E4 function are dependent on an hKLK2-TRE driving E1B.

The major late genes relevant to the subject invention are L1, L2 and L3, which encode proteins of the Ad5 virus virion. All of these genes (typically coding for structural proteins) are probably required for adenoviral replication. The late genes are all under the control of the major late promoter (MLP), which is located in Ad5 at +5986 to +6048.

In addition to conferring selective cytotoxic and/or cytolytic activity by virtue of preferential replication competence in cells which allow function of an hKLK2-TRE, the adenovirus vectors of this invention can further include a heterologous polynucleotide (transgene) under the control of an hKLK2-TRE. In this way, various genetic capabilities may be introduced into target cells, particularly prostate carcinoma cells. For example, in certain instances, it may be desirable to enhance the degree and/or rate of cytotoxic activity, due to, for example, the relatively refractory nature or particular aggressiveness of the target cell. This could be accomplished by coupling the cell-specific replicative cytotoxic activity with cell-specific expression of, for example, HSV-tk and/or cytosine deaminase (cd), which renders cells capable of metabolizing 5-fluorocytosine (5-FC) to the chemotherapeutic agent 5-fluorouracil (5-FU). Using these types of transgenes may also confer a bystander effect.

Other desirable transgenes that may be introduced via an adenovirus vector(s) include genes encoding cytotoxic proteins, such as the A chains of diphtheria toxin, ricin or abrin [Palmiter et al. (1987) *Cell* 50: 435; Maxwell et al. (1987) *Mol. Cell. Biol.* 7: 1576; Behringer et al. (1988) *Genes Dev.* 2: 453; Messing et al. (1992) *Neuron* 8: 507; Piatak et al. (1988) *J. Biol. Chem.* 263: 4937; Lamb et al. (1985) *Eur. J. Biochem.* 148: 265; Frankel et al. (1989) *Mol. Cell. Biol.* 9: 415], genes encoding a factor capable of initiating apoptosis, sequences encoding antisense transcripts or ribozymes, which among other capabilities may be directed to mRNAs encoding proteins essential for proliferation, such as structural proteins, or transcription factors; viral or other pathogenic proteins, where the pathogen proliferates intracellularly, genes that encode an engineered cytoplasmic variant of a nuclease (e.g. RNase A) or protease (e.g. awsin, papain, proteinase K, carboxypeptidase, etc.), or encode the Fas gene, and the like. Other genes of interest include cytokines, antigens, transmembrane proteins, and the like, such as IL-1,-2,-6,-12, GM-CSF, G-CSF, M-CSF, IFN-$\alpha$, -$\beta$, -$\gamma$, TNF-$\alpha$, -$\beta$, TGF-$\alpha$, -$\beta$, NGF, and the like. The positive effector genes could be used in an early phase, followed by cytotoxic activity due to replication.

In some embodiments, the adenovirus death protein (ADP), encoded within the E3 region, is maintained (i.e., is contained) in the adenovirus vector. The ADP gene, under control of the major late promoter (MLP), appears to code for a protein (ADP) that is important in expediting host cell lysis. Tollefson et al. (1996) *J. Virol.* 70(4):2296; Tollefson et al. (1992) *J. Virol.* 66(6):3633. Thus, adenoviral vectors containing the ADP gene may render the adenoviral vector more potent, making possible more effective treatment and/or a lower dosage requirement.

Accordingly, the invention provides adenoviral vectors that include a polynucleotide sequence encoding an ADP. A DNA sequence encoding an ADP and the amino acid sequence of an ADP are depicted in (SEQ ID NO:4 and SEQ ID NO:5), respectively. Briefly, an ADP coding sequence is obtained preferably from Ad2 (since this is the strain in which ADP has been more fully characterized) using techniques known in the art, such as PCR. Preferably, the Y leader (which is an important sequence for correct expression of late genes) is also obtained and ligated to the ADP coding sequence. The ADP coding sequence (with or without the Y leader) can then be introduced into the adenoviral genome, for example, in the E3 region (where the ADP coding sequence will be driven by the MLP or the E3 promoter). The ADP coding sequence could also be inserted in other locations of the adenovirus genome, such as the E4 region. Alternatively, the ADP coding sequence could be operably linked to a heterologous promoter (with or without enhancer(s)), including, but not limited to, another viral promoter, a tissue specific promoter such as AFP, carcinoembryonic antigen (CEA), hKLK2, mucin, and rat probasin.

The adenoviral vectors can be used in a variety of forms, including, but not limited to, naked polynucleotide (usually DNA) constructs; polynucleotide constructs complexed with agents to facilitate entry into cells, such as cationic liposomes or other compounds such as polylysine; packaged into infectious adenovirus particles (which may render the adenoviral vector(s) more immunogenic); packaged into other particulate viral forms such as HSV or AAV; complexed with agents to enhance or dampen an immune response; complexed with agents that facilitate in vivo transfection, such as DOTMA™, DOTAP™, and polyamines; or in the form of any of the delivery vehicles described herein.

If an adenoviral vector is packaged into an adenovirus, the adenovirus itself may be selected to further enhance targeting. For example, adenovirus fibers mediate primary contact with cellular receptor(s) aiding in tropism. See, e.g., Amberg et al. (1997) *Virol.* 227:239–244. If a particular subgenus of an adenovirus serotype displayed tropism for a target cell type and/or reduced affinity for non-target cell types, such subgenus (or subgenera) could be used to further increase cell-specificity of cytotoxicity and/or cytolysis.

The invention also provides an adenovirus vector comprising an hKLK2 enhancer, wherein the adenovirus vector is capable of replicating preferentially in a cell which allows an hKLK2 enhancer and/or an hKLK2-TRE to function. "Replicating preferentially in a cell which allows an hKLK2 enhancer and/or an hKLK2-TRE to function" means that the adenovirus replicates more in a cell producing all the factors and co-factors needed to allow an hKLK2 enhancer and a promoter to increase transcription of an operably linked polynucleotide than in a cell not producing such factors and co-factors. Preferably, the adenovirus replicates at a significantly higher level in a cell which allows an hKLK2 enhancer and/or an hKLK2-TRE to function than in a cell which does not allow an hKLK2 enhancer and/or an hKLK2-TRE to function; preferably, at least about 2-fold higher, preferably at least about 5-fold higher, more preferably at least about 10-fold higher, still more preferably at least about 50-fold higher, even more preferably at least about 100-fold higher, still more preferably at least about 400-to about 500-fold higher, still more preferably at least about 1000-fold higher, most preferably at least about $1 \times 10^6$ higher. Most preferably, the adenovirus replicates solely in a cell which allows an hKLK2 enhancer and/or an hKLK2-TRE to function (that is, does not replicate or replicates at very low levels in a cell which does not allow an hKLK2 enhancer and/or an hKLK2-TRE to function).

Host Cells and Target Cells

The present invention also provides host cells comprising (i.e., transformed with) the adenoviral vectors described herein. Both prokaryotic and eukaryotic host cells can be used as long as sequence requisite for maintenance in that host, such as appropriate replication origin(s), are present. For convenience, selectable markers are also provided. Prokaryotic host include bacterial cells, for example, *E. coli* and mycobacteria. Among eukaryotic host cells are yeast, insect, avian, amphibian, plant and mammalian host cells. Host systems are known in the art and need not be described in detail herein.

The present invention also provides target cells comprising (i.e., transformed with) the adenoviral vectors described herein. Suitable target cells for the adenovirus include any eukaryotic cell type that allows function of an hKLK2 enhancer and/or an hKLK2-TRE, preferably mammalian, which may or may not be prostate cells. Preferably, the cells are prostate cells or cells derived from the prostate, for example LNCaP cells. Preferably, the cells used produce endogenous androgen receptor. Suitable target cells also include any cells that produce proteins and other factors necessary for expression of the polynucleotide under control of the hKLK2-TRE, which may be an AR, whether the AR and/or other factors are produced naturally or recombinantly. Suitable target cells are those which allow an hKLK2 enhancer and/or an hKLK2-TRE to function. Such cells can be identified and/or characterized by their ability to allow an hKLK2 enhancer and/or an hKLK2-TRE to function.

Comparisons between or among various hKLK2-TREs can be assessed by measuring and comparing levels of expression within a single cell line which allows an hKLK2 enhancer and/or an hKLK2-TRE to function. It is understood that absolute transcriptional activity of an hKLK2-TRE will depend on several factors, such as the nature of the target cell, delivery mode and form of an hKLK2-TRE, and the coding sequence whose transcription is to be increased. To compensate for various plasmid sizes used, activities can be expressed as relative activity per mole of transfected plasmid. Alternatively, the level of transcription (i.e., mRNA) can be measured using standard Northern analysis and hybridization techniques. Levels of transfection (i.e., transfection efficiencies) are measured by co-transfecting a plasmid encoding a different reporter gene under control of a different TRE, such as the CMV immediate early promoter. This analysis can also indicate negative regulatory regions, i.e., silencers.

The adenoviral vectors may be delivered to a target cell in a variety of forms, including, but not limited to, any of the delivery vehicles described above, and in a variety of ways, including, but not limited to, general transfection methods that are well known in the art (such as calcium phosphate precipitation and electroporation), direct injection, and intravenous infusion. The means of delivery will depend in large part on the particular adenoviral vector (including its form) as well as the type and location of the target cells (i.e., whether the cells are in vitro or in vivo).

If used in a packaged adenovirus, adenovirus vectors may be administered in an appropriate physiologically acceptable carrier at a dose of about $10^4$ to about $10^{14}$. The multiplicity of infection will generally be in the range of about 0.001 to 100. If administered as a polynucleotide construct (i.e., not packaged as a virus) about 0.01 µg to 1000 µg of an adenoviral vector can be administered. The adenoviral vectors may be administered one or more times, depending upon the intended use and the immune response potential of the host or may be administered as multiple simultaneous injections. If an immune response is undesirable, the immune response may be diminished by employing a variety of immunosuppressants, so as to permit repetitive administration, without a strong immune response. If packaged as another viral form, such as HSV, an amount to be administered is based on standard knowledge about that particular virus (which is readily obtainable from, for example, published literature) and can be determined empirically.

The present invention also includes compositions, including pharmaceutical compositions, containing the adenoviral vectors described herein. Such compositions are useful for administration in vivo, for example, when measuring the degree of transduction and/or effectiveness of cell killing in an individual. Preferably, these compositions further comprise a pharmaceutically acceptable excipient. These compositions, which can comprise an effective amount of an adenoviral vector of this invention in a pharmaceutically acceptable excipient, are suitable for systemic administration to individuals in unit dosage forms, sterile parenteral solutions or suspensions, sterile non-parenteral solutions or oral solutions or suspensions, oil in water or water in oil emulsions and the like. Formulations for parenteral and nonparenteral drug delivery are known in the art and are set forth in *Remington's Pharmaceutical Sciences*, $18^{th}$ Edition, Mack Publishing (1990). Compositions also include lyophilized and/or reconstituted forms of the adenoviral vectors (including those packaged as a virus, such as adenovirus) of the invention.

The present invention also encompasses kits containing an adenoviral vector of this invention. These kits can be used for diagnostic and/or monitoring purposes, preferably monitoring. Procedures using these kits can be performed by clinical laboratories, experimental laboratories, medical practitioners, or private individuals. Kits embodied by this invention allow someone to detect the presence of androgen receptor-producing cells in a suitable biological sample, such as biopsy specimens.

The kits of the invention comprise an adenoviral vector described herein in suitable packaging. The kit may optionally provide additional components that are useful in the procedure, including, but not limited to, buffers, developing reagents, labels, reacting surfaces, means for detection, control samples, instructions, and interpretive information.

Preparation of the Adenovirus Vectors of the Invention

The adenovirus vectors of this invention can be prepared using recombinant techniques that are standard in the art. Generally, an hKLK2-TRE is inserted 5' to the adenoviral gene of interest, preferably an adenoviral gene which contributes to cytoxicity, which can be one or more early genes (although late gene(s) may be used). An hKLK2-TRE can be prepared using oligonucleotide synthesis (if the sequence is known) or recombinant methods (such as PCR and/or restriction enzymes). Convenient restriction sites, either in the natural adeno-DNA sequence or introduced by methods such as PCR or site-directed mutagenesis, provide an insertion site for an hKLK2-TRE. Accordingly, convenient restriction sites for annealing (i.e., inserting) an hKLK2-TRE can be engineered onto the 5' and 3' ends of an hKLK2-TRE using standard recombinant methods, such as PCR.

Polynucleotides used for making adenoviral vectors of this invention may be obtained using standard methods in the art such as chemical synthesis recombinant methods and/or obtained from biological sources.

Adenoviral vectors containing all replication-essential elements, with the desired elements (e.g. E1A) under control of an hKLK2-TRE, are conveniently prepared by homologous recombination or in vitro ligation of two plasmids, one providing the left-hand portion of adenovirus and the other providing the right-hand portion, one or both of which contains at least one adenovirus gene under control of an hKLK2-TRE. If homologous recombination is used, the two plasmids should share at least about 500 bp of sequence overlap. Each plasmid, as desired, may be independently manipulated, followed by cotransfection in a competent host, providing complementing genes as appropriate, or the appropriate transcription factors for initiation of transcription from an hKLK2-TRE for propagation of the adenovirus. Plasmids are generally introduced into a suitable host cell such as 293 cells or LNCaP cells, etc., using appropriate means of transduction, such as cationic liposomes. Alternatively, in vitro ligation of the right and left-hand portions of the adenovirus genome can be used to construct recombinant adenovirus derivative containing all the replication-essential portions of adenovirus genome. Berkner et al. (1983) *Nucleic Acid Research* 11:6003–6020; Bridge et al. (1989) *J. Virol* 63:631–638.

For convenience, plasmids are available that provide the necessary portions of adenovirus. Plasmid pXC.1 (McKinnon (1982) *Gene* 19:33–42) contains the wild-type left-hand end of Ad5, from Adenovirus 5 nt 22 to 5790. pBHG10 (Bett et al. (1994) *Proc. Natl. Acad. Sci. USA* 91:8802–8806; Microbix Biosystems Inc., Toronto) provides the right-hand end of Ad5, with a deletion in E3. The deletion in E3 provides room in the virus to insert a 3-kb hKLK2-TRE without deleting the endogenous enhancer-promoter. The gene for E3 is located on the opposite strand from E4 (r-strand). pBHG11 [Bett. et al. (1994)] provides an even larger E3 deletion (an additional 0.3 kb is deleted).

For manipulation of the early genes, the transcription start site of Ad5 E1A is at nt 498 and the ATG start site of this gene's coding segment is at nt 560 in the virus genome. This region can be used for insertion of an hKLK2-TRE. A restriction site may be introduced by employing PCR, where the primer that is employed may be limited to the Ad5 genome, or may involve a portion of the plasmid carrying the Ad5 genomic DNA. For example, where pBR322 is used, the primers may use the EcoRI site in the pBR322 backbone and the XbaI site at nt 1339 of Ad5. By carrying out the PCR in two steps, where overlapping primers at the center of the region introduce a 30 sequence change resulting in a unique restriction site, one can provide for insertion of an hKLK2-TRE at that site.

A similar strategy may be used for insertion of an hKLK2-TRE to regulate E1B. The E1B promoter of Ad5 consists of a single high-affinity recognition site for Sp1 and a TATA box. This region extends from Ad5 nt 1636 to 1701. By insertion of an hKLK2-TRE in this region, one can provide for cell-specific transcription of the E1B gene. By employing the left-hand region modified with the cell-specific response element regulating E1A, as the template for introducing an hKLK2-TRE to regulate E1B, the resulting adenovirus vector will be dependent upon the cell-specific transcription factors for expression of both E1A and E1B. Example 9 provides a more detailed description of how such constructs can be prepared.

Similarly, an hKLK2-TRE may be inserted upstream of the E2 gene to make its expression cell-specific. The E2 early promoter, mapping in Ad5 from 27050–27150, consists of a major and a minor transcription initiation site, the latter accounting for about 5% of the E2 transcripts, two non-canonical TATA boxes, two E2F transcription factor binding sites and an ATF transcription factor binding site (for a detailed review of the E2 promoter architecture see Swaminathan et al., *Curr. Topics in Microbiol. and Immunol.* (1995) 199 part 3:177–194.

The E2 late promoter overlaps with the coding sequences of a gene encoded by the counterstrand and is therefore not amenable to genetic manipulation. However, the E2 early promoter overlaps only for a few base pairs with sequences coding for a 33-kDa protein on the counterstrand. Notably, the SpeI restriction site (Ad5 position 27082) is part of the stop codon for the above mentioned 33 kDa protein and conveniently separates the major E2 early transcription initiation site and TATA-binding protein site from the upstream transcription factor biding sites E2F and ATF. Therefore, insertion of an hKLK2-TRE having SpeI ends into the SpeI site in the plus-strand would disrupt the endogenous E2 early promoter of Ad5 and should allow AR-restricted expression of E2 transcripts.

For E4, one must use the right hand portion of the adenovirus genome. The E4 transcription start site is predominantly at nt 35609, the TATA box at nt 35638 and the first AUG/CUG of ORF1 is at nt 35532. Virtanen et al. (1984) *J. Virol.* 51: 822–831. Using any of the above strategies for the other genes, an hKLK2-TRE may be introduced upstream from the transcription start site. For the construction of mutants in the E4 region, the co-transfection and homologous recombination are performed in W162 cells (Weinberg et al. (1983) *Proc. Natl. Acad. Sci. USA* 80:5383–5386) which provide E4 proteins in trans to complement defects in synthesis of these proteins. Methods of packaging adenovirus polynucleotides into adenovirus particles are known in the art and are described in the Examples.

Methods Using the Adenovirus Vectors of the Invention

The subject adenoviral vectors can be used for a wide variety of purposes, which will vary with the desired or intended result. Accordingly, the present invention includes methods using the adenoviral vectors described above.

In one embodiment, methods are provided for conferring selective cytotoxicity in cells which allow function of an hKLK2 enhancer and/or an hKLK2-TRE, comprising contacting cells, preferably mammalian cells, preferably androgen receptor-producing cells, with an adenovirus vector described herein, such that the adenovirus vector(s) enters, i.e., transduces the cell(s). Cytotoxicity can be measured using standard assays in the art, such as dye exclusion, $^3$H-thymidine incorporation, and/or lysis.

In another embodiment, methods are provided for propagating an adenovirus specific for cells, preferably mammalian cells, which allow function of an hKLK2 enhancer and/or an hKLK2-TRE. These methods entail combining an adenovirus vector with cells, preferably mammalian cells, which allow function of an hKLK2 enhancer and/or an hKLK2-TRE, whereby said adenovirus is propagated.

Another embodiment provides methods of killing cells that allow a PB-TRE to function, such as cells expressing the androgen receptor in a mixture of cells, comprising combining the mixture of cells with an adenovirus vector of the present invention. The mixture of cells is generally a mixture of normal cells and cancerous cells producing androgen receptor, and can be an in vivo mixture or in vitro mixture.

The invention also includes methods for detecting, in a biological sample, cells which allow an hKLK2 enhancer and/or an hKLK2-TRE to function. These methods are particularly useful for monitoring the clinical and/or physiological condition of an individual (i.e., mammal), whether in an experimental or clinical setting. For these methods, cells of a biological sample are contacted with an adenovirus vector of the invention, and replication of the adenoviral vector, or expression of a polynucleotide contained within the adenoviral vector whose product can produce a detectable signal, is detected. A suitable biological sample is one in which cells which allow an hKLK2 enhancer and/or an hKLK2-TRE to function may be or are suspected to be present. Generally, in mammals, a suitable clinical sample is one in which cancerous cells which allow an hKLK2 enhancer and/or an hKLK2-TRE to function, such as prostate cancer cells, are suspected to be present. Such cells can be obtained, for example, by needle biopsy or other surgical procedure. Cells to be contacted may be treated to promote assay conditions such as selective enrichment and/or solubilization. In these methods, cells which allow an hKLK2 enhancer and/or an hKLK2-TRE to function can be detected using in vitro assays that detect proliferation, which are standard in the art. Examples of such standard assays include, but are not limited to, burst assays (which measure virus yields) and plaque assays (which measure infectious particles per cell). Also, propagation can be detected by measuring specific adenoviral DNA replication, which are also standard assays. Alternatively, cells which allow an hKLK2 enhancer and/or an hKLK2-TRE to function can be detected if the adenoviral vector comprises a polynucleotide whose expression product can produce a detectable signal. Examples include reporter genes, as described herein.

The invention also provides methods of modifying the genotype of a target cell, comprising contacting the target cell with an adenovirus vector described herein, wherein the adenoviral vector enters the cell.

The invention further provides methods of suppressing tumor cell growth, comprising contacting a tumor cell with an adenoviral vector of the invention such that the adenoviral vector enters the tumor cell and exhibits selective cytotoxicity for the tumor cell. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying and stopping tumor growth, as well as tumor shrinkage. "Suppressing" tumor growth indicates a growth state that is curtailed when compared to growth without contact with, i.e., transfection by, an adenoviral vector of the invention.

The invention also provides methods of lowering the levels of a tumor cell marker in an individual, comprising administering to the individual an adenoviral vector of the present invention, wherein the adenoviral vector is selectively cytotoxic toward cells producing the tumor cell marker. Tumor cell markers include, but are not limited to, PSA, carcinoembryonic antigen and hK2. Methods of measuring the levels of a tumor cell marker are known to those of ordinary skill in the art and include, but are not limited to, immunological assays, such as enzyme-linked immunosorbent assay (ELISA), using antibodies specific for the tumor cell marker. In general, a biological sample is obtained from the individual to be tested, and a suitable assay, such as an ELISA, is performed on the biological sample.

The invention also provides methods of treatment, in which an effective amount of an adenoviral vector(s) described herein is administered to an individual. Treatment using an adenoviral vector(s) is indicated in individuals with tumors such as prostate carcinoma. Also indicated are individuals who are considered to be at risk for developing prostate-associated diseases, such as those who have had disease which has been resected and those who have had a family history of prostate-associated diseases. Determination of suitability of administering adenoviral vector(s) of the invention will depend, inter alia, on assessable clinical parameters such as serological indications and histological examination of tissue biopsies. Generally, a pharmaceutical composition comprising an adenoviral vector(s) is administered. Pharmaceutical compositions are described above.

The amount of adenoviral vector(s) to be administered will depend on several factors, such as route of administration, the condition of the individual, the degree of aggressiveness of the disease, the particular hKLK2-TRE employed, and the particular vector construct (i.e., which adenovirus gene(s) is under hKLK2-TRE control).

If administered as a packaged adenovirus, from about $10^4$ to about $10^{14}$, preferably from about $10^4$ to about $10^{12}$, more preferably from about $10^4$ to about $10^{10}$. If administered as a polynucleotide construct (i.e., not packaged as a virus), about 0.01 μg to about 100 μg can be administered, preferably 0.1 μg to about 500 μg, more preferably about 0.5 μg to about 200 μg. More than one adenoviral vector can be administered, either simultaneously or sequentially. Administrations are typically given periodically, while monitoring any response.

The adenoviral vectors of the invention can be used alone or in conjunction with other active agents, such as chemotherapeutics, that promote the desired objective.

Screening Methods Utilizing an hKLK2-TRE

The present invention provides methods for screening compounds for the treatment of prostate cancer employing cells, preferably mammalian cells, comprising an expression construct. The expression construct comprises an hKLK2 transcriptional regulatory element (hKLK2-TRE) and a reporter gene whose expression product provides a detectable signal. The hKLK2-TRE comprises an hKLK2 and a promoter, and the reporter gene is under the transcriptional control of an hKLK2-TRE. The method comprises the steps of:

a) combining cells with a candidate compound in the presence of an appropriate inducing agent for a sufficient time for detectable expression of the reporter gene; and b) detecting the level of expression of the reporter gene as compared to the level of expression in the absence of the candidate compound.

The screening methods involve introducing an expression construct comprising an hKLK2-TRE operably linked to a reporter gene into cells which allow an hKLK2 enhancer to function. An hKLK2-TRE can be operably linked to a reported gene and inserted into a variety of vectors. Host cells are then transfected or transformed with vectors containing an hKLK2-TRE linked to a reporter gene and cultured in conventional nutrient media modified as appropriate for selecting transformants, for example.

Cell-based screening assays of the present invention can be designed, e.g., by constructing cell lines in which the expression of a reporter protein, i.e., an easily assayable protein, such as β-galactosidase, chloramphenicol acetyltransferase (CAT), green fluorescent protein (GFP) or luciferase, is dependent on the function of an hKLK2-TRE. For example, a DNA construct comprising an hKLK2-TRE may be operably linked to a gene encoding luciferase as described in Example 2. The resulting DNA construct comprising the luciferase-encoding DNA is stably or transiently transfected into a host cell (see Example 3). The cell is exposed to a test compound and an appropriate inducing agent, such as an androgen, and, after a time sufficient to effect luciferase expression, the cells are assayed for the production of luciferase by standard enzyme assays (see Example 3).

An hKLK2-TRE comprises an hKLK2 enhancer and a promoter. For the screening methods described herein, an hKLK2 enhancer includes an isolated polynucleotide sequence comprising nucleotides about 8021 to about 8371 of SEQ ID NO:1 (corresponding to about −3993 to about −3643 relative to the hKLK2 transcription start site) and active fragments thereof. It also includes an isolated polynucleotide sequence comprising nucleotides about 7200 to about 8371 of SEQ ID NO:1 (corresponding to about −4814 to about −3643 relative to the hKLK2 transcription start site) and active fragments thereof. The promoter portion of the hKLK2-TRE may be heterologous or may be an hKLK2 promoter.

Reporter genes which may be employed are known to those skilled in the art and include, but are not limited to, luciferase; aequorian (i.e., green fluorescent protein from *Aequorea victoria*); β-galactosidase, chloramphenicol acetyl transferase; immunologically detectable protein "tags" such as human growth hormone; and the like. See, for example, Current Protocols in Molecular Biology (F. M. Ausubel et al., eds., 1987) and periodic updates. Any assay which detects a product of the reporter gene, either by directly detecting the protein encoded by the reporter gene or by detecting an enzymatic product of a reporter gene-encoded enzyme, is suitable for use in the present invention. Assays include calorimetric, fluorimetric, or luminescent assays or even, in the case of protein tags, radioimmunoassays or other immunological assays.

A recombinant polynucleotide comprising an hKLK2-TRE or active fragment thereof, as well as those which may comprise other hKLK2 transcriptional regulatory elements described herein, may be prepared by any technique to those of skill in the art using the sequence information provided herein.

A construct may be incorporated into a suitable vector for the purposes of propagation or expression. Such vectors include prokaryotic plasmids, eukaryotic plasmids and viral vectors, and the choice of vector depends upon the design of the screening assay, the cell types involved and other factors. Expression constructs comprising an hKLK2-TRE include plasmid and viral vectors, particularly adenovirus vectors, as described herein, in which the hKLK2-TRE comprises about 8021 to about 8371 of SEQ ID NO:1 (corresponding to about −3993 to about −3643 relative to the hKLK2 transcription start site) and active fragments thereof and about 7200 to about 8371 of SEQ ID NO:1 (corresponding to about −4814 to about −3643 relative to the hKLK2 transcription start site) and active fragments thereof.

For preparing an expression construct comprising an hKLK2-TRE operably linked to a reporter gene for use in the screening methods of the present invention, a polynucleotide comprising an hKLK2-TRE operably linked to a reporter gene can be inserted into a suitable vector, and the vector in turn can be introduced into a suitable host cell for replication and amplification. Polynucleotides may be inserted into host cells by any means known in the art. Cells are transformed by introducing an exogenous polynucleotide by direct uptake, endocytosis, transfection, f-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

The cells which are suitable for use in the methods of the present invention with respect to screening of compounds for possible therapeutic use in treatment of prostate cancer are any eukaryotic cells, preferably mammalian cells, which allow an hKLK2-TRE to function. Preferably, the cells are prostate cells, more preferably expressing androgen receptor, even more preferably prostate epithelial cells expressing endogenous androgen receptor. The cells employed may be those derived from the prostate. Such cells include, but are not limited to, the LNCaP cell line (available from the American Type Culture Collection under ATCC CRL 1740). Alternatively, the cells need not be derived from the prostate as long as the hKLK2-TRE function is sufficiently maintained.

After selecting clones which demonstrate sufficient levels of reporter gene activity when induced with androgen, the induction ratio may be further enhanced by performing limiting dilution with the cells and screening the resulting clones. In this manner, the induction may be at least 20 fold when induced with an inducing agent such as 0.1–1.0 nM R1881, preferably at least about 50 fold, and more preferably at least about 100 fold. Usually, the induction will not exceed about 500 fold.

An inducing agent can be any compound which is added to the growth environment of the cell and which, upon contact with and/or entry into the cell, results in the transcriptional activation of an hKLK2-TRE. For the purposes of the present invention, an "appropriate inducing agent" is one which specifically induces the expression of an hKLK2-TRE which is operably linked to a reporter gene. For example, an hKLK2 enhancer is inducible with androgen. An example of an inducing agent used is R1881.

When the inducing agent is an androgen, cells are desirably grown in hormone-free medium, e.g. RPMI medium supplemented with 10% fetal bovine serum, 100 units/ml penicillin and 100 μg/ml streptomycin, and assayed in hormone spiked medium, e.g. 10% strip-serum RPMI with hormone. Desirably, the cells should not have been passaged more than about 50 times, more desirably not more than about 25 times.

Once an hKLK2-TRE-reporter gene construct has been introduced into the host cell and stable cell lines are made, the cells may be cultured in a suitable growth medium, then exposed, along with an inducing agent, to an agent whose ability to modulate the activity of the hKLK2-TRE is to be tested.

Stable cell lines comprising an expression construct which comprises an hKLK2-TRE driving expression of a reporter gene can be generated for use in the screening methods, as described above. Alternatively, appropriate cells can be transiently transfected with the expression constructs, the cells cultured in a suitable growth medium, then exposed, along with an inducing agent, to an agent whose ability to modulate the activity of the hKLK2-TRE is to be tested. Methods for transient transfection are known in the art.

The reporter gene used can encode luciferase activity, and an assay system can be chosen such that the product of the luciferase activity is luminescent. Luminescence may be determined in accordance with conventional commercial kits, e.g. enhanced luciferase assay kit (Analytical Luminescence Laboratory, MI). The cells may be distributed in multiwell plates which can be accommodated by a luminometer. A known number of cells is introduced into each one of the wells in an appropriate medium, the candidate compound added, and the culture maintained for at least 12 hours, more usually at least about 24, and not more than about 60 hours, particularly about 48 hours. The culture is then lysed in an appropriate buffer, using a non-ionic detergent, e.g. 1% triton X-100. The cells are then promptly assayed. In conjunction with the candidate compound, an inducing compound, e.g. androgens, will also be added such as methyl trienolene (R1881), or dihydrotestosterone (DHT). The concentration of these inducing agents will vary depending upon the nature of the agent, but will be sufficient to induce expression. The concentration with R1881 will generally be in the range of about 0.1–10 nM, preferably about 1 nM.

In this embodiment, an androgen or other inducing agent is added to the culture medium at about the same time as the compound to be tested and, after a suitable time, cells are tested for amount of reporter gene product. A "suitable time" in this assay means an amount of time sufficient for the agent to be tested to effect a change in the levels of reporter gene product such that a difference from the control can be measured. This amount of time may depend on the stability of the reporter gene messenger RNA or protein, on how readily the agent enters the cell, on how stable the agent is once it enters the cell, and/or on other factors. In general, a suitable time must be determined empirically and this is well within the skill of one of ordinary skill in the art. A decrease or increase in the level of reporter gene product of from at least about 25% to about 40%, more preferably from at least about 40% to about 70%, and most preferably from about 70% to about 100% is indicative of an agent that modulates the activity of an hKLK2-TRE.

Assay methods generally require comparison to a control sample to which no agent is added. Modulation of hKLK2 expression is said to be effected by a test agent if such an effect does not occur in the absence of the test agent.

In another embodiment, the above-described hKLK2-TRE-reporter gene plasmid constructs may also be introduced into the host cells for transient expression of the reporter gene. In this assay system, the compound to be tested and an androgen may be added before or simultaneously with introduction of the plasmid into the cells. To correct for differences in transfection efficiency, the cells can be co-transfected with a reference plasmid encoding, for example, β-galactosidase. The cells are then cultured for a time, after which the level of reporter gene product is measured and, if appropriate, the product encoded by the plasmid serving as a transfection efficiency control is also measured. The ability of the agent to modulate the activity of an hKLK2-TRE is measured as a difference in the amount of reporter gene product relative to control cell culture to which no test compound was added.

In a further embodiment of the present invention, an hKLK2-TRE operably linked to a reporter gene may be incorporated into a viral vector for packaging into a viral particle. The virus may be any known in the art which can infect eukaryotic cells. Preferably, adenovirus is used. An hKLK2-TRE-reporter gene may be incorporated into an adenoviral vector at a variety of sites. Preferably one or more genes essential for adenovirus replication are replaced with an hKLK2-TRE-reporter gene construct. For example, the regions known as E1A and E1B can be replaced with a fragment of DNA containing an hKLK2-TRE operably linked to a reporter gene. The resulting adenovirus construct can be propagated by passage through a cell line that provides the E1A and E1B gene products, e.g. 293 cells, by methods known in the art. In this assay system, the adenovirus construct containing an hKLK2-TRE operably linked to a reporter gene can be used to infect an appropriate cell line such as those described above. An agent whose ability to modulate the activity of an hKLK2-TRE can be added either simultaneously with the adenoviral construct or after a suitable time. A "suitable time" in this assay system means an amount of time sufficient to allow entry of the viral particle into the cell, subsequent uncoating of the viral particle, and transport into the nucleus. This amount of time may be from about one to about five hours. After culturing the cells in an appropriate growth medium, the levels of reporter gene product are measured and compared to levels in recombinant host cell cultures to which no agent has been added.

Compounds can be tested singly or in combination with one another. Thus, screening assays provide a method for identifying an "agent," which can be used to modulate hKLK2 expression in a cell in vitro or in a patient. An "effective agent" is one that modulates hKLK2 expression.

As used herein, the term "modulate" means that the effective agent can increase or decrease the level of expression of a gene under transcriptional control of an hKLK2-TRE or an active fragment thereof. Modulation can occur as a result of an effect at any point in signal transduction from the membrane of the cell to the nucleus. The ways that an effective agent can act to modulate the expression of hKLK2 include, but are not limited to 1) modifying binding of a transcription factor to an hKLK2-TRE; 2) modifying the interaction between two transcription factors necessary for hKLK2 expression; 3) altering the ability of a transcription factor necessary for hKLK2 expression to enter the nucleus; 4) inhibiting the activation of a transcription factor involved in hKLK2 gene transcription; 5) modifying a cell-surface receptor which normally interacts with a ligand and whose binding of the ligand results in hKLK2 expression; 6) inhibiting the inactivation of a component of the signal transduction cascade that leads to hKLK2 expression; and 7) enhancing the activation of a transcription factor involved in hKLK2 gene transcription.

The following examples are provided to illustrate but not limit the invention.

EXAMPLES

Example 1

Cloning and Sequencing of the hKLK2 5'-Flanking Region

The results produced from chromosome walking in chromosome 19 indicated that hKLK2 is located approximately 12 kbps downstream from PSA gene in a head-to-tail fashion. Riegman et al. (1992) *Genomics* 14:6–11. Based on this indication, a 12 kbp DNA fragment lying upstream from the first exon in hKLK2 was amplified by PCR using human genomic DNA as template and the synthetic oligonucleotides:

42.100.1: 5'-GAT CAC CGG TGT CCA CGG CCA GGT GGT GC-3' (SEQ ID NO:6) PinAI site underlined, which is complementary to the 5'-untranslated region (UTR) of the first exon in hKLK2 and 42.100.4: 5'-GAT CAC CGG TAT ACC AAG GCA CTT GGG CCG AAT G-3' (SEQ ID NO:7), PinAI site underlined, which corresponds to the 3'-UTR of PSA mRNA.

The oligonucleotides created a PinAI site at both ends of the PCR fragment. The PCR fragment was purified and ligated into pGEM-T vector (Promega) to generate plasmid CN312. This plasmid provides the hKLK2 transcription response elements (TREs) for the constructs reported here.

Figure 1:
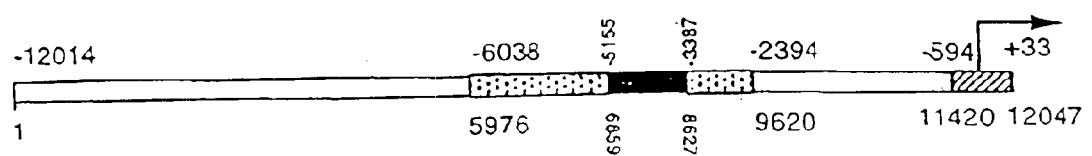
FIG. 1 is a schematic representation of the hKLK2 promoter/enhancer region depicted in SEQ ID NO:1. The numbers above the bars correspond to the position relative to the hKLK2 transcription start site; the numbers below the bars correspond to SEQ ID NO:1. The portion depicted by diagonal lines represents the promoter region (Schedlich et al. (1987)); the dotted portion (including the solid portion) represents an active enhancer region; the solid portion represents a smaller enhancer region; and the transcription initiation site is indicated by a bent arrow.

The sequence of this fragment was determined by fluorescent dye terminator labeling method using Ampli Taq DNA polymerase. The sequence extends for 12047 bp between EcoRI and PinAI sites and is shown schematically in FIG. 1. Part of the promoter region was previously published. Schedlich et al. (1987). The previously published sequence extends from 9766 to 12047. Upon inspection, notable features of the sequence are the homonucleotide stretches found in several locations. The largest is a polypyrimidine tract of 135 bases between 3867 (−8144, relative to the transcription site of hKLK2 gene) and 4002 (−8012). In addition, poly(T) regions are found near 10768 (−1246) (16 bases) and 10753 (−1261) (23 bases).

There is a high degree of nucleotide sequence identity (about 66%) between the hKLK2 5'-flanking region from 6019 (−5995, with respect to the cap site) to 12019 (+5) and that of the prostate specific antigen enhancer (PSE). U.S. Pat. No. 5,648,478. Computer analysis of the sequence found approximately 75% homology between PSE and hKLK2 in the far upstream region from nt −4739 to −2513 in addition to the highly homologous promoter regions (81%). Schuur et al. (1996); Schedlich et al. (1987). More interestingly, the hKLK2 sequence between nt −3819 to −3805 on the minus strand matches the consensus ARE at 14 of 15 positions, and is identical to the AREIII found in PSE. Pang et al. (1997) *Cancer Res.* 57:495–499.

Example 2
Construction of Reporter Constructs in which Expression of Reporter Genes is Under the Control of the hKLK2 5'-Flanking Region To identify the function of the DNA segment containing the putative enhancer, a series of constructs was generated by inserting the hKLK2 5'-flanking region upstream of the luciferase reporter gene, and the activity of these fragments was compared with that of CN299, a plasmid with the full hKLK2 promoter (−607 to +33) driving the expression of firefly luciferase. The constructs are as follows:

To clone the hKLK2 full promoter an approximately 600 bp fragment was amplified with the oligonucleotides 41.100.1 and 42.100.2 (5'-GAT CAC CGG TGC TCA CGC CTG TAA TCT CAT CAC-3' (SEQ ID NO:8), PinAI site underlined). 42.100.2 corresponds to the upstream region of the hK2 promoter. The PCR product was then cloned into pGEM-T vector (Promega) to generate CN294.

CN299 is a plasmid containing the luciferase coding segment driven by the full hKLK2 promoter. The full promoter region was released from CN294 by NcoI-SacI digestion and ligated into a similarly cut pGL3-Basic (Promega) to generate CN299.

CN322 is a plasmid containing the entire structural gene of firefly luciferase driven by the human hKLK2 promoter and other regulatory elements contained within the 12 kb hKLK2 5'-flanking fragment. The entire 12 kbp hKLK2 5'-flanking region was excised from CN312 by SacII/SpeI digestion and ligated into SacII/SpeI digested pGL3-Basic to produce CN322.

CN324 is a luciferase construct containing the hKLK2 minimal promoter driving the luciferase coding region. The minimal hKLK2 promoter was released from CN317 by NcoI-SacI digestion and ligated into a similarly cut pGL3-Basic to generate CN324.

CN325 is the same as CN324, except that a XhoI site (instead of a PinAI site) was created at the 5' end of the minimal promoter.

CN355 was created by digesting CN340 with XhoI and KpnI. The released fragment (~3.8 kbps) was ligated into CN325, upstream of the minimal promoter.

CN296 is a pGEM-T vector derivative containing an hKLK2 fragment from nt −2247 to +33, which was amplified by PCR with oligonucleotides 42.100.1 and 42.100.3 (5'-GAT CAC CGG TGG TTT GGG ATG GCA TGG CTT TGG-3'; SEQ ID NO:9), PinAI site underlined). 42.100.3 corresponds to a region approximately 2300 bp upstream of hKLK2.

CN317 is a pGEM-T derivative containing the hKLK2 minimal promoter. A PCR fragment corresponding to the hKLK2 5'-UTR from nt −323 to +33 was amplified with two synthetic oligonucleotides; 42.100.1 and 43.121.1 (5'-GAT CAC CGG TAA AGA ATC AGT GAT CAT CCC AAC-3'; SEQ ID NO:10, PinAI site underlined). The resulting PCR product was cloned into pGEM-T vector.

CN390 was constructed as follows. A fragment with KpnI and XhoI sites at the ends was amplified from CN379 with synthetic oligonucleotides 51.96.3 (5'-GAT CGG TAC CAA AAG CTT AGA GAT GAC CTC CC-3'; SEQ ID NO:11) and 51.96.4 (5'-GAT CCT CGA GGC AAT AAT ACC GTT TTC TTT TCT GG-3'; SEQ ID NO:12). The resulting fragment was digested with XhoI and KpnI, then cloned into similarly cut CN325, to generate CN390.

CN396 was generated using the procedure used to generate CN390, except that a different set of oligonucleotides was used for amplification. The oligonucleotides for amplifying the hKLK2 enhancer fragment were 51.96.1 (5'-GATCGGTACCGGGATGATCAGAGCAGTTCAGG-3'; SEQ ID NO:13) and 51.96.4. The amplified fragment was digested with with XhoI and KpnI, then cloned into similarly cut CN325, to generate CN396.

CN408 was constructed as follows. CN379 was digested with KpnI and XhoI, the enhancer-containing fragment was isolated and ligated to similarly cut pGL3. pGL3 contains an SV40 promoter. CN408 thus comprises an hKLK2 enhancer operably linked to an SV40 promoter.

CN300 was constructed by inserting the hKLK2 fragment from −2247 to +33 released from CN296 by NcoI-SacI digestion and ligated into a similarly cut pGL3-Basic in wild type orientation.

CN339 was created by digesting CN322 with SacI, gel purifying the larger fragment and ligating the larger fragment to the vector. The final construct is a plasmid that contains the luciferase gene driven by a 5.2 kb hKLK2 5'-flanking sequence.

CN340 contains a 6.0 kb fragment that was amplified from CN312 with the oligonucleotides 42.156.3 (5' GCC AGG TGT GGT GGC AAG CACC 3'; SEQ ID NO:28) and 43.163.1 (5' GAT CGG TAC CAC TCA CTA TAG GGC GAA TTG GGC 3'; SEQ ID NO:29). This PCR product was amplified from the 5'-flanking region of the hKLK2 gene and was ligated into pGEM-T, creating CN340.

CN354 has a 1.0 kb extension of the 5'-UTR in CN339. A SacI-KpnI fragment was released from CN340 by enzyme digestion and ligated into a similarly cut CN339 to produce CN354.

CN377 is a luciferase reporter construct containing a hKLK2 5' flanking region which was amplified by PCR with CN312 as template and two synthetic oligonucleotides: 51.70.1(5' GGA AAT CAA ACA CAA CCA CAT CCC 3'; SEQ ID NO:30) and 51.70.2(5' GAT CGG TAC CTC ACT AAA GGA TCA GGG ACC 3'; SEQ ID NO:31). The PCR product was digested with KpnI and XhoI, ligated into a similarly cut CN325, creating CN377.

CN378, CN380, CN381 were made in a manner similar to that for CN377. The following primer pairs were used. CN378: 51.70.1 and 51.70.3 (5' GGA TGG TAC CAG TTG CAT GGG GCA AAG ACA AGG 3'; SEQ ID NO:32); CN380: 51.70.2 and 51.70.6(5' GAT CCT CGA GTT CCT CCA GAG TAG GTC TGC 3'; SEQ ID NO:33); and CN381: 51.70.1 and 51.70.5 (5' GAT CGG TAC CAT GAT TAG ACA TTG TCT GCA GAG 3'; SEQ ID NO:34).

Example 3
Generation of Transiently and Stably Transfected Cell Lines with hKLK2 Enhancer Constructs Cells and Culture Methods.

LNCaP cells were obtained at passage 9 from the American Type Culture Collection (Rockville, Md.). LNCaP cells were maintained in RPMI 1640 medium (RPMI) supplemented with 10% fetal bovine serum (FBS; Intergen Corp.), 100 units/mL of penicillin, and 100 units/mL streptomycin. LNCaP cells being assayed for luciferase expression were maintained in 10% strip-serum (charcoal/dextran treated fetal bovine serum to remove T3, T4, and steroids; Gemini Bioproduct, Inc., Calabasas, Calif.) RPMI. The cells were periodically tested for the production of PSA which was consistently above 20 ng/mL per day.

Selection for a stably integrated plasmid DNA is performed in RPMI medium containing G418 (GibcoBRL, NY). The level of G418 in RPMI is decreased from 500 to 100 µg/mL after selection of the parental LNCaP clones for evaluation; these clones are maintained in 100 µg/mL G418 at all times prior assaying. Subclones having enhanced luciferase activity are obtained from the parental cell line by the method of limited dilution cloning.

Transfections of LNCaP Cells.

For transfections, LNCaP cells were plated out at a cell density of $5\times10^5$ cells per 6-cm culture dish (Falcon, N.J.) in complete RPMI. DNAs were introduced into LNCaP cells after being complexed with a 1:1 molar lipid mixture of N-[1-(2,3-dioleyloxy)propyl-N,N,N-trimethylammonium chloride (DOTAP™; Avanti Polar Lipids, AL) and dioleoyl-phosphatidylethanolamine (DOPE™; Avanti Polar Lipids, AL); DNA/lipid complexes were prepared in serum-free RPMI at a 2:1 molar ratio. Typically, 8 µg (24.2 nmole) of DNA was diluted into 200 µL of incomplete RPMI and added dropwise to 50 nmole of transfecting, lipids in 200 µL of RPMI with gentle vortexing to insure homogenous mixing of components. The DNA/lipid complexes were allowed to anneal at room temperature for 15 minutes prior to their addition to LNCaP cells. Medium was removed from LNCaP cells and replaced with 1 mL of serum-free RPMI followed by the dropwise addition of DNA/lipid complexes. Cells were incubated with complexes for 4–5 hours at 37° C., 5% $CO_2$. Medium was removed and cells washed once with PBS. The cells were then trypsinized and resuspended in 10% strip-serum RPMI (phenol red free). Cells were replated into an opaque 96-well tissue culture plate (Falcon, N.J.) at a cell density of 40,000 cells/well per 100 µL media and assayed. Varying amounts of drugs (e.g. androgens and anti-androgens) were added 16 hours later and assayed for luciferase activity 32 hours thereafter.

Generation of a stably transfected cell line expressing luciferase is accomplished by co-transfecting the plasmid pcDNA3 with hKLK2-TRE-Luc. The neomycin gene of pcDNA3 confers resistance to the antibiotic G418, allowing selection of stably transfected LNCaP cells. LNCaP cells are co-transfected with hKLK2-TRE-Luc and pcDNA3 as described for transient transfections. Briefly, 1 µg of pcDNA3 and 1–10 µg of hKLK2-TRE-Luc are diluted into 200 µL of RPMI and complexed with two molar equivalents of DOTAP/DOPE (1:1) in 200 µL RPMI. Addition of DNA to lipids is dropwise with gentle vortexing to homogeneously mix the samples. After annealing the complexes for 15 minutes, they are added dropwise to LNCaP cells in 1 mL RPMI and incubated overnight (12 hours) at 37° C. Media/DNA-lipid complexes are removed from the tissue culture plates and supplemented with complete RPMI containing 500 µg/mL G418. The selection media is kept at 500/µg/mL G418 for three weeks before being lowered to 250 µg/mL. G418 resistant colonies generally appear after four weeks and are allowed to grow until visible by eye, upon which colonies are trypsinized (0.25% trypsin) and transferred to a 24 well tissue culture plate, followed by further expansion. Clones are assayed for luciferase expression after they reach about $3–5\times10^6$ cells.

Induction and Assaying of Transient and Stable hKLK2-TRE-Luc/LNCaP Cells.

For both transient and stably transfected LNCaP cells, a variety of androgens and anti-androgens—methyl trienolone (R1881, DuPont NEN), dihydrotestosterone (DHT, Sigma), cyproterone acetate (CA) and hydroxyflutamide (Ho-Flu)—are used to induce expression of the luciferase reporter gene. Androgens or anti-androgens are prepared at 3× concentrations in 10% strip-serum RPMI and added as 50 µL aliquots to each well of the 96-well plate. Cells are incubated with either androgens or anti-androgens for 48 hours before assaying. Assays are done in triplicate or quadruplicate. The concentration of dihydrotestosterone (DHT) is measured by the Testosterone ELISA Kit (Neogen Corporation). The assay has 100% cross reactivity with DHT.

In the case of stably transfected hKLK2-TRE-Luc/LNCaP clones, medium is removed and cells washed with PBS (2×20 mL). The clonal cells are then maintained in 10% strip-serum RPMI (phenol red free) for 24 hours prior to trypsinizing and replating into an opaque 96-well plate at 40,000 cells/well per 100 µL media. Cells are allowed to become adherent overnight before the addition of either androgens or anti-androgens. Incubation of clonal cells in strip-serum RPMI prior to induction with drug(s) substantially lowers background luciferase expression.

The luciferase assay of both transient and stably transfected cells is performed in the same manner. After induction of cells with androgens or anti-androgens for 48 hours, medium is removed and 50 µL of lysis reagent added (0.1 M potassium phosphate buffer at pH 7.8, 1% triton X-100, 1 mM dithiothreitol, 2 mM EDTA) to each well. Cells are assayed within 15 minutes of lysis or stored at −80° C. until analysis. Storage of cell lysates at −80° C. for five days or less does not result in significant loss of luciferase activity.

The Enhanced Luciferase Assay Kit (Analytical Luminescence Laboratory, MI) was used to quantitate the extent of luciferase activity from hKLK2-Luc transfected LNCaP cells. A Dynatech 3000 96-well plate luminometer (Dynatech, VA) was used to measure the amount of light generated from the assay. The instrument was run in the Enhanced Flash Mode, employing a dual injector system for substrate addition. Optimal assay conditions and Luminometer parameters were as follows: addition of 60 µL of Substrate A (buffer), 1 second delay, addition of 60 µL of Substrate B (luciferin reagent), 1 second delay, integrate signal for 3 seconds. The results are depicted as the integral sum in relative light units (RLUs). The extent of induction by androgens/anti-androgens, e.g. fold induction, was determined by:

fold induction=$RLUs$ [$xnM$ drug]/$RLUs$ [0 $nM$ drug].

Example 4
Effects of the hKLK2 5'-Flanking Region

Figure 3:
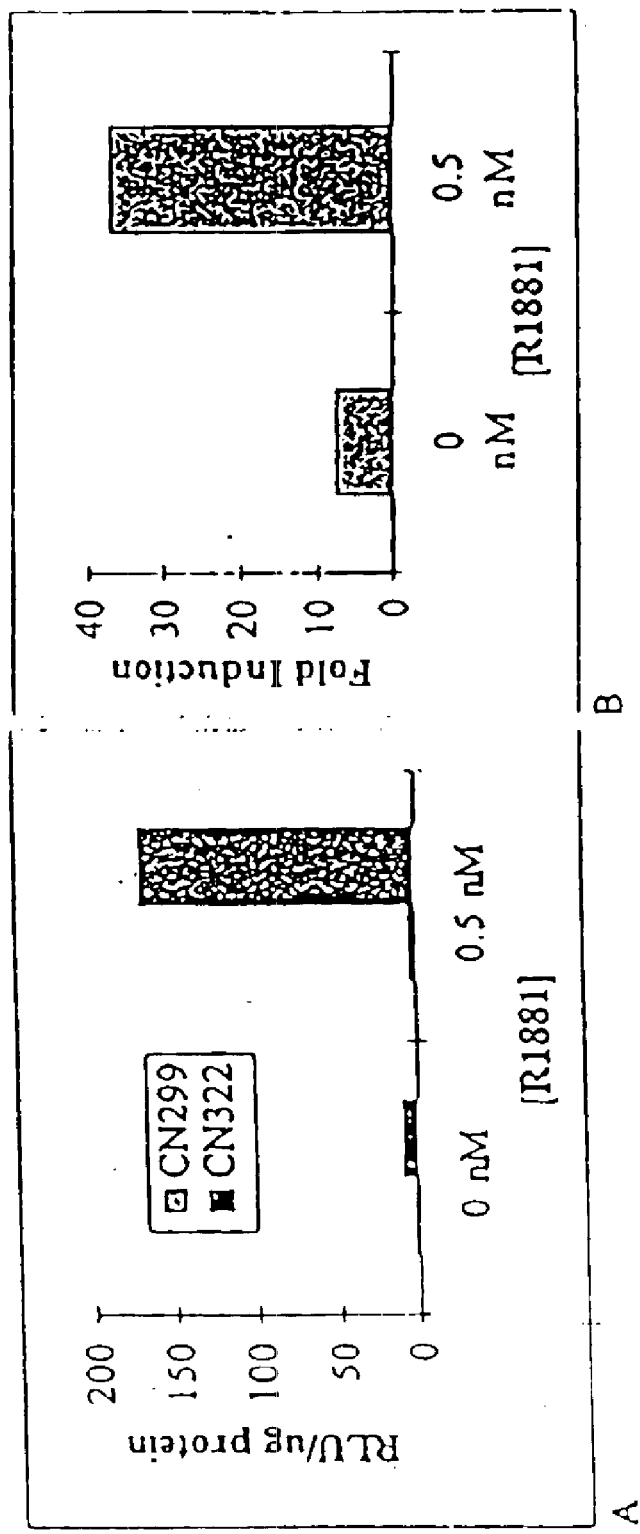
FIGS. 3A and 3B are bar graphs of testosterone analog R1881 induction of hKLK2 promoter/enhancer-driven luciferase expression in LNCaP (human metastatic prostate adenocarcinoma) cells. LNCaP cells were transfected with reporter gene constructs, incubated in the presence or absence of inducer, and, 48 hours after transfection, luciferase activity was measured.

To determine the effect of the 12 kbp 5'-flanking sequence on promoter activity, two constructs were created: CN299 and CN322, as described in Example 2. The hKLK2 promoter was cloned upstream of the luc gene to create CN299. The entire 12 kbp sequence upstream of the hKLK2 gene (including the promoter) was cloned upstream of the luc gene to create CN322. Each construct was then used to transfect LNCaP cells. The media in half of the dishes was supplemented with 0.5 nM R1881. The cells were harvested 48 hours post transfection and the luciferase activity was measured. FIGS. 3A and 3B summarize the data and demonstrate that CN322 has higher activity than CN299. At both R1881 concentrations tested, CN322 had higher activity than CN299. At 0 nM, CN322 was 12 fold more active than CN299. At 0.5 nM, CN322 was approximately 36 fold more active than CN299. These data suggest that the 12 kb 5'-flanking sequence contains an enhancer and that this enhancer is also androgen responsive.

Example 5
Characterization of the hKLK2 Enhancer

Figure 4:
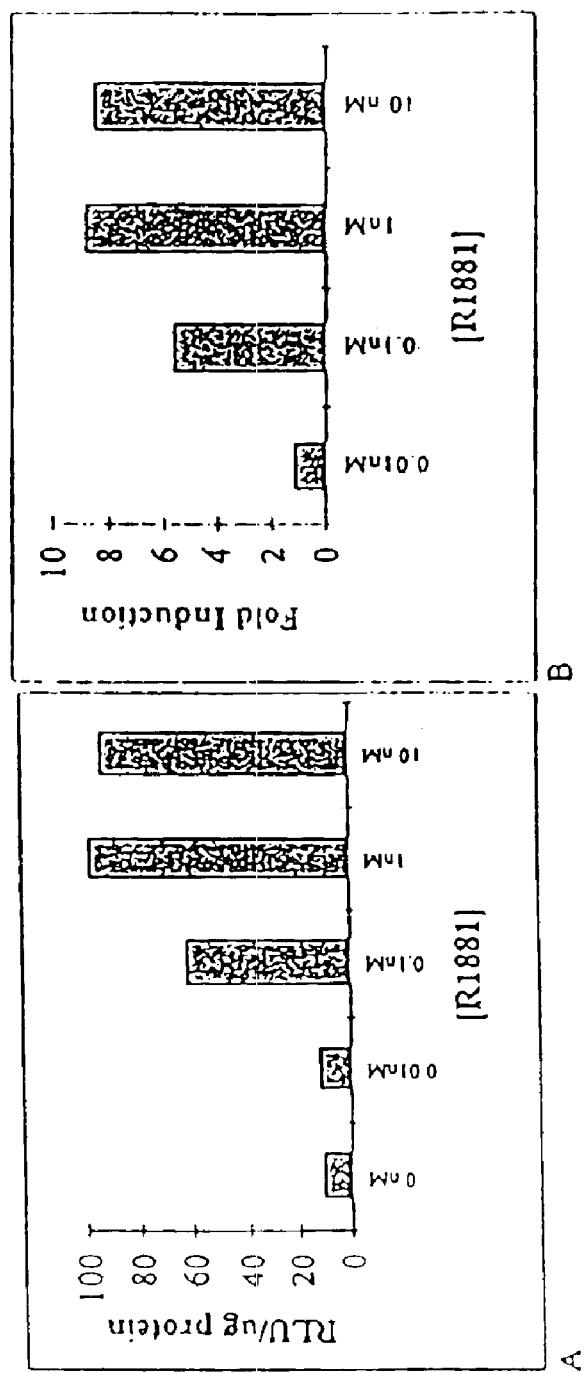
FIGS. 4A and 4B are bar graphs of the concentration dependence of R1881-mediated induction of hKLK2 promoter/enhancer-driven luciferase expression. LNCaP cells were transfected with CN322 and cells were incubated in various concentrations of R1881. Cells were harvested 48 hours after transfection and luciferase activity was measured.

The results of the previous experiment suggested that the luciferase activity of the putative enhancer found in CN322 responded in an androgen-dependent manner. To determine if the hKLK2 5'-flanking sequence did indeed contain an androgen responsive element, two experiments were conducted. In the first experiment, LNCaP cells were transfected with CN322, the transformants were incubated in medium containing various concentrations of R1881, and 48 hours after transfection, luciferase activity was measured. The results are summarized in FIGS. 4A and 4B. In short, CN322 responded to the testosterone analog R1881 in a concentration dependent manner. Peak induction of activity was estimated at 1 nM R1881, about 9 fold over the 0 nM activity.

Figure 5:
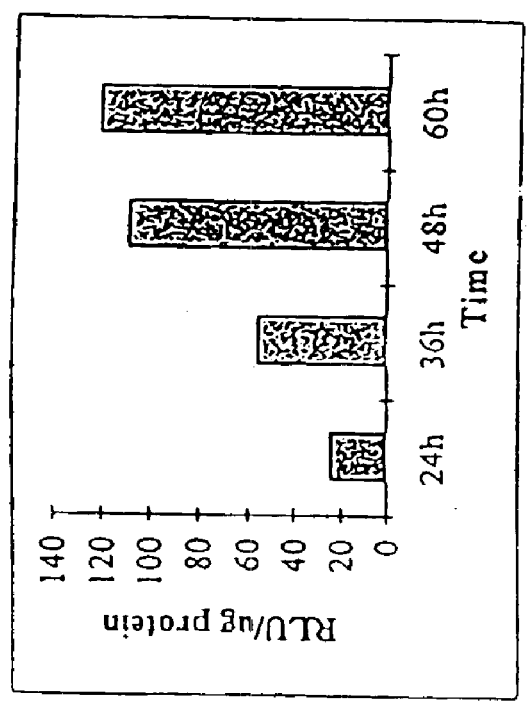
FIG. 5 is a bar graph showing induction of luciferase activity as a function of time of incubation with R1881. LNCaP cells were transfected with CN322 and cells were incubated in medium containing 0.5 nM R1881 for various periods of time, after which luciferase activity was measured.

In the second experiment, the effect of time of incubation in the presence of R1881 on the activity of the 12 kbps 5'-flanking sequence was assessed. LNCaP cells were transfected with CN322 and incubated for various periods of time in the presence of 0.5 nM R1881 before harvesting. The results are summarized in FIG. 5. The peak luciferase activity was seen at 60 hours post transfection, but the overall upward trend seemed to plateau at about 48 hours post transfection.

To summarize these two experiments, it seemed that the hKLK2 enhancer appears to be androgen responsive and peak induction of luc activity takes place somewhere between 48 and 60 hours post transfection.

Example 6
Tissue Specificity of the hKLK2 5' Flanking Region

Figure 6:
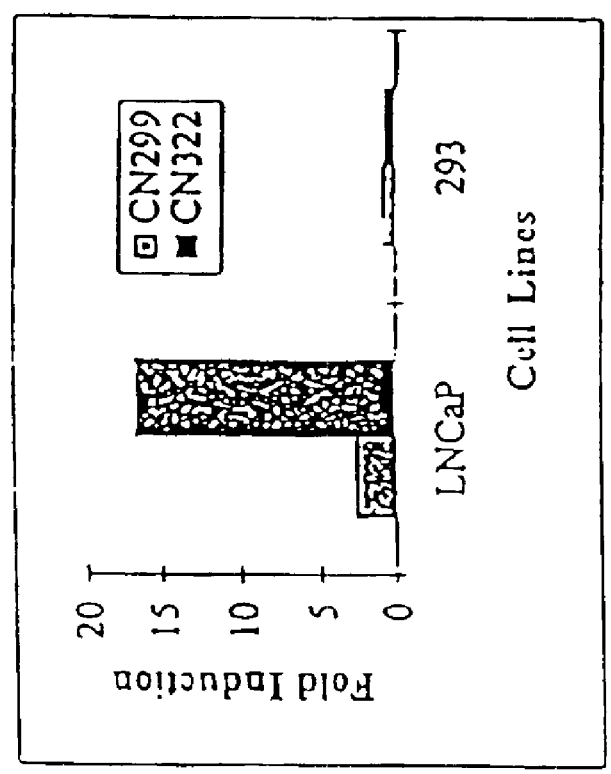
FIG. 6 is a bar graph depicting the cell type specificity of hKLK2 promoter/enhancer-driven luciferase expression. LNCaP or 293 (human embryonal kidney) cells were transfected with CN299 or with CN322 plasmid constructs and incubated in the absence or the presence of 1 nM R1881. Cells were harvested 48 hours post transfection and luciferase activity was measured. Fold induction was calculated by comparing RLU/μg protein with and without 1 nM R1881.

Knowing that the PSA enhancer is tissue specific, a series of experiments was conducted to determine if the same was true for the putative hKLK2 enhancer. In the first experiment, LNCaP cells (a prostate cancer cell line) and 293s (a human embryonic kidney cell line) were transfected with CN299 or CN322. Half of the dishes were supplemented with 1 nM R1881, and the cells were harvested 48 hours post transfection. The LNCaP cells transfected with CN322 exhibited a 17 fold induction of activity in the presence of 1 nM R1881 when compared to the background activity at 0 nM R1881. The 293 cells transfected with CN322 showed no induction of luciferase activity in the presence of 1 nM R1881. CN299 exhibited a 2–3 fold induction in the presence of 1 nM R1881, and no induction of activity in the 293 cells. The results of this first experiment are summarized in FIG. 6. The results of this experiment again support the conclusion that the putative hKLK2 enhancer is androgen inducible.

Figure 7:
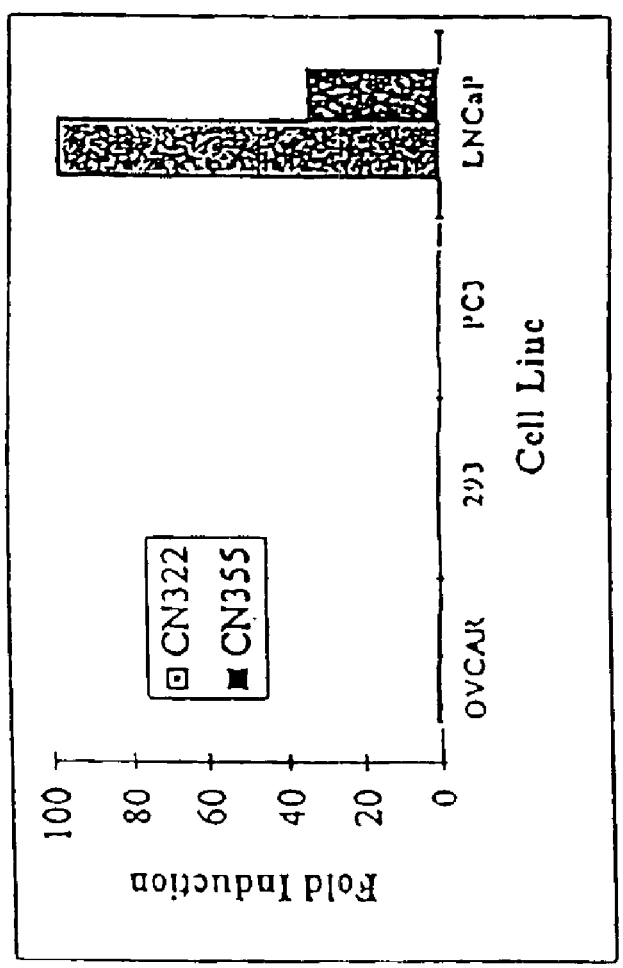
FIG. 7 is a bar graph depicting the activity of the hKLK2 enhancer/promoter in various cell lines. Various cell lines were transfected with either CN322 or CN355, and, after an overnight incubation in complete medium, were incubated in the presence or absence of R1881. CN355 contains a 3.8 kb fragment from approximately −6200 to approximately −2400 of the hKLK2 enhancer fused to the minimal hKLK2 promoter to control luciferase expression. The cell lines used were: OVCAR, human ovarian adenocarcinoma; 293, transformed human primary embryonal kidney; PC3, human grade IV prostate adenocarcinoma; LNCaP, metastatic human prostate adenocarcinoma.

Results of earlier experiments indicated that a putative hKLK2 enhancer may lie between the ApaI site at approximately –6200 bp and the XhoI site at approximately –2400 bp of the hKLK2 enhancer. This 3.8 kbp fragment was fused upstream of the minimal hKLK2 promoter and then cloned upstream of the luc gene, creating CN355. A variety of cell lines were transfected with CN322 or CN355 by incubating them with the complexes in complete media overnight. The complexes were then aspirated and the media was replaced with stripped serum media. The media in half of the plates was supplemented with 1 nM R1881. The cells were then harvested 48 hours after the removal of the DNA-lipid complexes and tested for luciferase activity. The results are summarized in FIG. 7.

CN322 gave almost a 100 fold induction of activity in the presence of 1 nM R1881 in the LNCaP cells. CN355 exhibited a 35-fold induction of activity under the same conditions. All of the other cell lines showed little androgen inducibility. In fact, CN322 and CN355 showed only about a 1–2 fold induction in any of the other cell lines. To further delineate the sequences required for enhancer activity, the construct CN379 was made, which has, in addition to the minimal hKLK2 promoter, the regions from –5155 to –3387 (referred to in U.S. Ser. No. 60/054,523 as –5155 to –3412) driving expression of the luciferase gene. This construct gave approximately 54-fold induction of luciferase activity in the presence of inducing agent. When these experiments were repeated, CN322 gave an approximately 30-fold induction. This result may be due to the presence of a negative regulator in the sequences between nucleotides 5976 to 6859 and/or 8627 to 9620. These data show that the minimal enhancer constructs CN355 and CN379 retained some of the activity of the full 12 kbps 5'-flanking sequence, indicating that part of the putative hKLK2 enhancer is between the ApaI and XhoI sites previously described above. The data also support the conclusion that the hKLK2 enhancer is androgen responsive and that its activity is restricted to prostate cell lines expressing androgen receptor.

Example 7
Further Characterization of the hKLK2 Enhancer

Figure 24A:
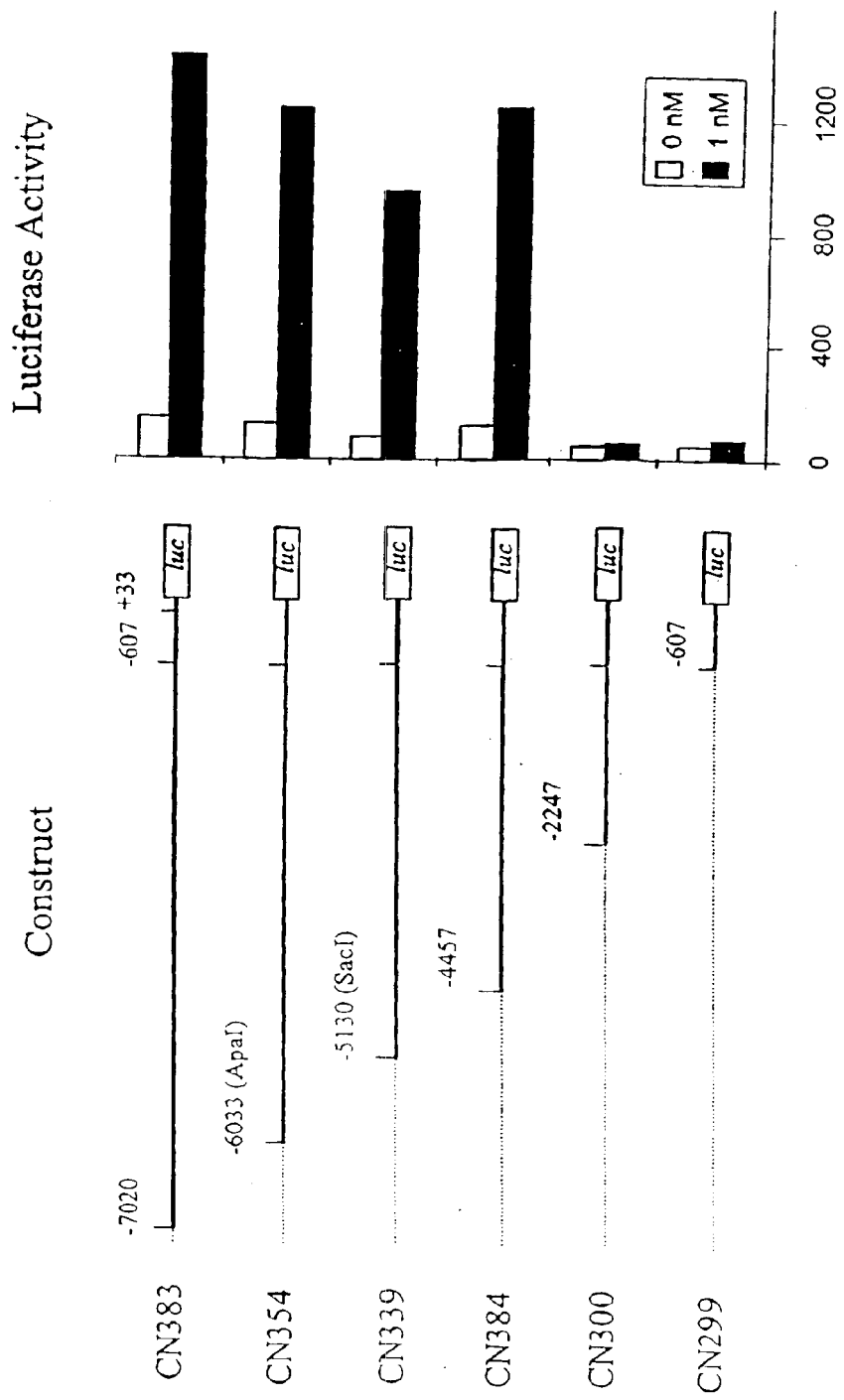
FIGS. 24A and 24B are bar graphs (right) depicting the results of transient transfections using constructs shown schematically (left). A. Exploring the 5' border of the hKLK2 regulatory element. B. Exploring the 3' border of the hKLK2 regulatory element. Luciferase activity data were normalized to µg protein. Solid bars represent luciferase activity in the presence of R1881 (1 nM); open bar represent luciferase activity in the absence of R1881 (0 nM). The thick lines in the schematic representations of the constructs represent the hKLK2 upstream regions that were retained in the reporter constructs. Positions are given relative to the transcription start site.
Figure 24B:
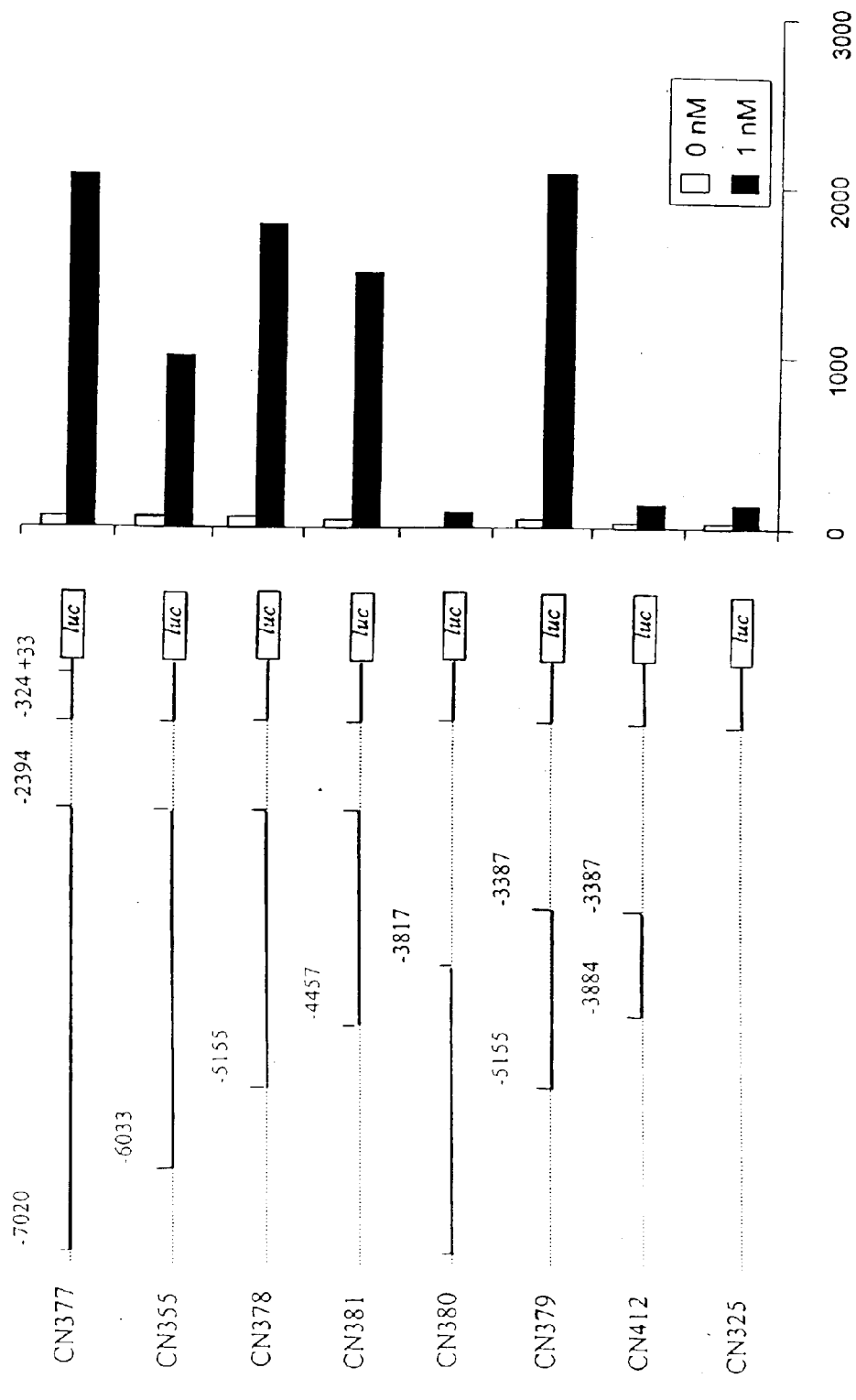

To explore the 5' and 3' borders of the hKLK2 enhancer, a series of constructs were made and tested as described in Example 2. The results, as well as schematic representations of the constructs, are shown in FIGS. 24A and 24B. A 5' extension of 1.6 kb (CN300) resulted in lower overall luciferase activity and no androgen responsiveness (FIG. 24A). A further 5' extension to –5130 (CN339) showed an increase in activity, but further 5' extensions to –6033 and –7020 (CN354 and CN383, respectively) did not result in any additional increases in activity (FIG. 24A). The 3' border of the hKLK2 enhancer was investigated by constructing reporter plasmids containing deletions of upstream sequences starting at –2394. The constructs and results are shown in FIG. 24B. CN378 shows a 40-fold induction while CN325 shows a 5-fold induction of activity. Further removal of the sequences between –2394 to –3387 (CN379) resulted in a 70-fold induction. When the deletion was extended to include half of the putative ARE sequence (CN380), the level of induction was approximately the same as that seen with CN325. The same is true if the sequence between –3884 to –5155 was deleted (CN412). Taken together, these results suggest that the putative ARE sequence as well as the region upstream of the putative ARE are indispensable for a high level of hKLK2 expression and the 3' border of the upstream enhancer element lies between –3387 and –3817.

To further characterize the sequences required for enhancer activity, several constructs were made and are shown schematically in FIG. 8. Portions of hKLK2 upstream region were juxtaposed to the hKLK2 minimal promoter (–324 to +33 relative to the transcription start site), and the resulting TRE operably linked to a luciferase-encoding gene, as described in Example 2. The hKLK2 enhancer-promoter expression plasmids were transfected into LNCaP cells, the cells were incubated in the presence or absence of the inducing agent R1881, and, 48 hours after transfection, luciferase activity was measured, as described in Example 3. The construct CN325, which contains the minimal hKLK2 promoter operably linked to a gene encoding luciferase was used as a control to assess the relative contributions of enhancer fragments to increases in transcription in contructs containing hKLK2 enhancer fragments operably linked to the hKLK2 minimal promoter. The results are shown in FIG. 8.

CN379 has, in addition to the minimal hKLK2 promoter, the hKLK2 5' flanking region from −5155 to −3387 (nucleotides 6859 to 8627 of SEQ ID NO:1) driving expression of the luciferase gene. The CN379 hKLK2 promoter-enhancer results in an approximately 81-fold induction of luciferase activity in the presence of inducing agent.

CN390 has, operably linked to the minimal hKLK2 promoter, the hKLK2 5' flanking region from −4814 to −3643 (nucleotides 7200 to 8371 of SEQ ID NO:1; also given in SEQ ID NO:14), driving expression of the luciferase gene. The CN390 hKLK2 promoter-enhancer results in approximately 90-fold induction of luciferase activity in the presence of inducing agent. The 1.17-kb hKLK2 enhancer fragment contained on CN390 thus maintains full enhancer activity when compared with CN379.

CN396 comprises the hKLK2 5' flanking region from −3993 to −3643 relative to the transcription start site (8021 to 8371 of SEQ ID NO:1) operably linked to the minimal hKLK2 promoter. The CN396 promoter-enhancer stimulated a 37-fold induction in luciferase activity. The 350-bp enhancer fragment contained on CN396 may be considered to be a "core regulator". A 136-bp fragment from −3886 to −3751 (nucleotides 8128 to 8263 of SEQ ID NO:1), i.e., a subfragment of the hKLK2 enhancer contained on CN396, did not show any enhancer activity in transient transfection assays when operably linked to an hKLK2 promoter to drive expression of a luciferase-encoding gene.

Figure 9:
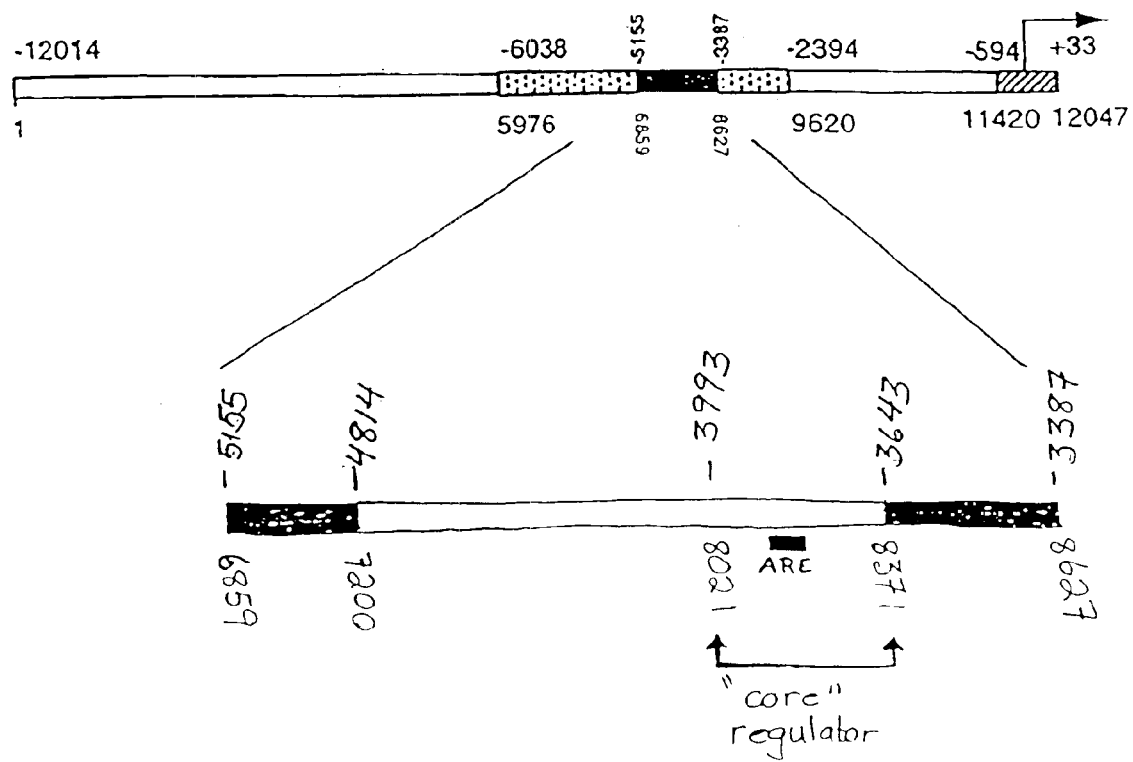
FIG. 9 is a schematic representation of the hKLK2 promoter/enhancer region depicted in SEQ ID NO:1. The numbers above the bars correspond to the position relative to the hKLK2 transcription start site; the numbers below the bars correspond to SEQ ID NO:1. The portion depicted by diagonal lines represents the promoter region (Schedlich et al. (1987)); the dotted portion (including the solid portion) represents an active enhancer region; the solid portion represents a smaller enhancer region; and the transcription initiation site is indicated by a bent arrow. The enhancer region represented by the solid portion is expanded below, and shows a smaller enhancer region (7200 to 8371 of SEQ ID NO:1). Contained within this enhancer region is the 350-bp "core regulator". Also shown is the ARE (nucleotides 8192 to 8206 of SEQ ID NO:1), depicted by a solid bar below the "core regulator".

The above results indicate that the −4814 to −3643 hKLK2 enhancer contained in the CN390 construct retains full function when compared to full-length enhancer (CN322 construct), while the 350-bp core regulator provides a lower level of transcription. These two regions are shown schematically in FIG. 9.

The construct CN408 contains the same hKLK2 enhancer region as does CN379, i.e., from nucleotides −5155 to −3387 (nucleotides 6859 to 8627 of SEQ ID NO:1. However, instead of an hKLK2 minimal promoter, this construct has an SV40 promoter operably linked to this enhancer, driving luciferase gene expression. As shown in FIG. 10A, this construct shows approximately 80-fold induction of luciferase expression. This result suggests that the use of an hKLK2 promoter is not critical to the increase in expression.

The results of the above experiments are summarized in Table 1. The upper level numbers indicate position relative to the hKLK2 start site, while the lower level numbers indicate position in SEQ ID NO:1. Values in the "Induction" column represent approximate fold induction. The upward arrow indicates induction of linked reporter gene expression in LNCaP cells in the presence of inducing agent.

TABLE 1

| Enhancer activity | 5' end | 3' end | Construct | Induction | Promoter |
|---|---|---|---|---|---|
| none | −324 11290 | +33 12047 | CN325 | <10-fold ↑ | minimal hKLK2 |
| none | −607 11407 | +33 12047 | CN299 | <10-fold ↑ | full hKLK2 |
| enhancer activity (9.7 kb) | −12014 1 | −2257 9765 | CN322 | 30- to 90-fold ↑ | full hKLK2 |
| enhancer activity (3.7 kb) | −6038 5976 | −2394 9620 | CN355 | 35-fold ↑ | minimal hKLK2 |
| enhancer activity (1.8 kb) | −5155 6859 | −3387 8627 | CN379 | 81-fold ↑ | minimal hKLK2 |
| enhancer activity (1.17 kb) | −4814 7200 | −3643 8371 | CN390 | 90-fold ↑ | minimal hKLK2 |
| "core regulator" (350 bp) | −3993 8021 | −3643 8371 | CN396 | 37-fold ↑ | minimal hKLK2 |
| enhancer activity (1.8 kb) | −5155 6859 | −338 8627 | CN408 | 80-fold ↑ | SV40 |

Mutations in a Putative ARE Affect Enhancer Function

A putative ARE having the sequence 5' GGAACATAT-TGTATT 3' is located at nucleotides 993 to 1007 of SEQ ID NO:14 (nucleotides 8192 to 8206 of SEQ ID NO:1; −3822 to −3808 relative to the hKLK2 transcription start site). SEQ ID NO:14 gives the sequence of an hKLK2 enhancer contained in the construct CN390 (nucleotides 7200 to 8371 of SEQ ID NO:1). To determine the effect of mutations in this element on hKLK2 enhancer activity, constructs were made which contain alteration in this sequence. CN390 has, operably linked to the minimal hKLK2 promoter, the hKLK2 5' flanking region from −4814 to −3643 (nucleotides 7200 to 8371 of SEQ ID NO:1; given here as SEQ ID NO:14), driving expression of the luciferase gene. This constructs also has the putative ARE. CN457 is as CN390, except that this sequence was changed to 5' GTACTATAT-TACAGT 3' (nucleotides 993 to 1007 of SEQ ID NO:15). Another construct, CN458 is as CN390, except that the putative ARE was changed to 5' GCAGAATATTCGAAT 3' (nucleotides 993 to 1007 of SEQ ID NO:16). hKLK2 enhancer function of these constructs was tested as described above. The results, shown in FIG. 11, demonstrate that alterations in this putative ARE reduce hKLK2 enhancer function to background levels. These results suggest that this element may indeed function as an androgen response element.

The hKLK2 Regulator is an Enhancer

Figure 12:
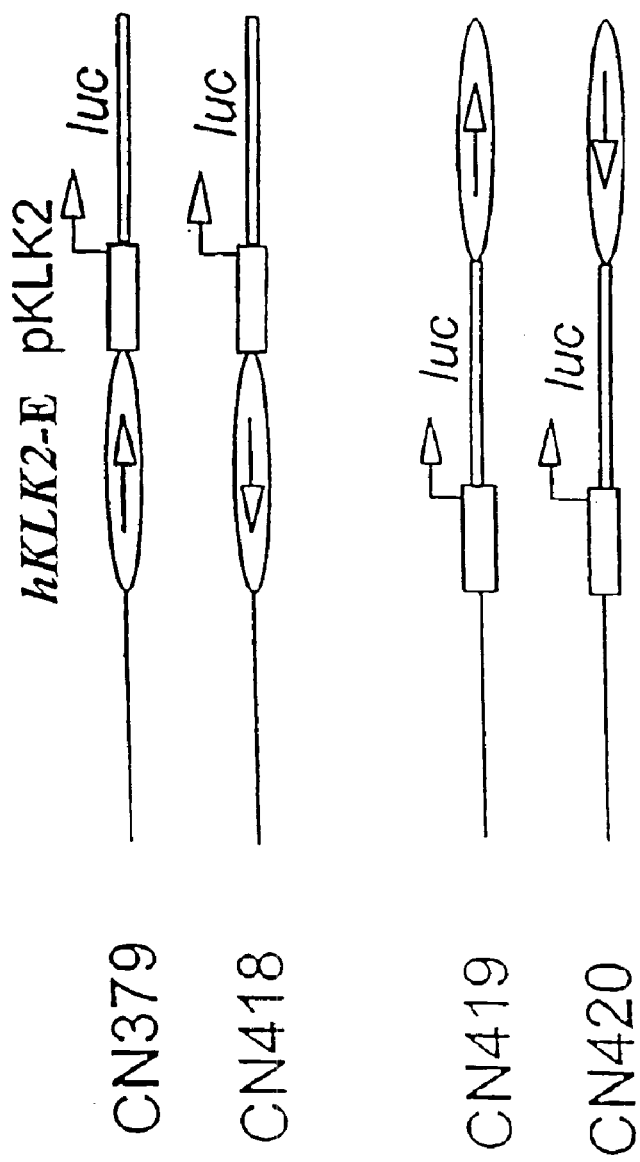
FIG. 12 shows the results of experiments testing the activity of a 1.8-kb hKLK2 enhancer (CN379; nucleotides 6859 to 8627 of SEQ ID NO:1); the 1.8-kb hKLK2 enhancer in opposite orientation as in CN379 and 5' of the luciferase-encoding gene (CN418), the 1.8-kb hKLK2 enhancer in the same orientation as in CN379 but 3' of the luciferase-encoding gene (CN419), and the 1.8-kb hKLK2 enhancer in the opposite orientation as in CN379 and 3' of the luciferase-encoding gene (CN420). Values are given for fold induction in LNCaP cells in the presence of R1881.

One of the defining features of an enhancer element is their ability to stimulate transcription despite their location or orientation relative to the promoter upon which they act. To determine if the regulator of hKLK2 has these properties, constructs were generated by inserting the segment from −5155 to −3387 relative to the hKLK2 transcription start site (nucleotides 6859 to 8627 of SEQ ID NO:1) in various positions and orientations relative to the hKLK2 promoter/luciferase gene transcription unit. As shown in FIG. 12, CN379 yielded an 81-fold induction in LNCaP cells treated with R1881; the same segment in the opposite orientation; CN418, resulted in a 68-fold induction. This level of induction remained unchanged when the upstream element was moved downstream of the luciferase gene with the same orientation as in CN379, as shown with the construct CN419. Reversal of this orientation downstream of the luciferase gene in CN419 also resulted in a high level of induction, as shown with the construct CN420. The hKLK2 enhancer fragment from −5155 to −3387 is a true enhancer, since its activity was not significantly affected by position or orientation relative to the hKLK2 minimal promoter.

Tissue Specificity of the hKLK2 Enhancer

The tissue specificity of the hKLK2 enhancer constructs described above was tested. A variety of cell lines were treasfected with three reporter constructs: CN325 (minimal hKLK2 promoter), CN390 (1.17 kb "full enhancer activity" hKLK2 enhancer/minimal hKLK2 promoter) and CN396 (350-bp minimal hKLK2 enhancer/minimal hKLK2 promoter). The cell lines used represent several hormone-responsive tissues including human breast epithelia (HBL-100), human breast carcinoma (MCF-7), colon carcinoma (LoVo), liver carcinoma (HUH-7), lung carcinoma (A549), and prostate carcinoma (LNCaP and PC-3). The 293 cell lines was derived from human embryonic kidney cells transformed by adenovirus DNA. The cell lines were transfected with reporter constructs and and internal control plasmid, pCMVβ-Gal, and assays were performed as described in Example 3.

Figure 13:
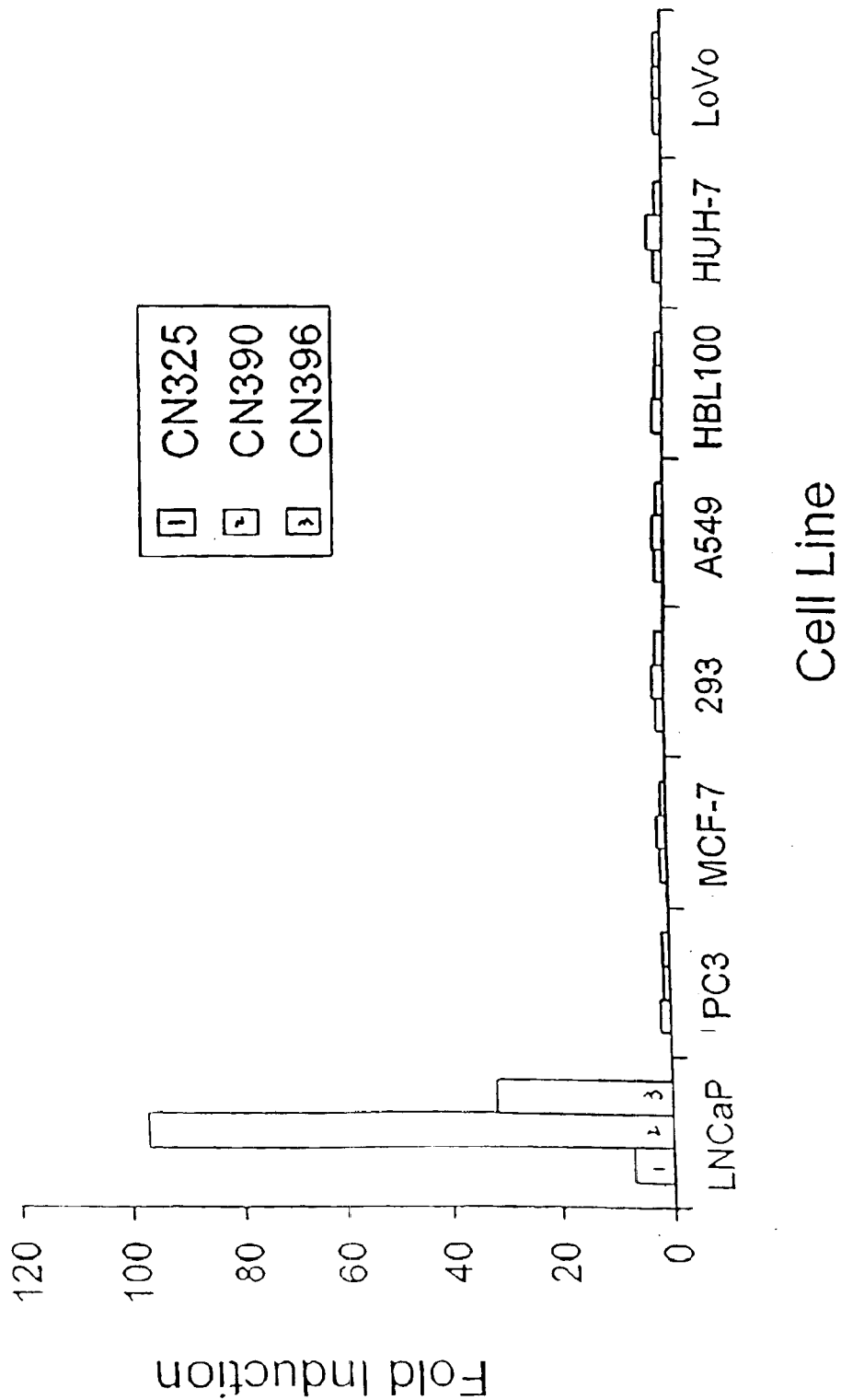
FIG. 13 is a bar graph depicting the induction of the luciferase-encoding gene by various hKLK2 enhancer/promoter constructs in various cells in the presence of R1881. The cell lines used represent several hormone-responsive tissues including prostate carcinoma (LNCaP and PC-3), human breast carcinoma (MCF-7), lung carcinoma (A549), human breast epithelia (HBL-100), liver carcinoma (HUH-7), and colon carcinoma (LoVo). The 293 cell line, which is derived from human embryonic kidney cells transformed by adenovirus DNA, was included as a non-hormone-responsive cell type.

The results are shown in FIG. 13. In LNCaP cells, CN390 and CN396 stimulate luciferase synthesis approximately 90- and 30-fold, respectively, in the presence of 1 nM R1881, while CN325 stimulated a 6-fold accumulation of luciferase, compared with control cultures to which no R1881 was added. In no other cell line did CN390 or CN396 lead to more than a 6-fold induction of luciferase synthesis. All three reporter constructs were inactive in the PC-3 prostatic carcinoma cell line. Lack of detectable androgen receptor is one feature which distinguishes this cell line from the LNCaP cell line. These results indicate that the hKLK2 enhancer functions in prostate cells expressing an androgen receptor.

Androgen Specificity of a 1.17-kb hKLK2 Enhancer

Figure 14:
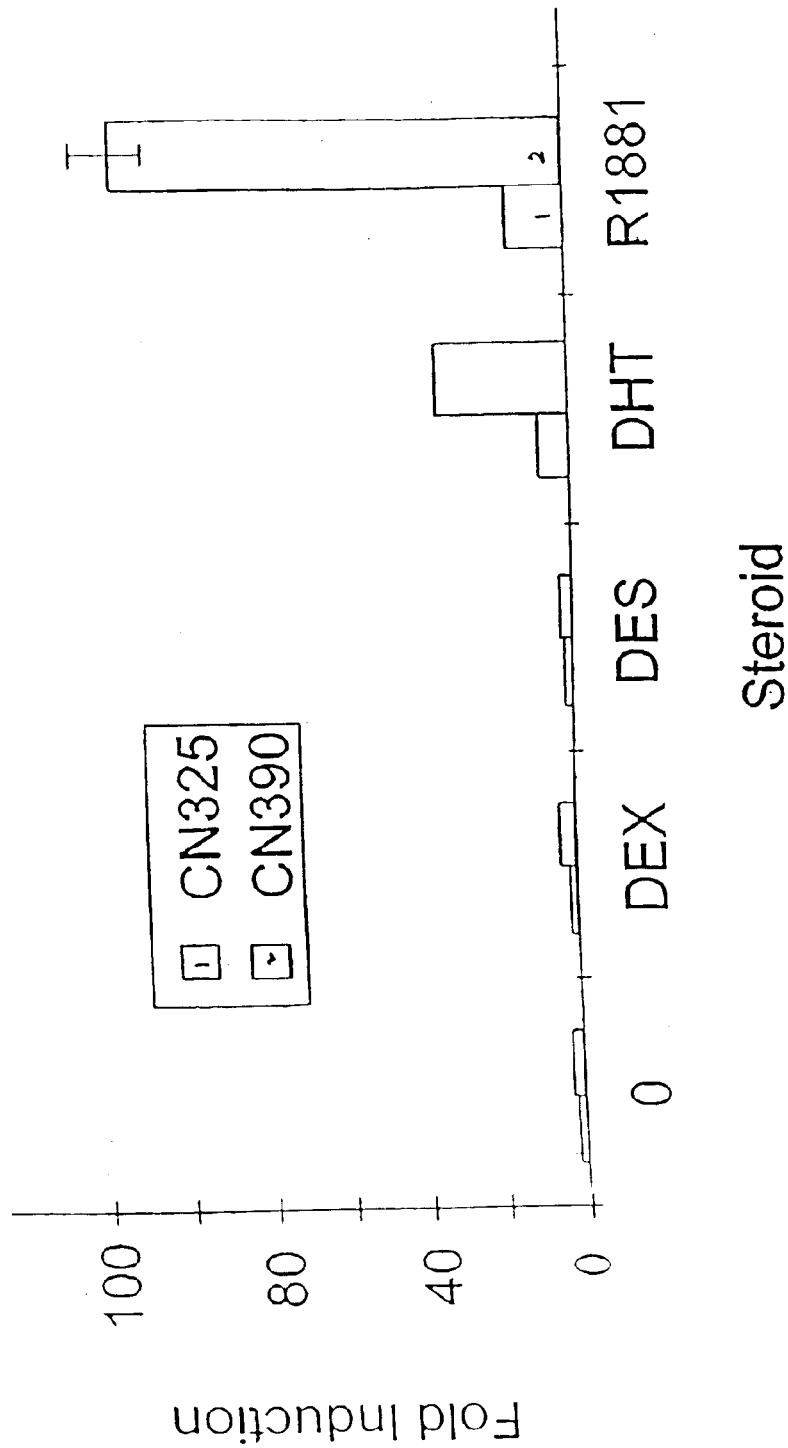
FIG. 14 is a bar graph depicting the induction of luciferase-encoding gene by a minimal hKLK2 promoter (CN325; left bars) and by 1.17-kb hKLK2 enhancer/minimal hKLK2 promoter (CN390, containing nucleotides 7200 to 8371 of SEQ ID NO:1; right bars) in the presence of various steroid hormones. The hormones tested were: DEX, a synthetic glucocorticoid; DES, a synthetic estrogen; dihydrotestosterone (DHT); and the synthetic androgen R1881.

To assess the androgen specificity of the hKLK2 enhancer, LNCaP cells transfected with CN390 (1.17-kb "full enhancer activity" hKLK2 enhancer/minimal hKLK2 promoter) were treated with various steroid hormones. As shown in FIG. 14, all of the androgens tested, including the naturally occurring androgen, dihydrotestosterone (DHT) and the synthetic androgen R1881, caused marked increases in luciferase activity when compared to cells not treated with hormones. Nonandrogenic compounds, including DES, a synthetic estrogen, and DEX, a synthetic glucocorticoid, showed little or no inducibility. These results suggest that the hKLK2 enhancer/promoter confers androgen receptor-mediated gene transcription control.

Figure 15:
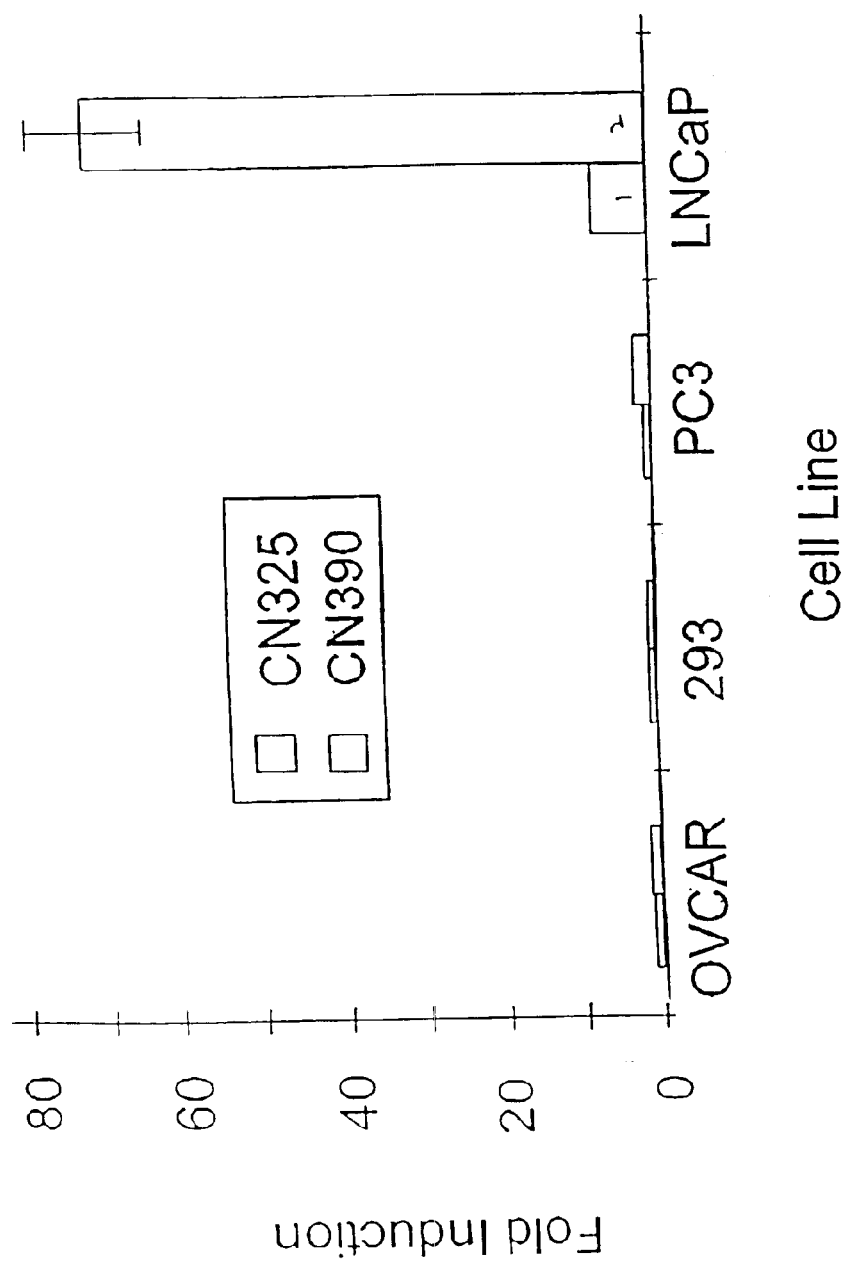
FIG. 15 is a bar graph depicting the induction of luciferase-encoding gene by a hKLK2 minimal promoter (CN325; left bars) and a 1.17-kb hKLK2 enhancer/minimal hKLK2 promoter (CN390; right bars) in cell lines lacking endogenous androgen receptor (AR) which were co-transfected with an expression construct which directs expression of the AR (OVCAR, 293 and PC3); and in LNCaP cells, which express endogenous AR.

Tissue-Specific Factors Involved in Regulating the Activity of the hKLK2 Enhancer To determine whether the lack of hKLK2 enhancer/promoter activity in the PC-3 cells and in the non-prostate cells tested was due primarily to the lack of functional androgen receptors in these cells, OVCAR, 293 and PC-3 cells were co-transfected with CN390 and with a plasmid which directs the expression of androgen receptor. As shown in FIG. 15, while CN390 leads to a 90-fold induction of luciferase expression in LNCaP cells, no induction was observed in the presence of R1881 in OVCAR, 293 or PC-3 cells which had been co-transfected with the AR expression plasmid. These results suggest that factors other than, and perhaps in addition to, androgen receptors are required for activating the regulatory sequences.

Example 8
Construction of Adenovirus Constructs in which Expression of One Adenovirus Gene is Controlled by an hKLK2 Promoter To generate hKLK2 adenovirus constructs, three hKLK2-related fragments which contain the hKLK2 full promoter were also amplified using the same strategy with the following synthetic oligonucleotides:
1) 42.100.1 in combination with 42.100.2;
2) 42.100.1 in combination with 42.100.3;
3) 42.100.1 in combination with 43.121.1 (5'-GAT CAC CGG TAA AGA ATC AGT GAT CAT CCC AAC-3'; SEQ ID NO:17; PinAI site underlined); and
4) 42.174.1 (5'-GAT CCG GCC GTG GTG CTC ACG CCT GTA ATC-3'; SEQ ID NO:18; EagI site underlined) in combination with
42.174.2 (5'-GAT CCG GCC GTG TCC ACG GCC AGG TGG TGC AG-3';
SEQ ID NO:19; EagI site underlined).

Consequently, four constructs, CN294, CN296, CN317 and CN310, respectively, were generated by ligating these fragments into pGEM-T vector, respectively. All these plasmids were described in Example 2, except CN310 which is identical to CN294 except EagI sites flank the insert.

hKLK2 Promoter-Driven E1A Ad5 Plasmid CN303

CN303 was produced by inserting the hKLK2 promoter just upstream of the E1A coding segment in a derivative of pXC-1, a plasmid containing the left hand end of the Ad5 genome.

CN124 is a derivative of construct pXC-1 which contains the wild-type left hand end of Ad5, including both E1A and E1B (McKinnon (1982) Gene 19:33–42). CN124 also has among other alterations, an artificial PinAI site at Ad5 nt 547 (just upstream of the E1A transcriptional start at nt 560 and the E1A coding segment beginning with ATG at 610). CN124 was linearized with PinAI and dephosphorylated with calf intestinal alkaline phosphatase (New English Biolab).

CN294 was digested with PinAI to free the hKLK2 promoter. The hKLK2 promoter was then ligated into the PinAI linearized CN124, producing CN303. CN304 is similar to CN303 except for the hKLK2 promoter fragment is in the reverse orientation.

Thus, construct CN303 contains the hKLK2 promoter inserted upstream of and operably linked to the E1A coding segment in the Adenovirus 5 genome.

hKLK2 Promoter-Driven E1B Ad5 Plasmid CN316

CN316 was produced by inserting the hKLK2-promoter just upstream of the E1B coding segment in a derivative of pXC-1, a plasmid containing the left hand end of the Ad5 genome.

CN124, described above, also contains an artificial EagI site at Ad5 nt 1682, just upstream of the E1B coding segment. The hKLK2 promoter was excised from CN310 with EagI and inserted into CN124 digested with EagI to produce CN316. CN316 contains the hKLK2 promoter immediately upstream of and operably linked to the E1B coding segment.

Example 9
Construction of Adenovirus Constructs in which Expression of One Adenovirus Replication Gene is Controlled by an hKLK2 Promoter or an hKLK2-TRE, and Expression of Another Adenovirus Replication Gene is Controlled by a Different Exogenous TRE Ad5 Construct Comprising hKLK2 Promoter Driven E1A and PSE (Prostate-Specific Antigen Promoter and Enhancer) Driven E1B (CN301)

CN301 was generated from CN125 by inserting an hKLK2 promoter upstream of the E1A gene.

CN125 is a pXC-1 derivative in which expression of the E1B gene is driven by PSE. A PinAI site lies upstream of the E1A gene, whose expression is driven by its wild-type promoter. CN125 was created by inserting PSE as an EagI fragment from construct CN105 into the EagI site immediately upstream of the E1B gene in CN124. CN105 contains the PSE region from −5322 to −3875 relative to the PSA transcription start site.

The hKLK2 promoter fragment was freed from CN294 by PinAI digestion and ligated into PinAI digested CN125 to create CN301. The final construct is a plasmid with the hKLK2 promoter driving E1A and PSE driving E1B.

Ad5 Constructs Comprising PSE Driven E1A and hKLK2 Promoter Driven E1B (CN323)

CN323 was constructed so that the expression of E1A is mediated by PSE, and expression of E1B is mediated by an hKLK2 promoter.

CN314 is a plasmid containing a PSE fragment in pGEM-T vector. This PSE fragment was amplified from CN706, an adenoviral construct in which a PSE drives expression of the E1A transcription unit in Ad5, with two synthetic oligonucleotides:
51.10.1 (5'-CTC ATT TTC AGT CAC COG TAA GCT TGG-3'; SEQ ID NO:20) and 51.10.2 (5'-GAG CCG CTC CGA CAC CGG TAC CTC-3'; SEQ ID NO:21).

The PSE fragment was isolated by digesting CN314 with PinAI and ligated into PinAI digested CN316 (described above). The final construct is a plasmid containing PSE driving E1A and the hKLK2 promoter driving E1B.

Generation of the Recombinant Adenovirus

Adenovirus containing hKLK2-TRE were generated by homologous recombination in 293 cells. Briefly, CN303 was co-transfected with BHG10 (which contains right hand end of the adenovirus genome), into 293 cells. The cells were overlaid with media, and infectious virus generated by in vivo recombination was detected by cytopathic effect and isolated. Plaque-purified stocks of a mutant, designated CN749, were established. The structure of the recombinant virus was characterized by PCR, restriction endonuclease digestion and Southern blot. CN749 is a full-length Ad5 with the hKLK2 promoter driving the expression of E1A.

Viruses CN747, CN754 were generated with the same approach except that the CN303 plasmid was replaced with CN301 and CN323, respectively. These attenuated viruses were constructed by engineering one or two exogenous transcriptional regulatory elements upstream of one or two essential Adenovirus 5 early genes; E1A and E1B. Schematically, CN749 is an attenuated adenovirus type 5 which contains one hKLK2 promoter cassette engineered upstream of the E1A gene. Similarly, CN747 is a virus whose E1A and E1B are under the control of the hKLK2 promoter and PSE respectively, and CN754 is the reciprocal of CN747.

Example 10

Figure 16:
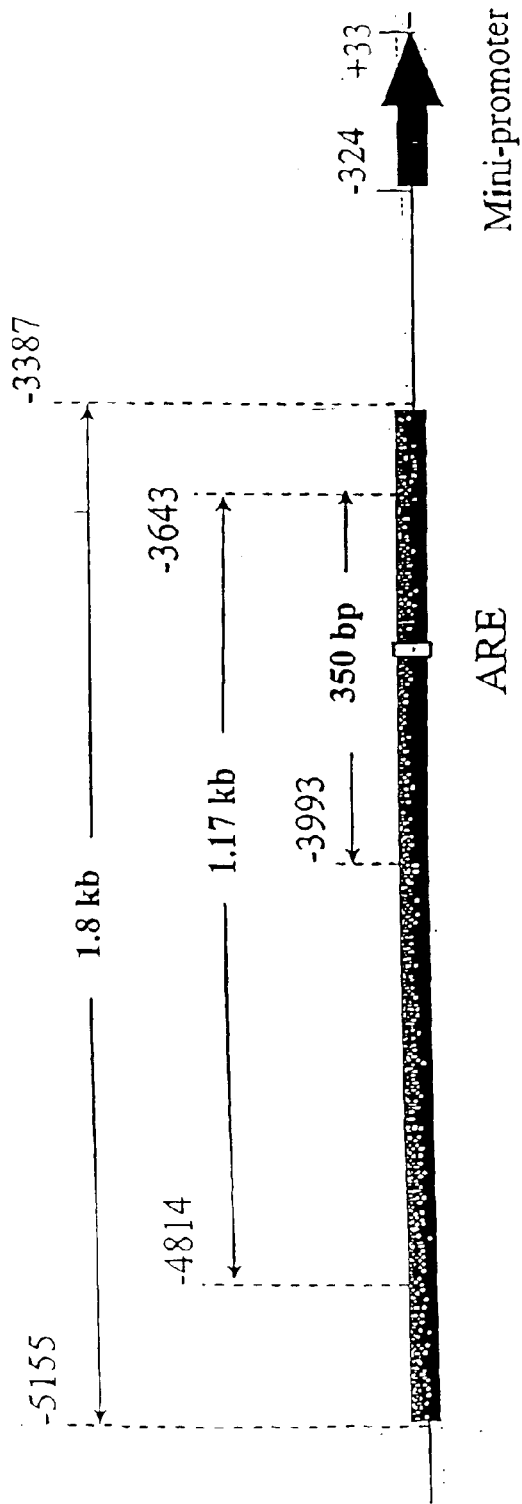
FIG. 16 is a schematic representation of the hKLK2-TREs used to generate the adenoviral constructs described in Example 10.

Generation of Adenoviral Constructs Comprising a First Adenoviral Gene Under Transcriptional Control of an hKLK2-TRE and a Second Adenoviral Gene Under Transcriptional Control of a Different Heterologous Promoter CN421 was constructed by inserting an hKLK2-TRE (comprising an hKLK2 enhancer from nucleotides −5155 to −3387 relative to the hKLK2 gene transcription start site (nucleotides 6859 to 8627 of SEQ ID NO:1) and an hKLK2 minimal promoter as in CN379; see Table 1 and FIG. 16) into CN306. The hKLK2-TRE fragment was amplified by PCR from CN379, digested with PinAI and ligated into similarly cut CN306, to produce CN421.

CN438 was constructed by inserting an hKLK2-TRE (comprising an hKLK2 enhancer from nucleotides −4814 to −3643 relative to the hKLK2 gene transcription start site (nucleotides 7200 to 8371 of SEQ ID NO:1) and a minimal hKLK2 promoter as in CN390; see Table 1 and FIG. 16) into CN306. The enhancer fragment was amplified by PCR from CN390, digested with PinAI and ligated into similarly cut CN306, to produce CN438.

CN306 was derived from CN124 by removing the endogenous 64-nucleotide E1A promoter.

CN321 was created from CN306 by inserting a large PSE fragment amplified from CN96.

CN326 was constructed from CN321 by inserting a rat probasin transcriptional regulatory element (PB-TRE) at the EagI site.

CN326 was constructed by inserting a PB-TRE into the EagI site of CN321. CN321 contains a PSE from CN96 at the PinAI site of CN306.

CN416 was constructed by inserting an hKLK2-TRE (comprising an hKLK2 enhancer from nucleotides −5155 to −3387 relative to the hKLK2 gene transcription start site (nucleotides 6859 to 8627 of SEQ ID NO:1) and an hKLK2 minimal promoter as in CN379; see Table 1 and FIG. 16) into CN321. The enhancer fragment was amplified by PCR from CN379, digested with EagI and ligated into similarly cut CN321, to generate CN416.

CN422 was constructed by inserting an hKLK2-TRE (comprising an hKLK2 enhancer from nucleotides −5155 to −3387 relative to the hKLK2 gene transcription start site (nucleotides 6859 to 8627 of SEQ ID NO:1) and an hKLK2 minimal promoter as in CN379; see Table 1 and FIG. 16) into CN369. CN369 is a derivative of CN306 in which the endogenous E1B promoter was removed. The hKLK2-TRE was amplified from CN379, digested with EagI, and ligated into similarly cut CN369 to produce CN422.

CN444 was constructed by replacing the hKLK2-TRE of CN442 with an hKLK2-TRE comprising an hKLK2 enhancer from nucleotides −4814 to −3643 relative to the hKLK2 transcription start site and a minimal hKLK2 promoter, as in CN390 (see Table 1 and FIG. 16). The hKLK2-TRE was amplified from CN390, digested with EagI, and ligated into similarly cut CN369, to produce CN444.

CN446 is similar to CN444, except that the endogenous E1B promoter was not removed. The hKLK2-TRE was amplified from CN390, digested with EagI, and ligated into similarly cut CN321, to produce CN446.

CN459 and CN460 are similar to CN444, except that each contains an hKLK2-TRE comprising an hKLK2 enhancer from nucleotides −3993 to −3643 relative to the hKLK2 transcription start site and a hKLK2 minimal promoter, as in CN396 (see Table 1).

CN463 was constructed by inserting an hKLK2-TRE (comprising an hKLK2 enhancer from nucleotides −4814 to −3643 relative to the hKLK2 transcription start site and a minimal hKLK2 promoter, as in CN390; see Table 1 and FIG. 16) into CN251. The hKLK2-TRE was excised from CN446 with EagI, and ligated into similarly cut CN251, to produce, CN463.

Generation of Recombinant Adenoviruses

Figure 17A:
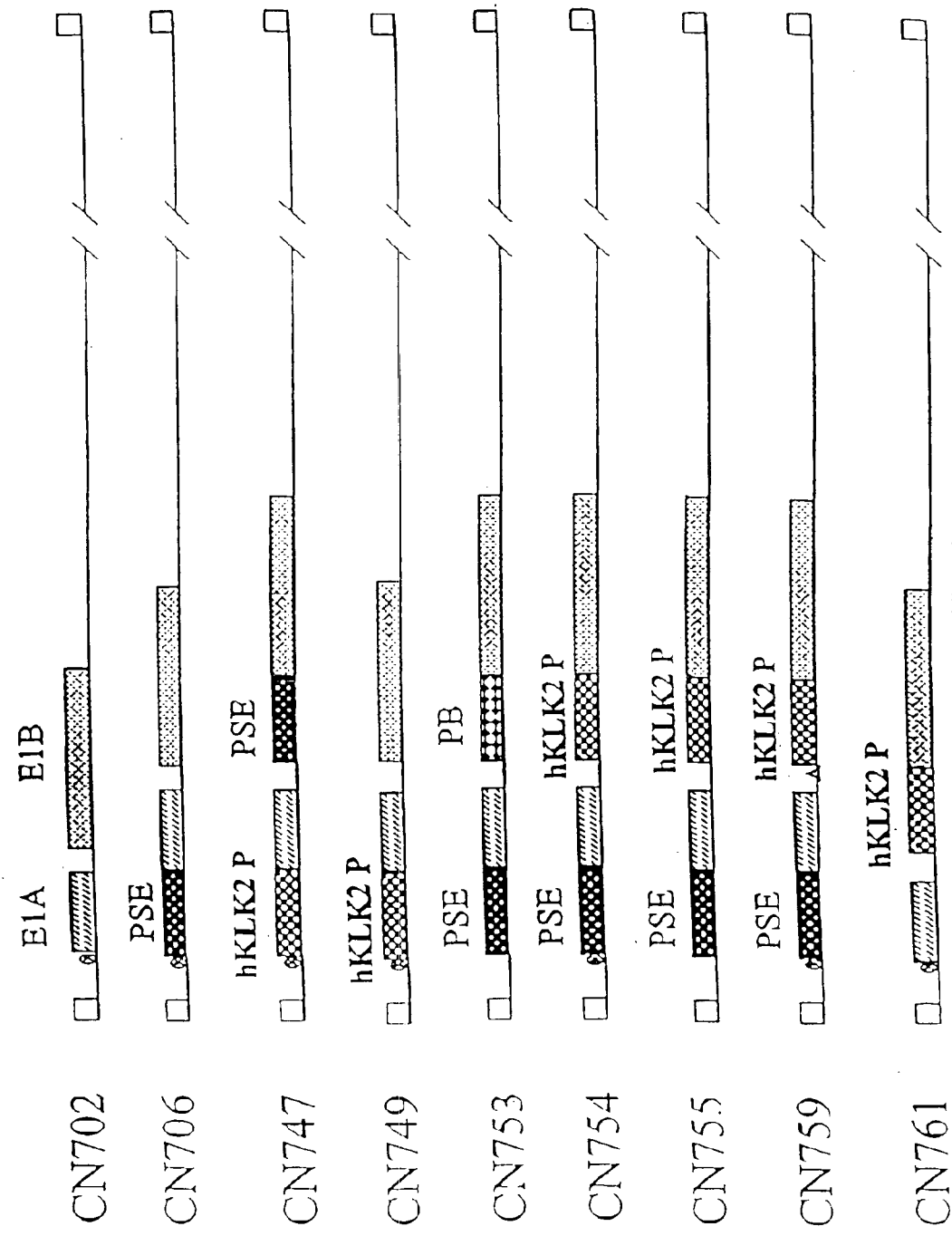
FIGS. 17A and 17B are schematic representations of the adenoviral constructs described in Example 10, in which adenoviral genes E1A and E1B are under transcriptional control of various TREs. The ovals indicate that the endogenous E1A is present. The triangles indicate that the endogenous E1B promoter was removed. Abbreviations for TREs are as follows: PSE: prostate specific antigen-TRE; hKLK2 P: hKLK2 promoter; PB: probasin TRE; hKLK2 (1.8 E+P): 1.8 kb hKLK2 enhancer and minimal hKLK2 promoter, as depicted in FIG. 16; hKLK2 (1.17 kb E+P): 1.17 kb hKLK2 enhancer and minimal hKLK2 promoter, as depicted in FIG. 16; hKLK2 (350 bp E+P): 350 bp hKLK2 enhancer and minimal hKLK2 promoter, as depicted in FIG. 16).
Figure 17B:
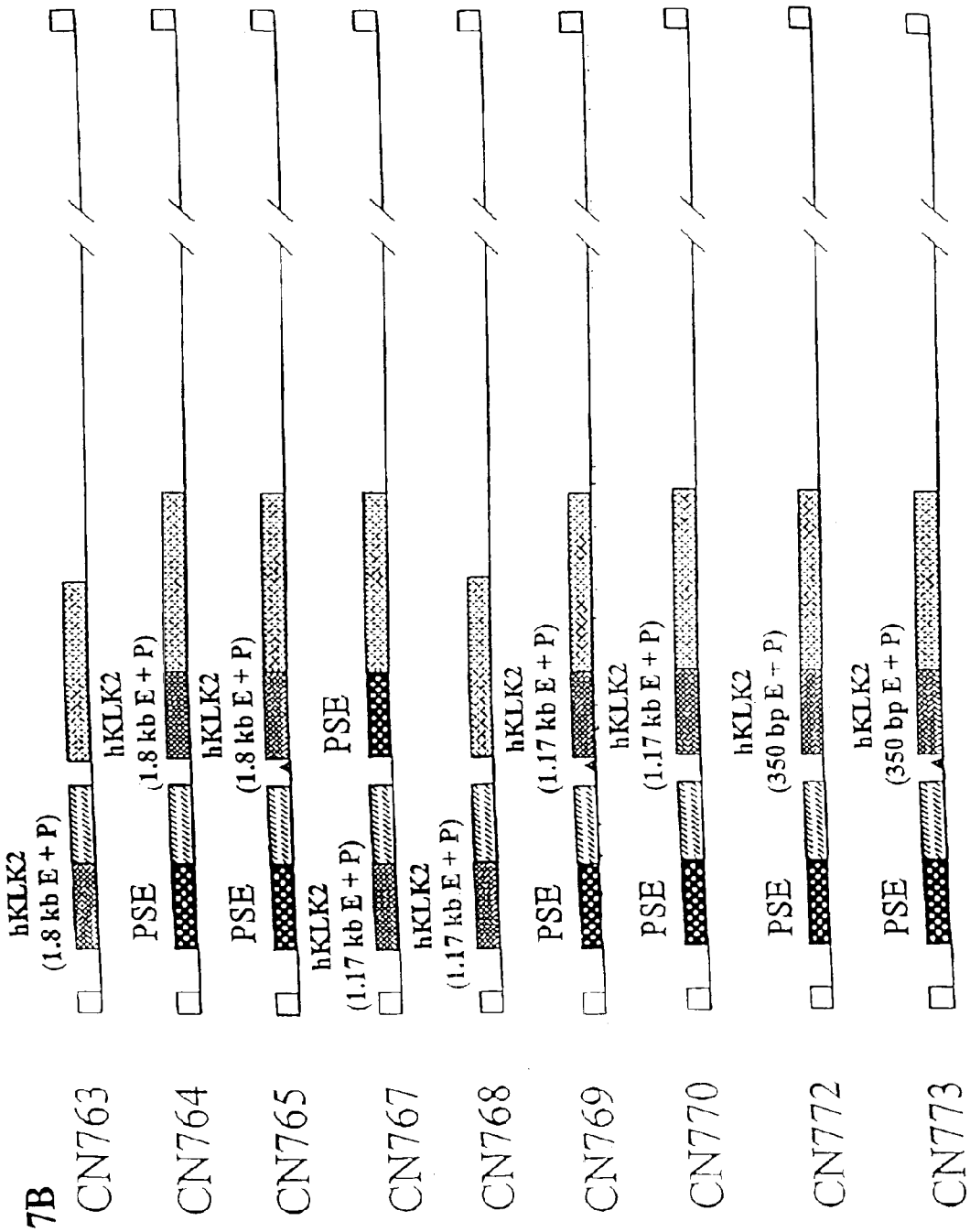

Viruses CN753, CN755, CN759, CN761, CN763, CN764, CN765, CN767, CN768, CN769, CN770, CN772 and CN773 were generated using the method as described in Example 9, from the parent plasmids CN326, CN328, CN398, CN316, CN421, CN416, CN422, CN436, CN438, CN444, CN446, CN459, CN460, and CN463, respectively. These viral constructs are shown schematically in FIGS. 17A and 17B. In a similar manner, CN774, in which the adenoviral E1A gene is under transcriptional control of a probasin TRE and the adenoviral E1B gene is under transcriptional control of the hKLK2-TRE contained within CN463, was constructed.

Example 11

In Vitro Characterization of Adenoviral Constructs Comprising an Adenoviral Gene Under Transcriptional Control of an hKLK2-TRE Plaque Assays To determine whether the adenoviral constructs described in Example 10 replicate preferentially in prostate cells, plaque assays were performed. Plaquing efficiency was evaluated in the following cell types: prostate tumor cell lines (LNCaP), breast normal cell line (HBL-100), ovarian tumor cell line (OVCAR-3, SK-OV-3), and human embryonic kidney cells (293). LNCaP cells express borh androgen receptor and PSA, while the other cell lines tested do not. 293 cells serve as a positive control for plaquing efficiency, since this cell line expresses Ad5 E1A and E1B proteins. The plaque assay was performed as follows: Confluent cell monolayers were seeded in 6-well dishes eighteen hours before infection. The monolayers were infected with 10-fold serial dilutions of each virus. After infecting monolayers for four hours in serum-free media (MEM), the media was removed and replaced with a solution of 0.75% low melting point agarose and tissue culture media. Plaques were scored two weeks after infection. CN702 has no modifications in its E1 region and is used as a wild type control. CN706 demonstrates selective cytotoxicity toward PSA-expressing cells in vitro and in vivo. Rodriguez et al. (1997) *Cancer Res.* 57:2559–2563.

TABLE 2

| Viruses | 293 | LNCaP | HBL-100 | OVCAR-3 |
|---|---|---|---|---|
| CN702 | 100 | 100 | 100 | 100 |
| CN706 | 100 | 23 | 2.4 | 5.5 |
| CN763 | 100 | 35 | 1.2 | 1.9 |
| CN768 | 100 | 29 | 1.3 | 3.9 |

TABLE 3

| Viruses | 293 | LNCaP | HBL-100 | OVCAR-3 | SK-OV-3 |
|---|---|---|---|---|---|
| CN702 | 100 | 100 | 100 | 100 | 100 |
| CN706 | 100 | 23 | 4.2 | 5.5 | 8.9 |
| CN764 | 100 | 31 | 0.25 | 0.032 | 0.003 |
| CN769 | 100 | 11 | 0.14 | 0.015 | 0.0008 |
| CN770 | 100 | 24 | 0.27 | 0.036 | 0.084 |
| CN772 | 100 | 29 | 0.27 | 0.096 | 0.21 |

TABLE 4

| Viruses | 293 | LNCaP | HBL-100 | OVCAR-3 |
|---|---|---|---|---|
| CN702 | 100 | 100 | 100 | 100 |
| CN706 | 100 | 33 | 2.5 | 3.4 |
| CN739 | 100 | 35 | 0.12 | 0.0023 |
| CN753 | 100 | 41 | 0.23 | 0.11 |

Tables 2, 3 and 4 show the results of plaque assays performed with the adenoviral vectors described in Example 10. The results are expressed as percent of wild-type adenovirus plaque-forming units (PFU) per ml. The average titer of duplicate samples for the viruses tested. The titer for a particular virus in all cell lines was normalized to its titer on 293 cells. Once the titers on a cell type were normalized to 293 cells, the normalized numbers of the recombinant viruses were compared to CN702. A ratio of less than 100 suggests that the virus tested plaques less efficiently than CN702. Conversely, a ratio greater than 100 suggests that the virus plaques more efficiently than CN702.

The following observations were made. First, hKLK2-TRE engineered adenoviruses demonstrate preferential replication in prostate tumor cells. Since this carcinoma expresses androgen receptors, the hKLK-TRE contained in the adenoviral vectors should be active in promoting the transcription of the adenovirus early genes. The data presented in Tables 2, 3 and 4 suggest that the hKLK2-TRE containing adenoviral vectors induce cytopathic effects with a lower efficiency than wild type adenovirus in prostate tumor cells. Second, hKLK2-TRE controlled adenoviruses show a dramatically lower plaquing efficiency in non-prostate tumor cells when compared to wild type. For example, in the ovarian carcinoma cell line OVCAR-3, CN763 and CN768 produced about 25 to 50-fold less plaques than wild type Ad5. The results are similar for these two viruses in HBL-100 cells, where virus replication is also severely compromised. Third, PSA-TRE adenoviral vectors and hKLK2-TRE adenoviral vectors give similar plaques in HBL-100 and OVCAR-3 cells. Thus, like PSA-TRE adenoviral vector CN706, hKLK2-TRE adenoviral vectors were significantly attenuated relative to wild-type adenovirus in non-prostate cells, but these vectors grew comparably in prostate tumor cells.

Cytopathic Effects

Figure 18:
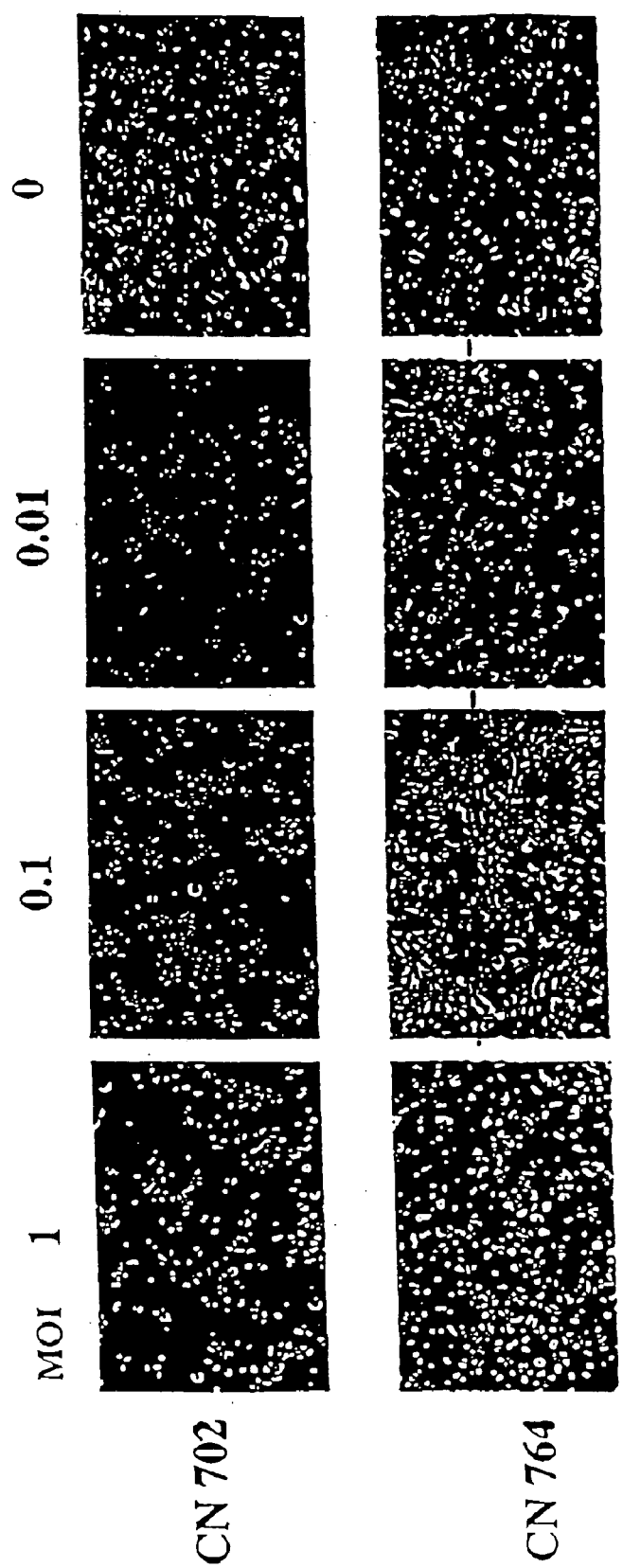
FIG. 18 shows the cytopathic effects of CN702 and CN764 at various multiplicities of infection on human microvascular endothelial cells.

To characterize the differential viral replication and cytopathic effects (CPE), CPE assays were performed as follows. Cells were infected with virus at increasing multiplicities of infection (MOI) and monitored for cytopathic effect. Assays were terminated when complete cytolysis of the monolayers was observed at an MOI of 0.01 with wild-type adenovirus. One primary, non-immortalized human microvascular endothelial cell line (hMVEC) was chosen to test its sensitivity to CN764 and wild-type adenovirus (CN702) infection, in vitro. As shown in FIG. 18, CN702 caused complete monolayer cytolysis of hMVECs at MOIs as low as 0.01 within 10 days. In contrast, CN764 infected hMVEC monolayers did not show significant cytopathic effects at the same time points with MOIs of 10, 1.0, 0.1 and 0.01. Cytolysis of hMVECs equivalent to that seen with wild-type adenovirus was only evident at MOIs between 100 and 1000 times as high (MOI>10).

Thus, CN764-mediated cytolysis is significantly attenuated relative to wild-type adenovirus in primary normal human cells.

Differential Viral Replication

Figure 19:
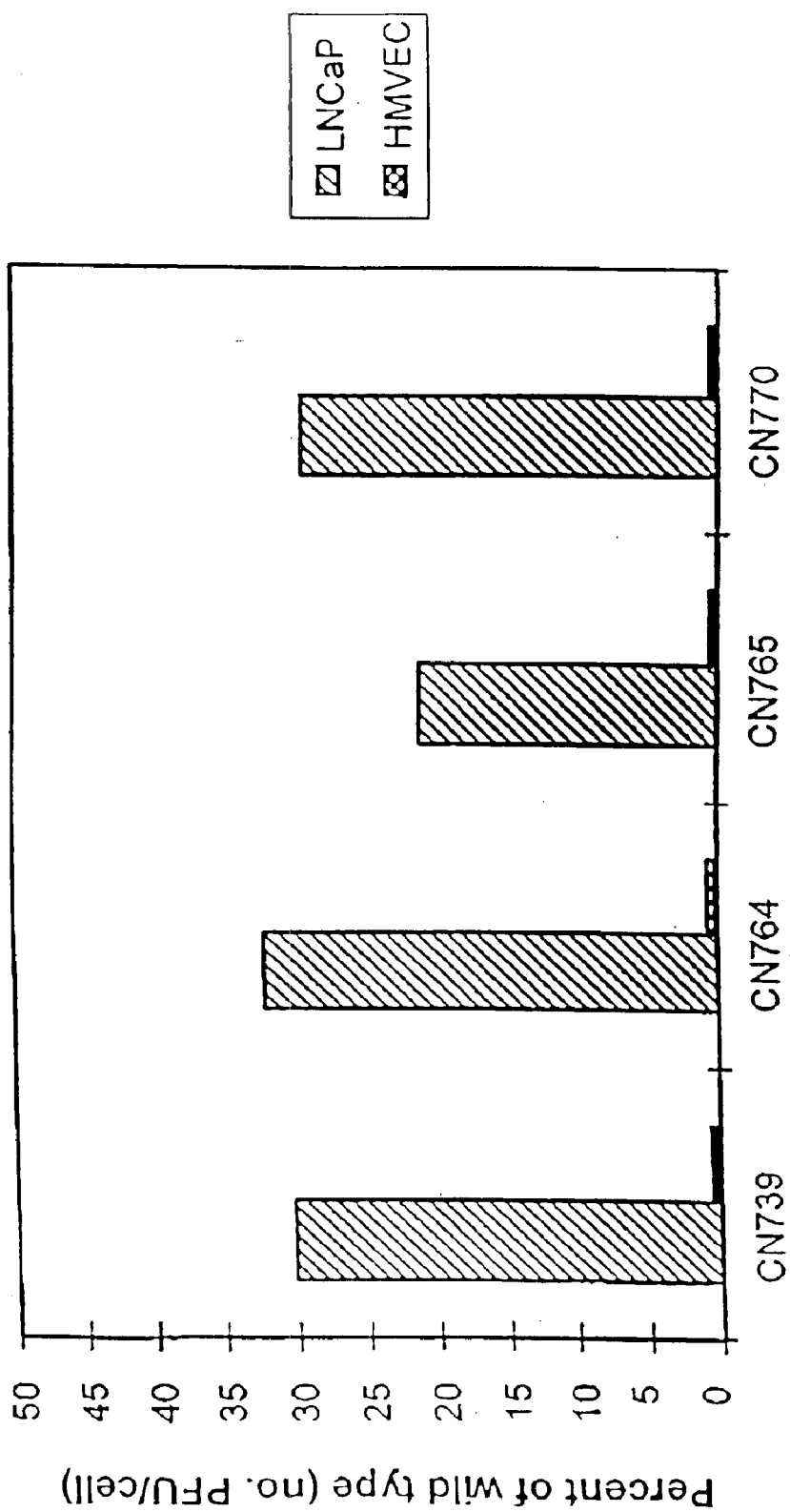
FIG. 19 is a bar graph showing the number of plaque-forming units, expressed as percentage of plaques obtained with wild-type adenovirus, obtained when either LNCaP cells (hatched bars) or HMVEC cells (bars with square pattern) were infected with adenoviral vectors CN739, CN764, CN765 or CN770.

To determine if levels of virus replication correlate with the cytopathic effects of CN739 in prostate tumor cells or human normal cells, virus replication titration was carried out on PSA producing prostate tumor cells (LNCaP) and primary human microvascular endothelial cells (hMVECs). Cells were grown to 70–90% confluence and infected with either wild-type adenovirus (CN702) or CN764, CN765, CN770 for 90 min at a MOI of 10. Fifty-five hours after infection, the virus was released from the cells by three freeze/thaw cycles, and the resulting supernatant was titered on 293 cells. The amount of CN739 produced 56 hours after infection was normalized against the amount of wild-type virus produced in the same cell line during the same time period. The data, shown in FIG. 19, indicate that hKLK2-TRE adenovirus construct titers were 30% of CN702 titers in LNCaPs, but were reduced to less than $\frac{1}{100}$ those of the wild-type viruses in normal cells. These data suggest that CN764-like viruses replicate poorly in primary normal human cells, and are somewhat attenuated in prostate cancer cells.

Example 12
Testing Cytotoxic Ability of Adenovirus Vectors on Prostate Carcinoma Tumor Xenografts An especially useful objective in the development of prostate-specific adenoviral vectors is to treat patients with prostate carcinoma. An initial indicator of the feasibility is to test the vectors using a technique known in the art, such as testing the vectors for cytotoxicity against prostate carcinoma cells such as prostate xenografts grown subcutaneously in Balb/c nu/nu mice. Mice are given subcutaneous injections with $1 \times 10^7$ prostate carcinoma cells, such as LNCaP, in PBS. Tumor cells can be tested for hK2 activity by assaying hK2 in serum using standard assays (for example, ELISA).

For this experiment, test virus vectors are introduced into the mice either by direct intratumoral, intravenous or intraperitoneal injection of approximately $10^8$ pfu of virus (if administered as a packaged virus) in 0.1 ml PBS+10% glycerol or intravenously via the tail vein. If administered as a polynucleotide construct (i.e., not packaged in virus), 0.1 µg to 100 µg or more can be administered. Tumor sizes are measured and, in some experiments, blood samples are taken weekly. The effect of intratumoral injection of an adenovirus vector of the present invention on tumor size and serum androgen receptor levels is compared to sham treatment.

While it is likely that a therapeutic based on the viruses described here would be given intralesionally (i.e., direct injection), it would also be desirable to determine if intravenous (IV) administration of the virus can affect tumor growth. If so, then it is conceivable that the virus could be used to treat metastatic tumor deposits inaccessible to direct injection. For this experiment, groups of five mice bearing prostate cancer tumors are inoculated with $10^8$ pfu of an adenoviral vector of the present invention by tail vein injection, or $10^8$ pfu of a replication defective adenovirus (CMV-LacZ) to control for non-specific toxic effects of the virus, or with buffer used to carry the virus. The effect of IV injection of the adenoviral vector on tumor size is compared to the sham treatment.

Example 13
Construction of an Adenoviral Vector Containing the Coding Region for the Adenovirus Death Protein (ADP)

In an adenoviral vector (such as those described above), a deletion can be created in the E3 region to accommodate an hKLK2-TRE in the E1 region. The ADP coding sequence from Ad2 can be reintroduced into the E3 region of Ad5 as follows.

An ADP cassette is constructed using overlap PCR. The Y leader, an important sequence for correct expression of some late genes, is PCR-amplified using primers:

```
5' GCCTTAATTAAAAGCAAACCTCACCTCCG...Ad2 28287bp    (37.124.1) (SEQ ID NO:22); and 5' GTGGAACAAAAGGTGATTAAAAAATCCCAG...Ad2 28622bp.  (37.146.1) (SEQ ID NO:23).

The ADP coding region is PCR amplified using primers

5' CACCTTTTGTTCCACCGCTCTGCTTATTAC...Ad2 29195bp   (37.124.3) (SEQ ID NO:24) and

5' GGCTTAATTAACTGTGAAAGGTGGGAGC...Ad2 29872bp     (37.124.4) (SEQ ID NO:25).
```

The two fragments were annealed and the overlap product was PCR amplified using primers 37.124.1 and 37.124.4. The ends of the product were polished with Klenow fragment and ligated to BamHI cut pGEM-72 (+) (CN241; Promega, Madison, Wis.). The ADP cassette was excised by digesting CN241 with Pac 1 restriction endonuclease and ligated with two vectors, CN247 and CN248 generating plasmids CN252 and CN270, respectively. CN247 contains a unique PacI site in the E3 region and was constructed as follows. A plasmid containing the full length Ad5 genome, TG3602 (Transgene, France), was digested with BamHI and religated to yield CN221. The backbone of this plasmid (outside of the Ad5 sequence) contained a PacI site that needed to be removed to enable further manipulations. This was effected by digesting CN221 with PacI and polishing the ends with T4 DNA polymerase, resulting in CN246. CN246 was digested with AscI and AvrII (to remove intact E3 region). This fragment was replaced by a similarly cut fragment derived from BHG11. The resulting plasmid, CN 247, contained a deleted E3 region and a PacI site suitable for insertion of the ADP cassette fragment (described above). Ligation of CN247 with the ADP cassette generated CN252.

CN248 (a construct that would allow introduction of an ADP cassette into a Ad that also contains a deletion/substitution in the E4 region) was made as follows. The E4 region was deleted by digesting CN108, a construct that contains right hand end Ad5 sequence from the unique EcoRI site in the E3 region, with AvrII and AflIII. The only E4 ORF necessary for viral replication, ORF 6, was reintroduced by PCR amplifying the ORF with primers, 33.81.1 (Ad5 33096):
  GCAGCTCACTTAAGTTCATGTCG (SEQ ID NO:26)

33.81.2 (Ad5 34084):
  TCAGCCTAGGAAATATGACTACGTCCG (SEQ ID NO:27)

The resulting plasmid is CN203. CN203 was digested with EcoRI and ligated to CN209, a shuttle plasmid, to generate CN208. In the final cloning step, CN208 was digested with AscI and AvrII and ligated to similarly cut E4 deletion/substitution with the ADP cassette.

Both CN252 and CN270 contain an E3 deletion. In addition, CN270 lacks some sequence in the E4 region as previously described. Adenoviral vectors are obtained via in vitro ligation of (1) appropriately prepared vial DNA digested with BamHI and (2) CN252 or CN257 also digested with BamHI. The ligation product is used to transfect 293 cells. Plaque assays are performed as described above.

Example 14
Characterization of an E3 Deleted Adenovirus, CN751, that Contains the Adenovirus Death Protein Gene An adenovirus death protein mutant, CN751, was constructed to test whether such a construct may be more effective for cytotoxicity. The adenovirus death protein (ADP), an 11.6kD Asn-glycosylated integral membrane peptide expressed at high levels late in infection, migrates to the nuclear membrane of infected cells and affects efficient lysis of the host. The Adenovirus 5 (Ad5) E3 region expresses the adp gene.

Construction of CN751

CN751 was constructed in two parts. First, an E3 deleted platform plasmid that contains Ad5 sequence 3' from the BamHI site at 21562 bp was generated. The Ad2 adp was engineered into the remainder of the E3 region of this plasmid to yield CN252 (this cloning has been previously described). To construct the second part, the 5' Ad5 sequence necessary for CN751 was obtained by digesting purified CN702 DNA with EcoRI and isolating the left hand fragment by gel extraction. After digesting CN252 with EcoRI, the left hand fragment of CN702 and CN252 were ligated. 293 cells were transfected with this ligation mixture by lipofection transfection and incubated at 37° C. Ten days later, the cells were harvested, freeze-thawed three times, and the supernatant was plaqued on 293 monolayers. Individual plaques were picked and used to infect monolayers of 293 cells to grow enough virus to test. After several days, plate lysates were screened using a polymerase chain reaction (PCR) based assay to detect candidate viruses. One of the plaques that scored positive was designated CN751.

Structural Characterization of CN751

The structure of CN751 was confirmed by two methods. First, primers 37.124.1 (5' gccttaattaaaagcaaacctcacctccg Ad2 28287bp; SEQ ID NO:22) and 37.124.4 (5' ggcttaat-taactgtgaaaggtgggctgc Ad2 29872bp; SEQ ID NO:25) were used to screen candidate viruses by PCR to detect the presence of the adp cassette. CN751 produced an extension fragment consistent with the expected product (1065bp). Second, CN751 was analyzed by Southern blot. Viral DNA was purified, digested with PacI, SacI, and AccI/XhoI, and probed with a sequence homologous to the ADP coding region. The structure of CN751 matched the expected pattern.

In Vitro Characterization of CN751

Two experiments were conducted to examine the cytotoxicity and virus yield of CN751. In the first study, CN751's cytotoxicity was evaluated in LNCaP cells by measuring the accumulation of a cytosolic enzyme, lactate dehydrogenase (LDH), in the supernatant over several days. The level of extracellular LDH correlates with the extent of cell lysis. Healthy cells release very little, if any, enzyme, whereas dead cells release large quantities. LDH was chosen as a marker because it is a stable protein that can be readily detected by a simple protocol. CN751's ability to cause cell death was compared to that of CN702, a vector lacking the ADP gene, and Rec700, a vector containing the ADP gene.

Monolayers of LNCaP cells were infected at an MOI of one with either CN702, Rec700 (adp+control), or CN751 and then seeded in 96 well dishes. Samples were harvested once a day from one day after infection to five days after infection and scored using Promega's Cytotox 96 kit. This assay uses a coupled enzymatic reaction which converts a tetrazolium salt to a red formazan product that can be determined in a plate reader at 490 nm.

Figure 20:
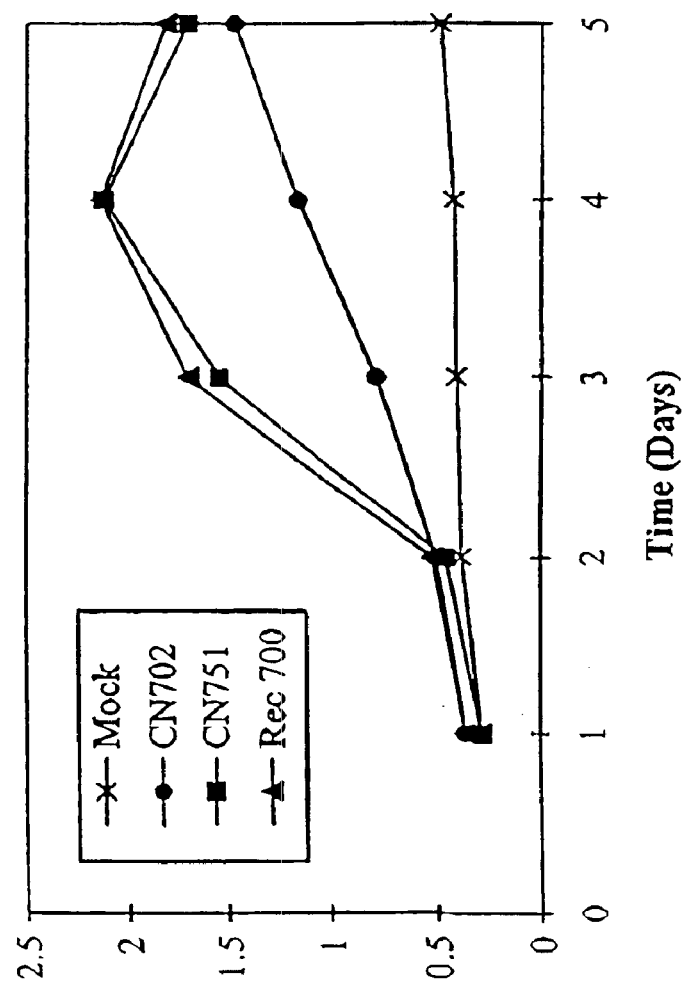
FIG. 20 is a graph depicting cytotoxicity of an adenoviral vector containing the coding sequence for adenoviral death protein (ADP), CN751 (solid squares), compared to control CN702 (solid circles), Rec 700 (solid triangles) and mock infection (Xs).

Since the absorbance of a sample corresponds to the level of LDH released from infected cells, a plot of how a sample's absorbance changes with time describes how efficiently the viruses studied induce cell lysis (FIG. 20). Each data point represents the average of sixteen separate samples. The results suggest that CN751 kills cells more efficiently than the adp-control, CN702, and similarly to the adp+control, Rec700. The concentration of LDH in the supernatant increases rapidly from two days and reaches a maximum at four days in wells infected with CN751. In contrast, LDH concentration in the supernatant of CN702 infected cells begins to rise slowly at two days and continues until the conclusion of the experiment. Significantly, the amount of LDH released from CN751 infected cells at three days is two times that released from CN702 infected cells. In sum, the virus yield data demonstrate that adenovectors with the ADP gene release more virus.

Figure 21:
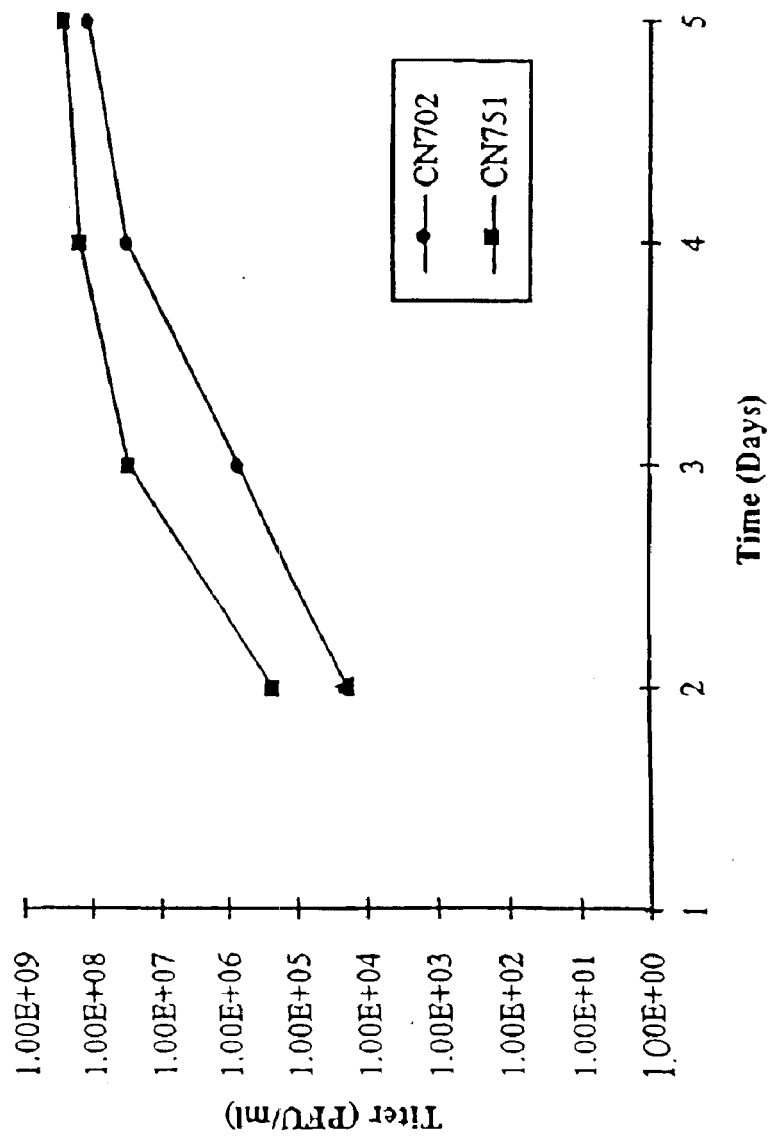
FIG. 21 is a graph comparing extracellular virus yield of CN751 (solid squares) and CN702 (solid circles).

Not only is it important for Ad vectors to kill cells efficiently, they must also be able to shed progeny that can infect other cancer cells. Viral vectors that can shed large amounts of virus might be better therapeutics than those that shed only small amounts. A virus yield assay was undertaken to evaluate whether CN751 can induce the efficient release of its progeny from the infected cell. A549 cells were infected at an MOI of five. Supernatant was harvested at various times after infection and titered on 293 cells to determine the virus yield (FIG. 21). The data suggest that cells infected with CN751 shed virus more efficiently than those infected with CN702. At forty-eight hours post infection, CN751 infected cells released ten times more virus than CN702 infected. At seventy-two hours post infection, CN751 infected cells released forty times more virus. The data demonstrate that adenovectors with the ADP gene kill cells more efficiently than adenovectors that lack the ADP gene.

In vivo Characterization of CN751

Figure 22:
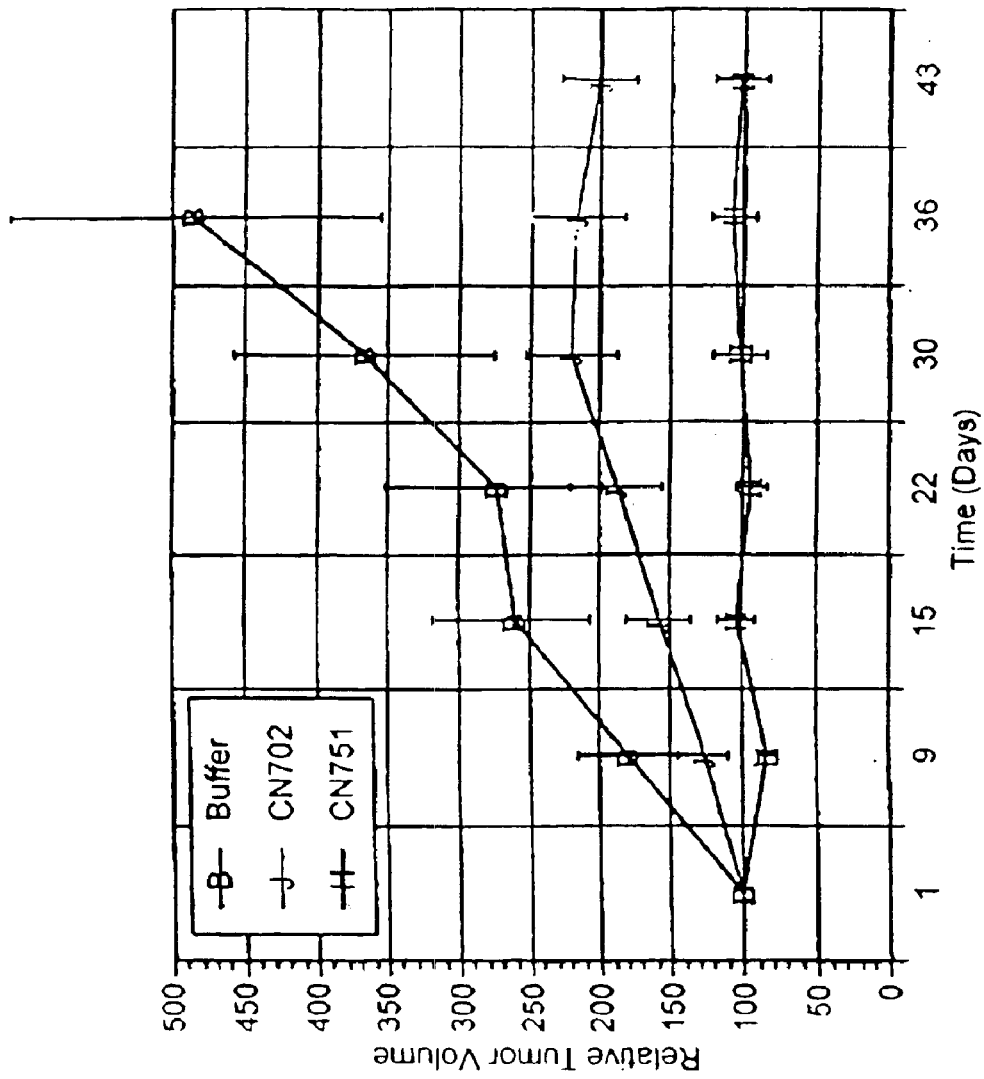
FIG. 22 is a graph comparing tumor volume in mice harboring LNCaP tumor xenografts challenged with CN751 ("H"), CN702 ("J"), or buffer ("B").

LNCaP nude mouse xenografts were challenged with a single intratumoral dose ($1 \times 10^4$ particles/mm$^3$ tumor) of either CN751, a vector containing the ADP gene, or CN702, a vector lacking the gene. A third group of tumors was treated with buffer alone. The tumors were monitored weekly for six weeks and their relative volume was graphed against time. The results are shown in FIG. 22. Error bars represent the standard error for each sample group. The initial average tumor volume for CN751 treated animals (n=14) was 320 mm$^3$ for CN702 treated (n=14), and 343 mm$^3$ for buffer treated (n=8). The data suggest that CN751 kills tumor cells more effectively than CN702. On average, tumors challenged with CN751 remained the same size throughout the course of the experiments while nine out of fourteen tumors (64%) regressed. Those treated with CN702 doubled in size. Buffer treated tumors grew to nearly five times their initial volume. The Students T-test indicates that the difference in tumor size between CN751 and CN702 treated tumors was statistically significant from day 7 (p=0.016) through the end of the experiment (p=0.003).

Example 15

Drug Screening Assays

Figure 23A:
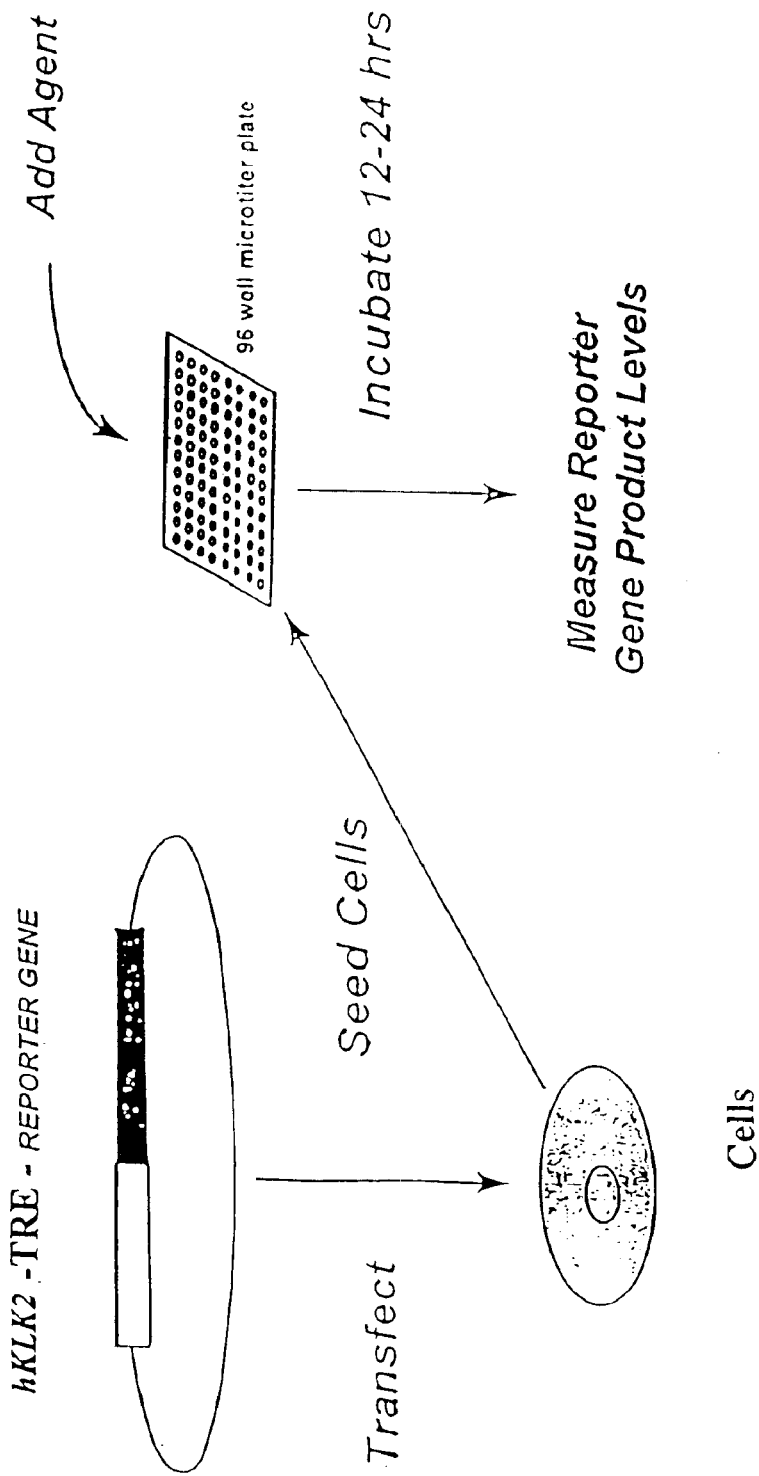
FIGS. 23A and 23B depict two different assay methods for identifying agents that have the ability to modulate expression of a polynucleotide operably linked to an hKLK2-TRE.
Figure 23B:
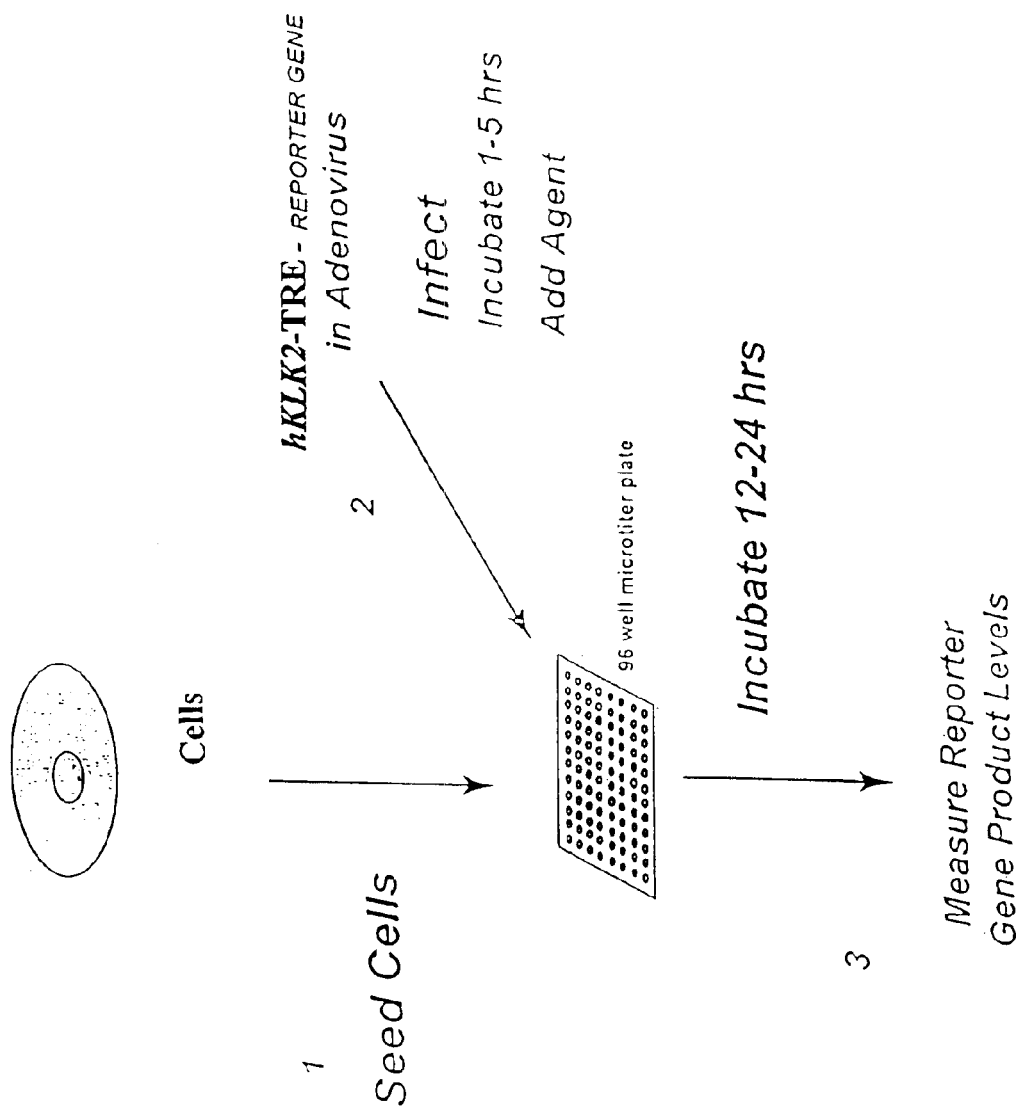

FIGS. 23A and 23B present schemes for using an hKLK2-TRE in screening assays for agents that modulate hKLK2 gene expression. These assays are also suitable for automated high through-put random drug screening.

Screening Methods Using Plasmid Vectors

A DNA sequence containing an hKLK2-TRE is linked to a DNA sequence encoding a second moiety that can serve as a detectable tag, e.g. luciferase, and is stably or transiently transfected into a suitable cell line such as LNCaP cells (FIG. 23A). Cells are plated into a 96-well microtiter plate. After a suitable time, for example, about 12 hours, the agent whose ability to affect hKLK2 gene expression is to be tested is added. Control samples include no test agent. After a suitable incubation period, the test wells are washed, and luciferase activity is measured. Standard methods exist for assaying luciferase enzyme activity. Ow et al. (1986) Science 234:856 and de Wet et al. (19987) Mol. Cell. Biol. 7:725. Test wells showing a significantly higher or significantly lower luciferase activity compared with the control are then examined further to confirm an effect on hKLK2 gene expression.

Screening Methods Using Replication-Defective Adenovirus

Cells such as LNCaP cells are plated in 96-well microtiter plates (FIG. 23B). After a suitable time, for example, about 12 hours, the cells are infected with a recombinant adenovirus in which a gene or genes essential for replication, such as E1A and E1B, are replaced with an hKLK2-TRE operably linked to a reporter gene, e.g., luciferase. After a suitable incubation period, the agent whose ability to modulate hKLK2 gene expression is to be tested is added. Control samples include no test agent. After a suitable incubation period, the test wells are washed and luciferase activity is measured by known methods. Test wells showing a significantly higher or significantly lower luciferase activity compared with the control are then examined further to confirm an effect on hKLK2 gene expression.

Example 16

Electrophoretic Mobility Shift Assays (EMSA)

Nuclear extracts containing DNA-binding proteins were prepared from LNCaP and HeLa cells as described. Schuur et al. (1993) *Cell Growth and Differ.* 4:761–768. This protocol is a modification of that described by Dignam et al. (1983) *Nucleic Acids Res.* 11:1475–1489. Approximately $1 \times 10^8$ LNCaP cells or HeLa cells were harvested, washed with PBS, then collected in two 50-mL centrifuge tubes. The cells were pelleted by centrifugation for 10 minutes at 3,000 rpm at 4° C. The supernatant was discarded and the pellet was resuspended in 5× volumes of hypotonic buffer (10 mM HEPES, pH 7.9, 1.5 MM $MgCl_2$, 10 mM KCl, 0.2 mM PMSF, 0.5 mM DTT). The cells were pelleted as before, the supernatant discarded, and the pellet resuspended in 3× volumes of hypotonic buffer, then kept on ice for 10 minutes. After this incubation, the cells were then homogenized in a Dounce homogenizer, using a type B pestle. After the cells were about 90% lysed (as determined by trypan blue dye exclusion test performed on a sample), the mixture was pelleted by centrifugation for 15 minutes at 4,000 rpm (approximately 3300× g) at 4° C. The supernatant was discarded, and the pellet resuspended in low salt buffer (20 mM HEPES, pH 7.9, 25% glycerol, 1.5 mM $MgCl_2$, 0.02 M KCl, 0.2 mM EDTA, 0.2 mM PMSF, and 0.5 mM dithiothreitol). 0.5× volume of high salt buffer (same as low salt buffer, but has 1.2 M KCl) was added dropwise to the mixture and the mixture was incubated at room temperature for 30 minutes on a shaker. After incubation, the mixture was centrifuged for 30 minutes at 13,200 rpm (approximately 25,000× g) at 4° C. The crude extract was dialyzed into binding buffer (20 mM HEPES pH 7.9, 20% glycerol, 100 mM KCl, 0.2 mM EDTA, 0.2 mM phenylmethylsulfonyl fluoride, 0.5 mM DTT) and stored at −80° C.

A DNA probe was created from a PCR product spanning from −3899 to −3699 (primers 58.44.3 and 58.44.4) relative to the start of hKLK2 gene transcription. The primers used were 58.44.3 (5' TAC TAG CAA ACT TGT CCA GTC 3'; SEQ ID NO:35) and 58.44.4 (5' TAG CCT TGC AAG ATG GTA TCG 3'; SEQ ID NO:36) and the template was CN379. This probe, within the core of the enhancer, contains the ARE located at about −3822 to about −3808 (from about nucleotide 8192 to about 8206 of SEQ ID NO:1). A probe downstream of this core, corresponding to a sequence from −2358 to −2555 relative to the start of hKLK2 gene transcription, was also synthesized. The primers used were 51.70.1 (5' GGA AAT CAA ACA CAA CCA CAT CCC 3'; SEQ ID NO:37) and 58.160.2 (5' TGT GCC AGC ATC AGC TTC ATC TGT ACC 3'; SEQ ID NO:38), and CN312 was used as the template.

The PCR reaction mixtures which were used to make the probes contained 2U Taq polymerase (Boehringer-Mannheim), 10 ng of CN379 (CN312 for negative probe), 10 μL PCR buffer plus $Mg^{2+}$ supplied by the manufacturer, 200 μM dNTPs, and 50 pmol of each primer. The reactions were initially denatured at 94° C. for 2 minutes followed by 25 cycles of amplification (94° C. for 15 seconds, 55° C. for 30 seconds, and 72° C. for 30 seconds). A final extension of 72° C. for 5 minutes followed amplification.

Labeled DNA probes were made by modifying the PCR protocol above. 10 pmol of each primer were labeled with $^{32}$P using T4 polynucleotide kinase (Amersham) in a 10 μL reaction. The reactions were incubated at 37° C. for 30 minutes and added to 8 μL of PCR mixture described above. The samples were cycled as described above. Following amplification, the samples were electrophoresed through a 5% acrylamide (19 acrylamide:1 bis-acrylamide), 0.5× TBE gel at 150V. Labeled PCR product was detected by autoradiography. A gel slice containing the labeled DNA was excised, minced, and resuspended in TE overnight at 37° C. to elute the DNA. Labeled DNA in the supernatant was removed and an aliquot was counted before setting up the binding reactions. Labeled probe was diluted to 20,000 cpm/μL with water.

Binding reactions included 4–8 μg (total protein) nuclear extract, 3 μg poly (dI-dC) (Pharmacia Biotech), 20,000 cpm probe, 3 μL unlabeled PCR product as a competitor and binding buffer to 20 μL. Binding reactions were incubated on ice for 20 minutes, and electrophoresed through 4% acrylamide (19 acrylamide: 1 bis-acrylamide), 0.25× TBE gels at 150V for 3.5–4.0 hours at 4° C. The gels were dried and exposed to Hyperfilm ECL (Amersham) at −80° C. for 15–96 hours on a Molecular imaging screen (BioRad).

DNA-Protein Complexes on the hKLK2 Enhancer

After identifying and characterizing the hKLK2 enhancer, a segment of the core region (from −3899 to −3699) that contains the AREII was assessed for its ability to form DNA-protein complexes. A downstream region (from −2358 to −2555) found to be unnecessary in the activation of this enhancer was also assessed for its ability to form DNA-protein complexes. These regions were amplified by PCR with end-labeled primers to probe LNCaP and HeLa cell nuclear extracts in EMSA tests. Both regions were also amplified by PCR to produce specific and non-specific competitors.

Figure 25A:
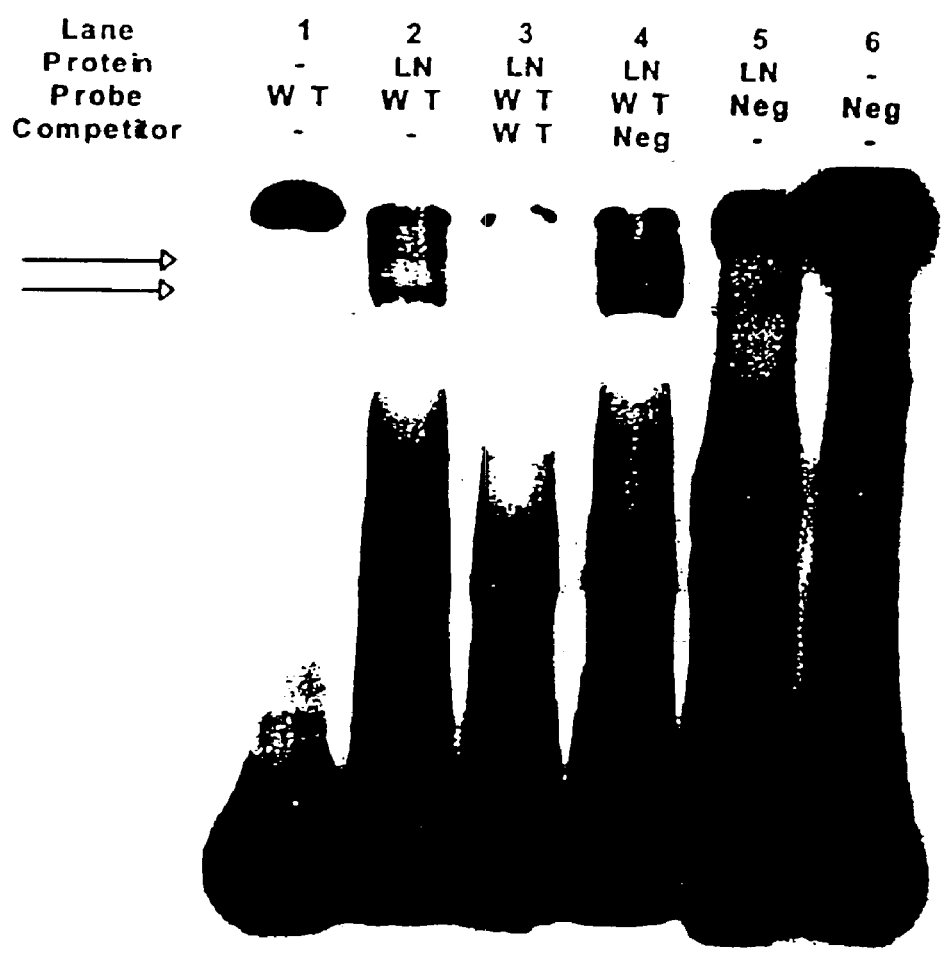
FIGS. 25A and 25B show autoradiographic images of electrophoretic mobility shift assay results. Lane designations are as follows.

The enhancer core segment bound proteins found only in the LNCaP nuclear extracts while the downstream segment did not bind any proteins found in LNCaP extracts (FIG. 25A). The radiolabeled enhancer core region was outcompeted by the addition of a 100-fold molar excess of the identical, non-radiolabeled sequence. The downstream segment was also used as a negative control and negative competitor to determine if the proteins that bound to the enhancer region did so in a sequence specific manner. The results are shown in FIG. 25A and suggest that the enhancer core region does bind proteins in LNCaPs in a sequence specific manner and this binding is not interrupted by the addition of a non-specific DNA competitor.

Figure 25B:
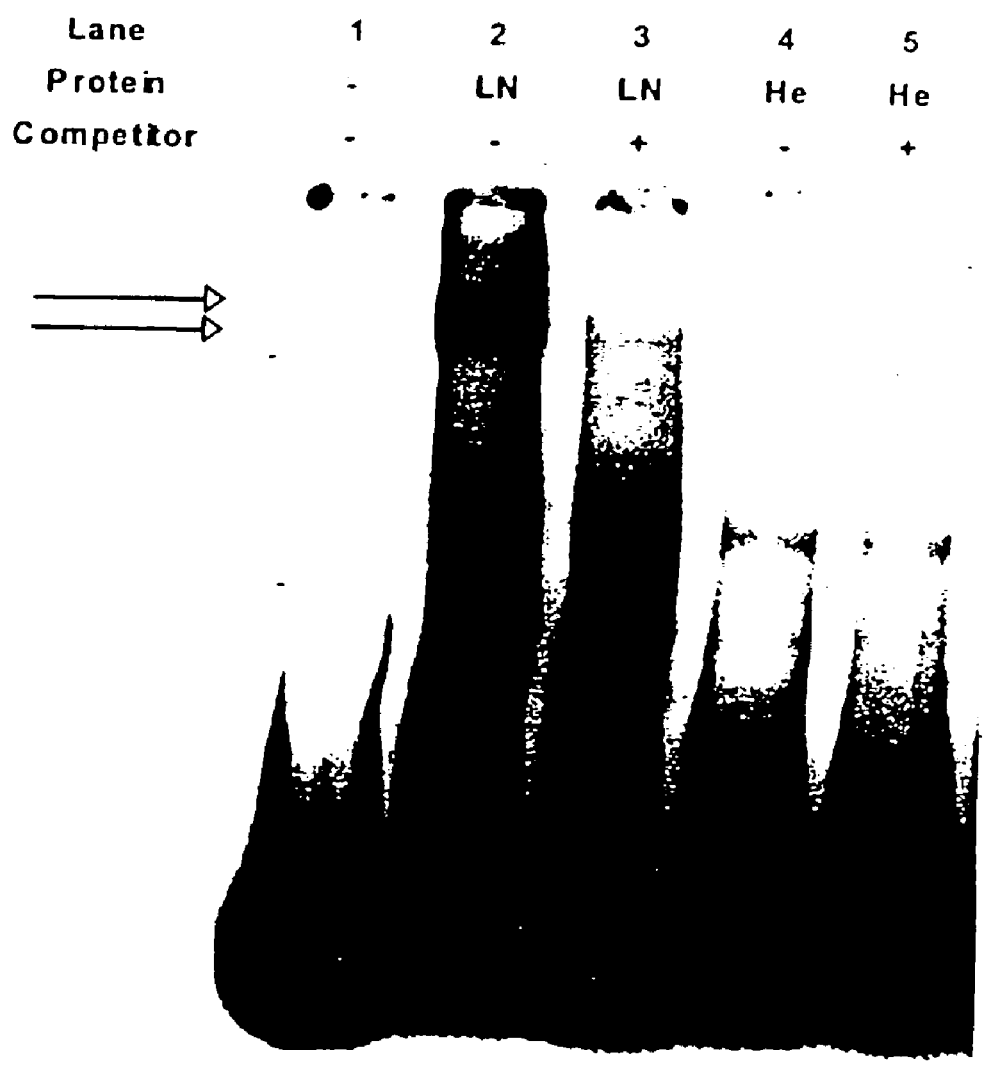

To determine if the enhancer core bound to proteins specific to LNCaPs, the radiolabeled enhancer core region was incubated with LNCaP nuclear proteins and HeLa nuclear proteins. The gel shown in FIG. 25B indicates that DNA-protein complexes were observed only in the reaction with LNCaP nuclear extracts (FIG. 25B, lane 2). This suggests that the enhancer core region studied binds proteins in a cell-specific manner and this enhancer also binds cellular specific factors found in LNCaPs but not in HeLa cells.

Example 17

In Vivo Characterization of CN764

Figure 26:
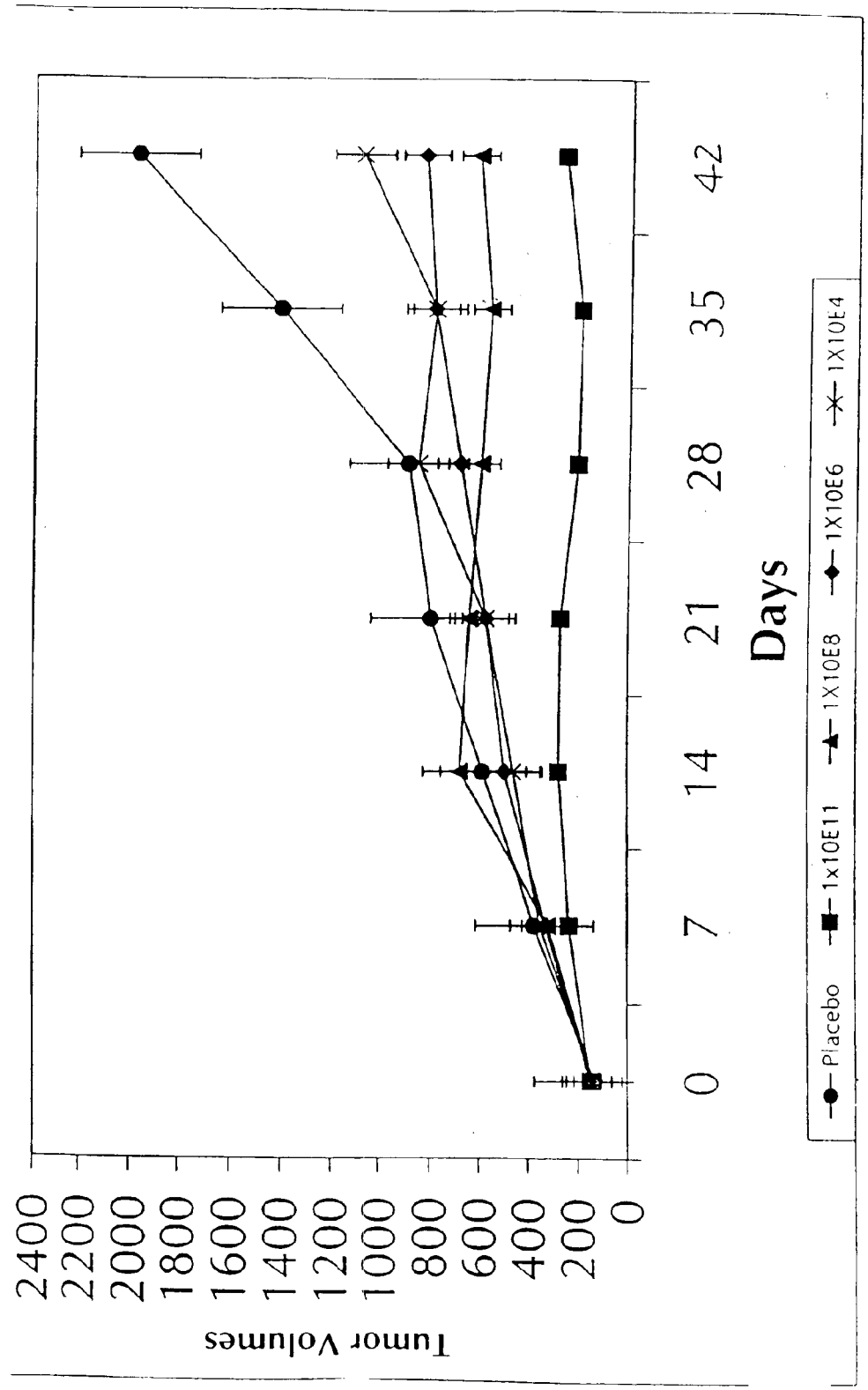
FIG. 26 shows the effect of CN764 on tumor cell growth in athymic mice following subcutaneous injection of LNCaP cells. Group 1 (circles) received PBS containing 10% glycerol; Group 2 (squares) received $1 \times 10^{11}$ viral particles; Group 3 (triangles) received $1 \times 10^8$ viral particles; Group 4 (diamonds) received $1 \times 10^6$ viral particles; and Group 5 (crosses) received $1 \times 10^4$ viral particles.

LNCaP xenografts were initiated by injecting $1 \times 10^6$ LNCaP cells in Matrigel subcutaneously into 12–16 week old Balb/c athymic (nu/nu) mice. LNCaP nude mouse xenografts were challenged at Day 1 and at Day 4 with a constant number of CN764 viral particles or with a vector lacking the gene. Mice with tumors were divided into 5 groups and treated with a total dose of CN764 as indicated in FIG. 26. Mice in Group 1 received PBS containing 10% glycerol (placebo). Tumors were measured on Day 0 and weekly thereafter. The tumors were monitored weekly for six weeks and their volume was plotted versus time. The results are shown in FIG. 26. Error bars represent the standard error for each sample group. At Day 42, the average tumor volume in Group 1 had increased to 1496% of the initial volume, while the average tumor volume in treatment Group 2 ($1\times10^{11}$ particles per animal) and Group 3 ($1\times10^8$ particles per animal) was increased to 179% and 438%, respectively, of the initial average volume. Beginning at Day 21, there was a statistically significant difference in average tumor volume between Group 1 and Group 2.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated polynucleotide comprising nucleotides about 8021 to about 8371 of SEQ ID NO:1, or a fragment thereof of comprising bases 8192–8206 of SEQ ID NO:1, wherein said polynucleotide or said fragment thereof has prostate-specific enhancer activity.

2. An isolated polynucleotide comprising nucleotides about 8021 to about 8371 of SEQ ID NO:1, wherein said polynucleotide has prostate-specific enhancer activity.

3. An isolated polynucleotide according to claim 2, wherein the polynucleotide comprises nucleotides about 7200 to about 8371 of SEQ ID NO:1, wherein said polynucleotide has enhancer activity.

4. An isolated polynucleotide according to claim 2, wherein the polynucleotide comprises nucleotides about 6859 to about 8627 of SEQ ID NO:1, wherein said polynucleotide has enhancer activity.

5. An isolated polynucleotide according to claim 2, wherein the polynucleotide comprises nucleotides about 5976 to about 9620 of SEQ ID NO:1, wherein said polynucleotide has enhancer activity.

6. An isolated polynucleotide according to claim 2, wherein the polynucleotide comprises nucleotides about 1 to about 9765 of SEQ ID NO:1, wherein said polynucleotide has enhancer activity.

7. An adenovirus vector for selective cytolysis of a prostate target cell comprising an adenovirus gene essential for replication under transcriptional control of a human glandular kallikrein transcription regulatory element (hKLK2-TRE), wherein said hKLK2-TRE comprises a promoter and nucleotides about 8021 to about 8371 of SEQ ID NO:1.

8. The adenovirus vector of claim 7, wherein said adenovirus gene essential for adenoviral replication is selected from the group consisting of E1A, E1B, E2 and E4.

9. The adenovirus vector according to claim 7 wherein said hKLK2-TRE comprises nucleotides about 7200 to about 8371 of SEQ ID NO:1.

10. The adenovirus vector according to claim 9, wherein said adenovirus gene essential for adenoviral replication is selected from the group consisting of E1A, E1B, E2 and E4.

11. The adenovirus vector according to claim 7 wherein said hKLK2-TRE comprises nucleotides about 6859 to about 8627 of SEQ ID NO:1.

12. The adenovirus vector according to claim 11, wherein said adenovirus gene essential for adenoviral replication is selected from the group consisting of E1A, E1B, E2 and E4.

13. The adenovirus vector according to claim 7 wherein said hKLK2-TRE comprises nucleotides about 5976 to about 9620 of SEQ ID NO:1.

14. The adenovirus vector according to claim 7 wherein said hKLK2-TRE comprises nucleotides about 1 to about 9765 of SEQ ID NO:1.

* * * * *